US010986867B2

(12) United States Patent
Bowen et al.

(10) Patent No.: US 10,986,867 B2
(45) Date of Patent: *Apr. 27, 2021

(54) VAPORIZATION DEVICE SYSTEMS AND METHODS

(71) Applicant: JUUL Labs, Inc., San Francisco, CA (US)

(72) Inventors: Adam Bowen, San Francisco, CA (US); Steven Christensen, San Francisco, CA (US); Christopher Nicholas HibmaCronan, Oakland, CA (US); James Monsees, San Francisco, CA (US); Joshua Morenstein, San Francisco, CA (US)

(73) Assignee: Juul Labs, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/114,207

(22) Filed: Aug. 27, 2018

(65) Prior Publication Data

US 2018/0360130 A1      Dec. 20, 2018

Related U.S. Application Data

(63) Continuation of application No. 15/379,898, filed on Dec. 15, 2016, now Pat. No. 10,058,129, which is a
(Continued)

(51) Int. Cl.
*A24F 40/40*   (2020.01)
*A24F 40/42*   (2020.01)
(Continued)

(52) U.S. Cl.
CPC .............. *A24F 40/40* (2020.01); *A24F 40/42* (2020.01); *A24F 40/51* (2020.01); *A24F 40/57* (2020.01)

(58) Field of Classification Search
CPC ........ A24F 47/008; A24F 40/40; A24F 40/42; A61M 15/06; A61M 11/042;
(Continued)

(56) References Cited

U.S. PATENT DOCUMENTS

D143,295 S    12/1945   Fisher
3,085,145 A    4/1963   Wray
(Continued)

FOREIGN PATENT DOCUMENTS

AT    507187 A4    3/2010
CA    2614869 A1   1/2006
(Continued)

OTHER PUBLICATIONS

"2011 New Eigarette GS-360,With 1.2ml Clearomizer(Id:5861467) Product Details—View 2011 New Eigarette GS-360,With 1.2ml Clearomizer from Green Sound High-Tech Co.,Ltd—EC21." EC21, Global B2B Marketplace—Connecting Global Buyers with Manufacturers, Suppliers, Exporters Worldwide, (2011), wo1138.en.ec21.com/2011_New_Eigarette_GS-360_With—5366965_5861467.html.
(Continued)

*Primary Examiner* — Joseph S Del Sole
*Assistant Examiner* — Jerzi H Moreno Hernandez
(74) *Attorney, Agent, or Firm* — Mintz, Levin, Cohn, Ferris, Glovsky and Popeo, P.C.

(57) ABSTRACT

Vaporizer cartridges are provided. In some implementations, a cartridge includes a storage compartment having a longitudinal and two transverse dimensions, a mouthpiece at a proximal end of the storage compartment, exposed contact surfaces proximate to and accessible from a distal end of the storage compartment, and a heater proximate to the distal end. The heater includes extended plate contacts, a wick disposed between the plate contacts, and a heating element
(Continued)

in contact with the plate contacts and the wick. Two opposed ends of the wick are disposed within the storage compartment and configured to contact the vaporizable material. The plate contact are electrically connected to the contact surfaces. Related systems, methods, and articles of manufacture are also described.

38 Claims, 22 Drawing Sheets

Related U.S. Application Data continuation-in-part of application No. 15/053,927, filed on Feb. 25, 2016, now Pat. No. 9,549,573, which is a continuation-in-part of application No. 14/581,666, filed on Dec. 23, 2014, now Pat. No. 10,058,124.

(60) Provisional application No. 62/294,281, filed on Feb. 11, 2016, provisional application No. 61/937,755, filed on Feb. 10, 2014, provisional application No. 61/936,593, filed on Feb. 6, 2014.

(51) Int. Cl.
*A24F 40/51* (2020.01)
*A24F 40/57* (2020.01)

(58) Field of Classification Search
CPC .. A61M 2205/8206; A61M 2205/3653; H05B 3/44; H05B 3/04; H05B 2203/014; H05B 2203/016; H05B 1/0244; H05B 2203/021; H05B 2203/022
See application file for complete search history.

(56) References Cited

U.S. PATENT DOCUMENTS

| | | |
|---|---|---|
| 3,271,719 A | 9/1966 | Ovshinsky |
| 3,918,451 A | 11/1975 | Steil |
| 3,934,117 A | 1/1976 | Schladitz |
| 4,171,000 A | 10/1979 | Uhle |
| D260,690 S | 9/1981 | Stutzer |
| D267,590 S | 1/1983 | Varma |
| 4,492,480 A | 1/1985 | Wadso et al. |
| D280,494 S | 9/1985 | Abel |
| 4,548,454 A | 10/1985 | Zeller et al. |
| 4,745,705 A | 5/1988 | Yamamoto et al. |
| D299,066 S | 12/1988 | Newell et al. |
| 4,793,365 A | 12/1988 | Sensabaugh, Jr. et al. |
| 4,811,731 A | 3/1989 | Newell et al. |
| D303,722 S | 9/1989 | Marlow et al. |
| 4,947,874 A | 8/1990 | Brooks et al. |
| 4,947,875 A | 8/1990 | Brooks et al. |
| D310,349 S | 9/1990 | Rowen |
| 4,993,436 A | 2/1991 | Bloom, Jr. |
| 5,042,509 A | 8/1991 | Banerjee et al. |
| 5,117,482 A | 5/1992 | Hauber |
| 5,144,962 A | 9/1992 | Counts et al. |
| D336,346 S | 6/1993 | Miller et al. |
| 5,259,786 A | 11/1993 | Huang |
| 5,261,424 A | 11/1993 | Sprinkel, Jr. |
| 5,269,327 A | 12/1993 | Counts et al. |
| H001271 H | 1/1994 | Shouse |
| 5,345,951 A | 9/1994 | Serrano et al. |
| 5,479,948 A | 1/1996 | Counts et al. |
| D368,552 S | 4/1996 | Adams |
| D371,633 S | 7/1996 | Chenard |
| D379,810 S | 6/1997 | Giordano, Jr. et al. |
| D382,146 S | 8/1997 | Sandy |
| 5,661,329 A | 8/1997 | Hiramoto et al. |
| 5,682,050 A | 10/1997 | Williams |
| D397,504 S | 8/1998 | Zelenik |
| D398,150 S | 9/1998 | Vonarburg |
| D405,007 S | 2/1999 | Naas, Sr. |
| D405,413 S | 2/1999 | Segers |
| 5,865,185 A | 2/1999 | Collins et al. |
| D411,332 S | 6/1999 | Zelenik |
| D412,279 S | 7/1999 | Brice |
| D422,884 S | 4/2000 | Lafond |
| D424,236 S | 5/2000 | Reed |
| 6,090,082 A | 7/2000 | King et al. |
| D433,532 S | 11/2000 | Higgins et al. |
| 6,155,268 A | 12/2000 | Takeuchi |
| 6,196,218 B1 | 3/2001 | Voges |
| 6,203,339 B1 | 3/2001 | Nieminen |
| 6,283,610 B1 | 9/2001 | Alajajian |
| D450,313 S | 11/2001 | Koinuma |
| D450,662 S | 11/2001 | Kwok |
| 6,516,796 B1 | 2/2003 | Cox et al. |
| D478,569 S | 8/2003 | Hussaini et al. |
| D478,897 S | 8/2003 | Tsuge |
| 6,637,430 B1 | 10/2003 | Voges et al. |
| 6,708,846 B1 | 3/2004 | Fuchs et al. |
| 6,743,030 B2 | 6/2004 | Lin et al. |
| 6,772,756 B2 | 8/2004 | Shayan |
| D500,301 S | 12/2004 | Deguchi |
| D500,302 S | 12/2004 | Deguchi |
| D505,922 S | 6/2005 | Mayo et al. |
| D506,447 S | 6/2005 | Mayo et al. |
| D506,731 S | 6/2005 | Mayo et al. |
| 6,909,840 B2 | 6/2005 | Harwig et al. |
| D507,244 S | 7/2005 | Mayo et al. |
| 7,019,491 B2 | 3/2006 | Bozzone et al. |
| D523,171 S | 6/2006 | Mitten et al. |
| D525,948 S | 8/2006 | Blair et al. |
| D528,992 S | 9/2006 | Hobart et al. |
| D529,044 S | 9/2006 | Andre et al. |
| D530,340 S | 10/2006 | Andre et al. |
| D531,190 S | 10/2006 | Lee et al. |
| D532,927 S | 11/2006 | Sann |
| D534,921 S | 1/2007 | Andre et al. |
| D535,261 S | 1/2007 | Daniels |
| D535,308 S | 1/2007 | Andre et al. |
| 7,173,222 B2 | 2/2007 | Cox et al. |
| D539,813 S | 4/2007 | Chen |
| D540,749 S | 4/2007 | Kaule |
| 7,214,075 B2 | 5/2007 | He et al. |
| D545,303 S | 6/2007 | Chang |
| D545,490 S | 6/2007 | Tai |
| D545,904 S | 7/2007 | Chen et al. |
| D546,782 S | 7/2007 | Poulet et al. |
| 7,275,941 B1 | 10/2007 | Bushby |
| D556,154 S | 11/2007 | Poulet et al. |
| D557,209 S | 12/2007 | Ahlgren et al. |
| D558,060 S | 12/2007 | Sir et al. |
| 7,318,435 B2 | 1/2008 | Pentafragas |
| D566,709 S | 4/2008 | Kim et al. |
| D568,298 S | 5/2008 | Lundgren et al. |
| D571,556 S | 6/2008 | Raile |
| D573,474 S | 7/2008 | Beam et al. |
| D576,619 S | 9/2008 | Udagawa et al. |
| D577,019 S | 9/2008 | Udagawa et al. |
| D577,150 S | 9/2008 | Bryman et al. |
| D579,934 S | 11/2008 | Okamoto et al. |
| D585,077 S | 1/2009 | Sheba et al. |
| D589,941 S | 4/2009 | Maier et al. |
| D591,758 S | 5/2009 | Lee |
| D607,403 S | 1/2010 | Hara et al. |
| 7,646,613 B2 | 1/2010 | Ligtenberg et al. |
| D610,588 S | 2/2010 | Chen |
| D611,409 S | 3/2010 | Green et al. |
| D616,753 S | 6/2010 | Beam et al. |
| 7,726,320 B2 | 6/2010 | Robinson et al. |
| 7,793,861 B2 | 9/2010 | Bankers et al. |
| 7,802,569 B2 | 9/2010 | Yeates et al. |
| D624,880 S | 10/2010 | Felegy, Jr. et al. |
| D631,055 S | 1/2011 | Gilbert et al. |
| D631,458 S | 1/2011 | Liao et al. |
| D631,885 S | 2/2011 | Maier |
| D634,735 S | 3/2011 | Maier |
| 7,905,236 B2 | 3/2011 | Bryman et al. |
| 7,913,688 B2 | 3/2011 | Cross et al. |

(56) References Cited

U.S. PATENT DOCUMENTS

| | | |
|---|---|---|
| D639,303 S | 6/2011 | Ni et al. |
| D639,782 S | 6/2011 | Kim |
| D641,718 S | 7/2011 | Sakai |
| D645,817 S | 9/2011 | Sasada et al. |
| D647,247 S | 10/2011 | Jones |
| D649,708 S | 11/2011 | Oneil |
| D649,932 S | 12/2011 | Symons |
| D656,496 S | 3/2012 | Andre et al. |
| D661,991 S | 6/2012 | Brummelhuis et al. |
| D664,636 S | 7/2012 | Robinson et al. |
| D669,530 S | 10/2012 | Hung |
| D670,659 S | 11/2012 | Ishikawa et al. |
| D674,748 S | 1/2013 | Ferber et al. |
| D676,741 S | 2/2013 | van Landsveld et al. |
| D681,445 S | 5/2013 | van Landsveld et al. |
| D682,841 S | 5/2013 | Suetake et al. |
| D686,987 S | 7/2013 | Vanstone et al. |
| D687,042 S | 7/2013 | Yoneta et al. |
| 8,485,099 B2 | 7/2013 | Skidmore et al. |
| 8,485,180 B2 | 7/2013 | Smutney et al. |
| 8,495,998 B2 | 7/2013 | Schennum |
| 8,499,766 B1 | 8/2013 | Newton |
| 8,522,776 B2 | 9/2013 | Wright et al. |
| 8,528,569 B1 | 9/2013 | Newton |
| D695,450 S | 12/2013 | Benassayag et al. |
| D700,572 S | 3/2014 | Esses |
| D703,679 S | 4/2014 | Chen |
| D704,629 S | 5/2014 | Liu |
| D704,634 S | 5/2014 | Eidelman et al. |
| D705,918 S | 5/2014 | Robinson et al. |
| D707,389 S | 6/2014 | Liu |
| D707,688 S | 6/2014 | Wu |
| 8,752,545 B2 | 6/2014 | Buchberger |
| D708,727 S | 7/2014 | Postma |
| D711,389 S | 8/2014 | Sun et al. |
| D711,891 S | 8/2014 | Emami et al. |
| D712,347 S | 9/2014 | Awiszus et al. |
| 8,833,364 B2 | 9/2014 | Buchberger |
| 8,881,738 B2 | 11/2014 | Bryman |
| 8,893,726 B2 | 11/2014 | Hon |
| 8,897,628 B2 | 11/2014 | Conley et al. |
| D718,723 S | 12/2014 | Clymer et al. |
| D718,933 S | 12/2014 | Brown, Jr. |
| D720,095 S | 12/2014 | Alima |
| D721,202 S * | 1/2015 | Liu .............................. D27/101 |
| D723,735 S | 3/2015 | Liu |
| D723,736 S | 3/2015 | Liu |
| D723,737 S | 3/2015 | Liu |
| D724,037 S | 3/2015 | Yoshioka |
| D725,310 S | 3/2015 | Eksouzian |
| D725,821 S | 3/2015 | Levin et al. |
| 8,991,402 B2 | 3/2015 | Bowen et al. |
| D726,727 S | 4/2015 | Holz et al. |
| 9,010,335 B1 | 4/2015 | Scatterday |
| D728,855 S | 5/2015 | Liu |
| D729,277 S | 5/2015 | Uchida |
| D729,444 S | 5/2015 | Leidel |
| D729,445 S | 5/2015 | Leidel |
| D730,571 S | 5/2015 | Chen |
| D730,572 S | 5/2015 | Leidel |
| D731,114 S | 6/2015 | Leidel |
| D732,733 S | 6/2015 | Spagnolo et al. |
| D733,356 S | 6/2015 | Leidel |
| 9,072,321 B2 | 7/2015 | Liu |
| 9,078,473 B2 | 7/2015 | Worm et al. |
| D737,508 S | 8/2015 | Liu |
| 9,101,729 B2 | 8/2015 | Liu |
| D738,038 S | 9/2015 | Smith |
| D739,973 S | 9/2015 | Chao |
| 9,132,248 B2 | 9/2015 | Qiu |
| 9,167,849 B2 | 10/2015 | Adamic |
| D742,492 S | 11/2015 | Robinson et al. |
| D743,099 S | 11/2015 | Oglesby |
| D744,342 S | 12/2015 | Blasko et al. |
| D745,004 S | 12/2015 | Kim |
| 9,220,302 B2 | 12/2015 | DePiano et al. |
| 9,247,773 B2 | 2/2016 | Memari et al. |
| D752,284 S | 3/2016 | Doster |
| 9,271,529 B2 | 3/2016 | Alima |
| 9,282,772 B2 | 3/2016 | Tucker et al. |
| 9,289,014 B2 | 3/2016 | Tucker et al. |
| D753,090 S | 4/2016 | Langhammer et al. |
| D755,733 S | 5/2016 | Ikegaya et al. |
| D755,735 S | 5/2016 | Kashimoto |
| D756,032 S | 5/2016 | Chen |
| D757,690 S | 5/2016 | Lee et al. |
| 9,345,541 B2 | 5/2016 | Greeley et al. |
| D759,031 S | 6/2016 | Ozolins et al. |
| D760,431 S | 6/2016 | Liu |
| 9,364,800 B2 | 6/2016 | Dubief |
| 9,386,805 B2 | 7/2016 | Liu |
| D763,203 S | 8/2016 | Ikegaya et al. |
| D763,204 S | 8/2016 | Ikegaya et al. |
| 9,408,416 B2 | 8/2016 | Monsees et al. |
| 9,414,629 B2 | 8/2016 | Egoyants et al. |
| 9,420,829 B2 | 8/2016 | Thorens et al. |
| 9,423,152 B2 | 8/2016 | Ampolini et al. |
| 9,427,022 B2 | 8/2016 | Levin et al. |
| D766,873 S | 9/2016 | Washio |
| D768,920 S | 10/2016 | Jones et al. |
| D769,830 S | 10/2016 | Clymer et al. |
| D770,395 S | 11/2016 | Clymer et al. |
| D773,114 S | 11/2016 | Leidel et al. |
| 9,498,588 B2 | 11/2016 | Benassayag et al. |
| 9,504,279 B2 | 11/2016 | Chen |
| D773,727 S | 12/2016 | Eksouzian |
| D774,514 S | 12/2016 | Turksu et al. |
| 9,510,623 B2 | 12/2016 | Tucker et al. |
| 9,516,899 B2 | 12/2016 | Plojoux et al. |
| 9,526,273 B2 | 12/2016 | Liu |
| D776,338 S | 1/2017 | Lomeli |
| 9,549,573 B2 * | 1/2017 | Monsees .................. H05B 3/04 |
| D779,677 S | 2/2017 | Chen |
| D779,719 S | 2/2017 | Qiu |
| D780,179 S | 2/2017 | Bae et al. |
| 9,609,893 B2 | 4/2017 | Novak, III et al. |
| 9,675,109 B2 | 6/2017 | Monsees et al. |
| D793,004 S | 7/2017 | Liu |
| 9,714,878 B2 | 7/2017 | Powers et al. |
| 9,723,876 B2 | 8/2017 | Cadieux et al. |
| 9,723,877 B2 | 8/2017 | Wong et al. |
| 9,772,245 B2 | 9/2017 | Besling et al. |
| D799,746 S | 10/2017 | Leidel et al. |
| D800,132 S | 10/2017 | Maus et al. |
| 9,781,953 B2 | 10/2017 | Verleur et al. |
| 9,795,168 B2 | 10/2017 | Zhu |
| 9,801,413 B2 | 10/2017 | Zhu |
| D802,206 S | 11/2017 | Huang et al. |
| D802,838 S | 11/2017 | Clark et al. |
| 9,814,263 B2 | 11/2017 | Cochand et al. |
| 9,814,265 B2 | 11/2017 | Rinker et al. |
| D806,311 S | 12/2017 | Smith |
| 9,844,234 B2 | 12/2017 | Thorens et al. |
| D808,073 S | 1/2018 | Leidel |
| 9,861,135 B2 | 1/2018 | Chen |
| D811,003 S | 2/2018 | Folyan |
| D815,346 S | 4/2018 | Bagai |
| 9,974,743 B2 | 5/2018 | Rose et al. |
| D819,881 S | 6/2018 | Qiu |
| D822,896 S | 7/2018 | Durand |
| D825,102 S | 8/2018 | Bowen et al. |
| 10,039,321 B2 | 8/2018 | Verleur et al. |
| 10,045,568 B2 * | 8/2018 | Monsees ............... A24F 47/008 |
| 10,058,122 B2 | 8/2018 | Steingraber et al. |
| 10,058,124 B2 * | 8/2018 | Monsees ............... A24F 47/008 |
| 10,058,129 B2 * | 8/2018 | Monsees ............... A24F 47/008 |
| 10,085,481 B2 | 10/2018 | Verleur et al. |
| 10,092,713 B2 | 10/2018 | Terry et al. |
| 10,104,915 B2 | 10/2018 | Bowen et al. |
| 10,111,470 B2 | 10/2018 | Monsees et al. |
| D834,702 S | 11/2018 | Evans et al. |
| 10,117,465 B2 | 11/2018 | Monsees et al. |
| 10,117,466 B2 | 11/2018 | Monsees et al. |
| D836,190 S | 12/2018 | Evans et al. |

(56) References Cited

U.S. PATENT DOCUMENTS

| | | |
|---|---|---|
| D836,831 S | 12/2018 | Cividi |
| D836,834 S | 12/2018 | Cividi |
| 10,143,233 B2 | 12/2018 | Dubief et al. |
| 10,195,345 B2 | 2/2019 | Senior et al. |
| 10,195,370 B2 | 2/2019 | Chen |
| D842,237 S | 3/2019 | Qiu et al. |
| D844,235 S | 3/2019 | Cividi |
| D845,964 S | 4/2019 | Kim et al. |
| 10,264,823 B2 | 4/2019 | Monsees et al. |
| 2002/0043262 A1 | 4/2002 | Langford et al. |
| 2002/0088469 A1 | 7/2002 | Rennecamp |
| 2003/0033055 A1 | 2/2003 | McRae et al. |
| 2003/0096542 A1 | 5/2003 | Kojima |
| 2003/0150451 A1 | 8/2003 | Shayan |
| 2003/0226837 A1 | 12/2003 | Blake et al. |
| 2004/0050382 A1 | 3/2004 | Goodchild |
| 2004/0099266 A1 | 5/2004 | Cross et al. |
| 2005/0029137 A1 | 2/2005 | Wang |
| 2005/0134215 A1 | 6/2005 | Bozzone et al. |
| 2005/0252511 A1 | 11/2005 | Pentafragas |
| 2006/0141344 A1 | 6/2006 | Chen et al. |
| 2006/0191546 A1 | 8/2006 | Takano et al. |
| 2006/0191594 A1 | 8/2006 | Py |
| 2006/0207466 A1 | 9/2006 | McNulty et al. |
| 2007/0074734 A1 | 4/2007 | Braunshteyn et al. |
| 2007/0089757 A1 | 4/2007 | Bryman |
| 2007/0119450 A1 | 5/2007 | Wharton et al. |
| 2007/0144514 A1 | 6/2007 | Yeates et al. |
| 2007/0229025 A1 | 10/2007 | Tsai et al. |
| 2007/0277816 A1 | 12/2007 | Morrison et al. |
| 2007/0283972 A1 | 12/2007 | Monsees et al. |
| 2008/0023003 A1 | 1/2008 | Rosenthal |
| 2008/0029095 A1 | 2/2008 | Esser |
| 2008/0068602 A1 | 3/2008 | Delaage et al. |
| 2008/0092912 A1 | 4/2008 | Robinson et al. |
| 2008/0257367 A1 | 10/2008 | Paterno et al. |
| 2008/0302374 A1 | 12/2008 | Wengert et al. |
| 2009/0095287 A1 | 4/2009 | Emarlou |
| 2009/0151717 A1 | 6/2009 | Bowen et al. |
| 2009/0230117 A1 | 9/2009 | Fernando et al. |
| 2009/0260641 A1 | 10/2009 | Monsees et al. |
| 2009/0272379 A1 | 11/2009 | Thorens et al. |
| 2009/0283103 A1 | 11/2009 | Nielsen et al. |
| 2010/0031968 A1 | 2/2010 | Sheikh et al. |
| 2010/0163063 A1 | 7/2010 | Fernando et al. |
| 2010/0163065 A1 | 7/2010 | Chang |
| 2010/0192949 A1 | 8/2010 | Wright et al. |
| 2010/0194337 A1 | 8/2010 | Opolka |
| 2010/0253279 A1 | 10/2010 | Matthias |
| 2011/0094523 A1 | 4/2011 | Thorens et al. |
| 2011/0125146 A1 | 5/2011 | Greeley et al. |
| 2011/0155153 A1 | 6/2011 | Thorens et al. |
| 2011/0192397 A1 | 8/2011 | Saskar et al. |
| 2011/0226236 A1* | 9/2011 | Buchberger ......... A61M 11/041 128/200.23 |
| 2011/0265806 A1 | 11/2011 | Alarcon et al. |
| 2011/0303231 A1 | 12/2011 | Li et al. |
| 2012/0018529 A1 | 1/2012 | Gammon et al. |
| 2012/0048266 A1 | 3/2012 | Alelov |
| 2012/0186594 A1 | 7/2012 | Liu |
| 2012/0188687 A1 | 7/2012 | Yamamoto |
| 2012/0199146 A1 | 8/2012 | Marangos |
| 2012/0199663 A1 | 8/2012 | Qiu |
| 2012/0223673 A1 | 9/2012 | Chen et al. |
| 2012/0255546 A1 | 10/2012 | Goetz et al. |
| 2012/0255567 A1 | 10/2012 | Rose et al. |
| 2012/0318882 A1 | 12/2012 | Abehasera |
| 2013/0037041 A1 | 2/2013 | Worm et al. |
| 2013/0042865 A1 | 2/2013 | Monsees et al. |
| 2013/0081642 A1 | 4/2013 | Safari |
| 2013/0099725 A1 | 4/2013 | Burrell et al. |
| 2013/0104916 A1 | 5/2013 | Bellinger et al. |
| 2013/0115821 A1 | 5/2013 | Golko et al. |
| 2013/0152922 A1 | 6/2013 | Benassayag et al. |
| 2013/0168880 A1 | 7/2013 | Duke |
| 2013/0182421 A1 | 7/2013 | Popper et al. |
| 2013/0192615 A1 | 8/2013 | Tucker et al. |
| 2013/0192619 A1 | 8/2013 | Tucker et al. |
| 2013/0192623 A1 | 8/2013 | Tucker et al. |
| 2013/0213419 A1 | 8/2013 | Tucker et al. |
| 2013/0220314 A1 | 8/2013 | Bottom |
| 2013/0220315 A1 | 8/2013 | Conley et al. |
| 2013/0220316 A1 | 8/2013 | Oglesby et al. |
| 2013/0228190 A1* | 9/2013 | Weiss ................ A24F 47/002 131/328 |
| 2013/0228191 A1 | 9/2013 | Newton |
| 2013/0233086 A1 | 9/2013 | Besling et al. |
| 2013/0253433 A1 | 9/2013 | Senior et al. |
| 2013/0255675 A1* | 10/2013 | Liu ..................... A61M 11/041 128/202.21 |
| 2013/0255702 A1 | 10/2013 | Griffith, Jr. et al. |
| 2013/0263869 A1 | 10/2013 | Zhu |
| 2013/0298905 A1 | 11/2013 | Levin et al. |
| 2013/0306065 A1 | 11/2013 | Thorens et al. |
| 2013/0306084 A1 | 11/2013 | Flick |
| 2013/0319435 A1 | 12/2013 | Flick |
| 2013/0319438 A1 | 12/2013 | Liu |
| 2013/0323941 A1 | 12/2013 | Zeliff et al. |
| 2013/0333700 A1 | 12/2013 | Buchberger |
| 2013/0333711 A1 | 12/2013 | Liu |
| 2014/0007891 A1 | 1/2014 | Liu |
| 2014/0014124 A1 | 1/2014 | Glasberg et al. |
| 2014/0014126 A1 | 1/2014 | Peleg et al. |
| 2014/0053856 A1 | 2/2014 | Liu |
| 2014/0053857 A1 | 2/2014 | Liu |
| 2014/0053858 A1 | 2/2014 | Liu |
| 2014/0107815 A1 | 4/2014 | LaMothe |
| 2014/0116455 A1 | 5/2014 | Youn |
| 2014/0123990 A1 | 5/2014 | Timmermans |
| 2014/0144429 A1* | 5/2014 | Wensley ............... A61M 15/06 128/200.14 |
| 2014/0144453 A1* | 5/2014 | Capuano ............... A24F 47/008 131/329 |
| 2014/0150783 A1 | 6/2014 | Liu |
| 2014/0150784 A1 | 6/2014 | Liu |
| 2014/0150810 A1 | 6/2014 | Hon |
| 2014/0161301 A1 | 6/2014 | Merenda |
| 2014/0174458 A1 | 6/2014 | Katz |
| 2014/0178461 A1 | 6/2014 | Rigas |
| 2014/0182610 A1 | 7/2014 | Liu |
| 2014/0190496 A1 | 7/2014 | Wensley et al. |
| 2014/0202454 A1 | 7/2014 | Buchberger |
| 2014/0216483 A1 | 8/2014 | Alima |
| 2014/0224244 A1* | 8/2014 | Liu ........................ H05B 3/14 128/202.21 |
| 2014/0224267 A1 | 8/2014 | Levitz et al. |
| 2014/0253144 A1 | 9/2014 | Novak, III et al. |
| 2014/0261408 A1* | 9/2014 | DePiano ............... A24F 47/008 128/202.21 |
| 2014/0261486 A1 | 9/2014 | Potter et al. |
| 2014/0261487 A1 | 9/2014 | Chapman et al. |
| 2014/0261490 A1 | 9/2014 | Kane |
| 2014/0261493 A1 | 9/2014 | Smith et al. |
| 2014/0261495 A1* | 9/2014 | Novak, III ........... A24F 47/008 131/329 |
| 2014/0270727 A1 | 9/2014 | Ampolini et al. |
| 2014/0270729 A1* | 9/2014 | DePiano ............... A24F 47/008 392/397 |
| 2014/0270730 A1* | 9/2014 | DePiano ............... A24F 47/008 392/404 |
| 2014/0276536 A1 | 9/2014 | Estes |
| 2014/0283858 A1 | 9/2014 | Liu |
| 2014/0299125 A1 | 10/2014 | Buchberger |
| 2014/0299137 A1 | 10/2014 | Kieckbusch et al. |
| 2014/0299141 A1 | 10/2014 | Flick |
| 2014/0305454 A1 | 10/2014 | Rinker et al. |
| 2014/0332020 A1 | 11/2014 | Li et al. |
| 2014/0332022 A1* | 11/2014 | Li ......................... A24F 47/008 131/329 |
| 2014/0334804 A1 | 11/2014 | Choi |
| 2014/0338685 A1 | 11/2014 | Amir |
| 2014/0345631 A1 | 11/2014 | Bowen et al. |
| 2014/0345633 A1 | 11/2014 | Talon et al. |

(56) References Cited

U.S. PATENT DOCUMENTS

| | | |
|---|---|---|
| 2014/0355969 A1 | 12/2014 | Stern |
| 2014/0363145 A1* | 12/2014 | Plojoux ............... A24F 47/008 392/386 |
| 2014/0366898 A1 | 12/2014 | Monsees et al. |
| 2014/0373857 A1 | 12/2014 | Steinberg |
| 2014/0376895 A1 | 12/2014 | Han |
| 2015/0013696 A1 | 1/2015 | Plojoux et al. |
| 2015/0020831 A1 | 1/2015 | Weigensberg et al. |
| 2015/0027457 A1 | 1/2015 | Janardhan et al. |
| 2015/0027460 A1 | 1/2015 | Liu |
| 2015/0027469 A1 | 1/2015 | Tucker et al. |
| 2015/0027471 A1* | 1/2015 | Feldman ............... H05B 3/16 131/329 |
| 2015/0034103 A1 | 2/2015 | Hon |
| 2015/0034104 A1* | 2/2015 | Zhou .................. A24F 47/008 131/329 |
| 2015/0034507 A1 | 2/2015 | Liu |
| 2015/0053214 A1 | 2/2015 | Alarcon et al. |
| 2015/0059783 A1 | 3/2015 | Liu |
| 2015/0059787 A1 | 3/2015 | Qiu |
| 2015/0068523 A1 | 3/2015 | Powers et al. |
| 2015/0070832 A1 | 3/2015 | Schneider et al. |
| 2015/0083147 A1* | 3/2015 | Schiff ................. A24F 47/008 131/329 |
| 2015/0090256 A1 | 4/2015 | Chung |
| 2015/0090281 A1 | 4/2015 | Chen |
| 2015/0101606 A1 | 4/2015 | White |
| 2015/0101625 A1 | 4/2015 | Newton et al. |
| 2015/0101626 A1 | 4/2015 | Li et al. |
| 2015/0118895 A1 | 4/2015 | Zheng et al. |
| 2015/0128971 A1 | 5/2015 | Verleur et al. |
| 2015/0128972 A1 | 5/2015 | Verleur et al. |
| 2015/0128976 A1* | 5/2015 | Verleur ............... A24F 47/008 131/329 |
| 2015/0136155 A1 | 5/2015 | Verleur et al. |
| 2015/0136158 A1 | 5/2015 | Stevens et al. |
| 2015/0157055 A1* | 6/2015 | Lord .................... A24F 47/008 131/329 |
| 2015/0164147 A1 | 6/2015 | Verleur et al. |
| 2015/0173124 A1 | 6/2015 | Qiu |
| 2015/0181937 A1 | 7/2015 | Dubief et al. |
| 2015/0181940 A1 | 7/2015 | Liu |
| 2015/0181944 A1 | 7/2015 | Li et al. |
| 2015/0189919 A1 | 7/2015 | Liu |
| 2015/0196060 A1 | 7/2015 | Wensley et al. |
| 2015/0208728 A1 | 7/2015 | Lord |
| 2015/0208729 A1 | 7/2015 | Monsees et al. |
| 2015/0216237 A1 | 8/2015 | Wensley et al. |
| 2015/0217068 A1 | 8/2015 | Wakalopulos |
| 2015/0223521 A1 | 8/2015 | Menting et al. |
| 2015/0237916 A1 | 8/2015 | Farine et al. |
| 2015/0245654 A1 | 9/2015 | Memari et al. |
| 2015/0245655 A1 | 9/2015 | Memari et al. |
| 2015/0245657 A1 | 9/2015 | Memari et al. |
| 2015/0245658 A1 | 9/2015 | Worm et al. |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0245669 A1 | 9/2015 | Cadieux et al. |
| 2015/0257447 A1 | 9/2015 | Sullivan |
| 2015/0282525 A1 | 10/2015 | Plojoux et al. |
| 2015/0282526 A1 | 10/2015 | Wu |
| 2015/0289565 A1 | 10/2015 | Cadieux et al. |
| 2015/0296889 A1 | 10/2015 | Liu |
| 2015/0305409 A1 | 10/2015 | Verleur et al. |
| 2015/0313283 A1 | 11/2015 | Collett et al. |
| 2015/0313287 A1 | 11/2015 | Verleur et al. |
| 2015/0320116 A1 | 11/2015 | Bleloch et al. |
| 2015/0327595 A1 | 11/2015 | Scatterday |
| 2015/0327597 A1 | 11/2015 | Li et al. |
| 2015/0335071 A1* | 11/2015 | Brinkley ............... F22B 1/284 131/328 |
| 2015/0351455 A1 | 12/2015 | Liu |
| 2015/0357608 A1 | 12/2015 | Huang |
| 2015/0359263 A1 | 12/2015 | Bellinger |
| 2016/0007651 A1 | 1/2016 | Ampolini et al. |
| 2016/0021933 A1 | 1/2016 | Thorens et al. |
| 2016/0044962 A1 | 2/2016 | Thorens et al. |
| 2016/0095356 A1 | 4/2016 | Chan |
| 2016/0106153 A1 | 4/2016 | Zhu |
| 2016/0143365 A1 | 5/2016 | Liu |
| 2016/0150824 A1 | 6/2016 | Memari et al. |
| 2016/0157523 A1* | 6/2016 | Liu ..................... A24F 47/008 392/395 |
| 2016/0174611 A1 | 6/2016 | Monsees et al. |
| 2016/0198767 A1* | 7/2016 | Verleur ............... H05B 1/0202 392/386 |
| 2016/0198768 A1 | 7/2016 | Liu |
| 2016/0219934 A1 | 8/2016 | Li et al. |
| 2016/0270442 A1 | 9/2016 | Liu |
| 2016/0278436 A1 | 9/2016 | Verleur et al. |
| 2016/0331032 A1 | 11/2016 | Malgat et al. |
| 2016/0345626 A1 | 12/2016 | Wong et al. |
| 2016/0353804 A1 | 12/2016 | Lord |
| 2016/0360790 A1 | 12/2016 | Calfee et al. |
| 2016/0374393 A1* | 12/2016 | Chen ................... A24F 47/008 131/329 |
| 2017/0035115 A1 | 2/2017 | Monsees et al. |
| 2017/0095005 A1 | 4/2017 | Monsees et al. |
| 2017/0119044 A1 | 5/2017 | Oligschlaeger et al. |
| 2017/0156404 A1 | 6/2017 | Novak, III et al. |
| 2017/0157341 A1 | 6/2017 | Pandya et al. |
| 2017/0197046 A1 | 7/2017 | Buchberger |
| 2017/0231276 A1 | 8/2017 | Mironov et al. |
| 2017/0231282 A1 | 8/2017 | Bowen et al. |
| 2017/0302324 A1 | 10/2017 | Stanimirovic et al. |
| 2017/0318861 A1 | 11/2017 | Thorens |
| 2017/0367410 A1 | 12/2017 | Hon |
| 2018/0070644 A1 | 3/2018 | Monsees et al. |
| 2018/0177234 A1 | 6/2018 | Lee |
| 2019/0037926 A1 | 2/2019 | Qiu |

FOREIGN PATENT DOCUMENTS

| | | |
|---|---|---|
| CA | 2641869 A1 | 5/2010 |
| CH | 105346 A | 6/1924 |
| CH | 507187 A | 5/1971 |
| CN | 3037571 | 11/1995 |
| CN | 2643529 Y | 9/2004 |
| CN | 1630476 A | 6/2005 |
| CN | 1906096 A | 1/2007 |
| CN | 201104488 Y | 8/2008 |
| CN | 101277622 A | 10/2008 |
| CN | 301111821 | 1/2010 |
| CN | 100589726 C | 2/2010 |
| CN | 201408820 Y | 2/2010 |
| CN | 101951796 A | 1/2011 |
| CN | 301485739 | 3/2011 |
| CN | 201781984 U | 4/2011 |
| CN | 301547686 | 5/2011 |
| CN | 102160906 A | 8/2011 |
| CN | 102176941 A | 9/2011 |
| CN | 202004499 U | 10/2011 |
| CN | 301753038 | 12/2011 |
| CN | 301797114 | 1/2012 |
| CN | 202218034 U | 5/2012 |
| CN | 301955679 | 6/2012 |
| CN | 301970169 | 6/2012 |
| CN | 202385728 U | 8/2012 |
| CN | 202603608 U | 12/2012 |
| CN | 202663148 U | 1/2013 |
| CN | 102920028 A | 2/2013 |
| CN | 102970885 A | 3/2013 |
| CN | 202890462 U | 4/2013 |
| CN | 302396126 | 4/2013 |
| CN | 302396126 S * | 4/2013 |
| CN | 202941411 U | 5/2013 |
| CN | 302485056 | 6/2013 |
| CN | 203040683 U | 7/2013 |
| CN | 203072896 U | 7/2013 |
| CN | 203087525 U | 7/2013 |
| CN | 103237469 A | 8/2013 |

(56) References Cited

FOREIGN PATENT DOCUMENTS

| | | |
|---|---|---|
| CN | 103237470 A | 8/2013 |
| CN | 203152489 U | 8/2013 |
| CN | 203168035 U | 9/2013 |
| CN | 203182012 U | 9/2013 |
| CN | 302660481 | 11/2013 |
| CN | 302660490 | 11/2013 |
| CN | 203327953 U | 12/2013 |
| CN | 203353689 U | 12/2013 |
| CN | 302680448 | 12/2013 |
| CN | 302799554 | 4/2014 |
| CN | 302803209 | 4/2014 |
| CN | 302810246 | 4/2014 |
| CN | 302814868 | 5/2014 |
| CN | 302859209 | 6/2014 |
| CN | 104010529 A | 8/2014 |
| CN | 302884434 | 8/2014 |
| CN | 302926289 | 8/2014 |
| CN | 104055223 A | 9/2014 |
| CN | 302950830 | 9/2014 |
| CN | 303044212 | 12/2014 |
| CN | 204120231 U | 1/2015 |
| CN | 303089422 | 1/2015 |
| CN | 303091331 | 1/2015 |
| CN | 204132390 U | 2/2015 |
| CN | 303103391 | 2/2015 |
| CN | 104382237 A | 3/2015 |
| CN | 204217907 U | 3/2015 |
| CN | 303210086 | 5/2015 |
| CN | 104738816 A | 7/2015 |
| CN | 204466899 U | 7/2015 |
| CN | 303332720 | 8/2015 |
| CN | 105011375 A | 11/2015 |
| CN | 303103389 | 11/2015 |
| CN | 303457556 | 11/2015 |
| CN | 204905326 U | 12/2015 |
| CN | 303568163 | 1/2016 |
| CN | 303574274 | 1/2016 |
| CN | 303103390 | 2/2016 |
| CN | 303686002 | 5/2016 |
| CN | 303721535 | 6/2016 |
| DE | 1093936 B | 12/1960 |
| DE | 19619536 A1 | 10/1997 |
| DE | 102006004484 A1 | 8/2007 |
| DE | 102007011120 A1 | 9/2008 |
| DE | 102008046932 A1 | 5/2009 |
| EM | 002626416-001 | 4/2015 |
| EM | 002626416-002 | 4/2015 |
| EP | 0762258 A2 | 3/1997 |
| EP | 0845220 A1 | 6/1998 |
| EP | 1093936 A1 | 4/2001 |
| EP | 1736177 A1 | 12/2006 |
| EP | 2113178 A1 | 11/2009 |
| EP | 2399636 A1 | 12/2011 |
| EP | 2460424 A1 | 6/2012 |
| EP | 2489391 A1 | 8/2012 |
| EP | 2606756 A1 | 6/2013 |
| EP | 2609821 A1 | 7/2013 |
| EP | 2614731 A1 | 7/2013 |
| EP | 2654471 A1 | 10/2013 |
| EP | 2888964 A1 | 7/2015 |
| EP | 2895390 A1 | 7/2015 |
| EP | 2944207 A1 | 11/2015 |
| EP | 3024343 A2 | 6/2016 |
| EP | 3000245 | 8/2016 |
| GB | 2264237 A | 8/1993 |
| GB | 2266466 A | 11/1993 |
| GB | 2504074 A | 1/2014 |
| GB | 2560653 A | 9/2018 |
| JP | D1144098 | 6/2002 |
| JP | 3325591 B2 | 9/2002 |
| JP | 2013507976 A | 3/2013 |
| JP | 2013516159 A | 5/2013 |
| KR | 100579783 B1 | 5/2006 |
| KR | 101011453 B1 | 1/2011 |
| KR | 20120008751 A | 2/2012 |
| KR | 20120006582 U | 9/2012 |
| KR | 20120105655 A | 9/2012 |
| KR | 20120113519 A | 10/2012 |
| KR | 102012013200 | 12/2012 |
| KR | 20130092252 A | 8/2013 |
| KR | 20130106741 A | 9/2013 |
| KR | 20130107658 A * | 10/2013 |
| KR | 20130122713 A | 11/2013 |
| KR | 30-0825216 | 11/2015 |
| SG | 11201707778 W | 10/2017 |
| TW | I320698 B | 2/2010 |
| WO | WO-2003061716 A1 | 7/2003 |
| WO | WO-03103387 A2 | 12/2003 |
| WO | WO-2008138650 A1 | 11/2008 |
| WO | WO-2009079641 A2 | 6/2009 |
| WO | WO-2009132793 A1 | 11/2009 |
| WO | WO-2010140841 A2 | 12/2010 |
| WO | WO-2011050943 A1 | 5/2011 |
| WO | WO-2011079932 A1 | 7/2011 |
| WO | WO-2011107737 A1 | 9/2011 |
| WO | WO-2011146174 A2 | 11/2011 |
| WO | WO-2011147691 A1 | 12/2011 |
| WO | WO-2012014490 A1 | 2/2012 |
| WO | WO-2012043941 A1 | 4/2012 |
| WO | WO-2012059726 A2 | 5/2012 |
| WO | WO-2012062600 A1 | 5/2012 |
| WO | WO-2012085203 A1 | 6/2012 |
| WO | WO-D79112-0010 | 12/2012 |
| WO | WO-2013034453 A1 | 3/2013 |
| WO | WO-2013034456 A1 | 3/2013 |
| WO | WO-2013044537 A1 | 4/2013 |
| WO | WO-2013045582 A2 | 4/2013 |
| WO | WO-2013060784 A2 | 5/2013 |
| WO | WO-2013068100 A1 | 5/2013 |
| WO | WO-2013075439 A1 | 5/2013 |
| WO | WO-2013083631 A1 | 6/2013 |
| WO | WO-2013083634 A1 | 6/2013 |
| WO | WO-2013083635 A1 | 6/2013 |
| WO | WO-2013089358 A1 | 6/2013 |
| WO | WO-2013093695 A1 | 6/2013 |
| WO | WO-2013098395 A1 | 7/2013 |
| WO | WO-2013098397 A2 | 7/2013 |
| WO | WO-2013116558 A1 | 8/2013 |
| WO | WO-2013116567 A1 | 8/2013 |
| WO | WO-2013147492 A1 | 10/2013 |
| WO | WO-2013155645 A1 | 10/2013 |
| WO | WO-2013155654 A1 | 10/2013 |
| WO | WO-2013159245 A1 | 10/2013 |
| WO | WO-2013171206 A1 | 11/2013 |
| WO | WO-2013190036 A1 | 12/2013 |
| WO | WO-2014008646 A1 | 1/2014 |
| WO | WO-2014012906 A1 | 1/2014 |
| WO | WO-2014039308 A1 | 3/2014 |
| WO | WO-2014114328 A1 | 7/2014 |
| WO | WO-2014138244 A1 | 9/2014 |
| WO | WO-2014139609 A2 | 9/2014 |
| WO | WO-2014139610 A1 | 9/2014 |
| WO | WO-2014150979 A2 | 9/2014 |
| WO | WO-2014151040 A2 | 9/2014 |
| WO | WO-2014153796 A1 | 10/2014 |
| WO | WO-2014159982 A1 | 10/2014 |
| WO | WO-2014205263 A1 | 12/2014 |
| WO | WO-2015027435 A1 | 3/2015 |
| WO | WO-2015028815 A1 | 3/2015 |
| WO | WO-2015052513 A2 | 4/2015 |
| WO | WO-2015054862 A1 | 4/2015 |
| WO | WO-2015073564 A1 | 5/2015 |
| WO | WO-2015077645 A1 | 5/2015 |
| WO | WO-2015078147 A1 | 6/2015 |
| WO | WO-2015082560 A1 | 6/2015 |
| WO | WO-2015013327 A3 | 7/2015 |
| WO | WO-2015114325 A1 | 8/2015 |
| WO | WO-2015144328 A1 | 10/2015 |
| WO | WO-2015149368 A1 | 10/2015 |
| WO | WO-2015165747 A1 | 11/2015 |
| WO | WO-2015172224 A1 | 11/2015 |
| WO | WO-2015186000 A2 | 12/2015 |
| WO | WO-2016059000 A1 | 4/2016 |
| WO | WO-2016092261 A1 | 6/2016 |

(56) References Cited

FOREIGN PATENT DOCUMENTS

| | | |
|---|---|---|
| WO | WO-2016112561 A1 | 7/2016 |
| WO | WO-2016210242 A1 | 12/2016 |
| WO | WO-2017001820 A1 | 1/2017 |
| WO | WO-2017130138 A1 | 8/2017 |
| WO | WO-2017139595 A1 | 8/2017 |
| WO | WO-2017139662 A1 | 8/2017 |
| WO | WO-2017173951 A1 | 10/2017 |

OTHER PUBLICATIONS

"Electronic Cigarette Refillable Cartridge GS-PUSH,Hold 1.5ml(Id:5722612) Product Details—View Electronic Cigarette Refillable Cartridge GS-PUSH,Hold 1.5ml from Green Sound High-Tech Co.,Ltd—EC21." EC21, Global B2B Marketplace—Connecting Global Buyers with Manufacturers, Suppliers, Exporters Worldwide, (2011), wo1138.en.ec21.com/Electronic_Cigarette_Refillable_Cartridge_GS—5366965_5722612.html.

"Esteam and J-Series Owner's Manual." Allbrands.com, 2002, www.allbrands.com/misc_files/pdfs/JiffySteamerOwnersManual.pdf.

"Hacking the Vuse Eig to Fully Use Cartridges and Allow Refills." Hacking the Vuse Eig to Fully Use Cartridges and Allow Refills, Oct. 16, 2015, se.azinstall.net/2015/10/hacking-vuse-eig-puffounter.html?m=1.

"Lenmar CB0104 Battery for Panasonic Cordless Phones." Amazon, Amazon, first reviewed Jan. 5, 2011, www.amazon.com/LenmarB0104-Battery-Panasonicordless/dp/B000BS6078/.

"New Tank Eigarette:innokin 510T." From China Manufacturer, Manufactory, Factory and Supplier on ECVV.com, Nov. 15, 2011, www.ecvv.com/product/3118191.html.

"Terminal and Splices Selection Guide." TE.com, TE, 2013, www.te.com/commerce/DocumentDelivery/DDEController?Action=srchrtrv&DocNm=2-1773700-5TerminalAndSplicesSelection&DocType=DS&DocLang=English&s_cid=1046.

"Uniden BT-990 Cordless Phone Battery NiD, 3.6 Volt, 800 MAh—Ultra Hiapacity—Replacement for Uniden BP-990, Toshiba, GE TL96550, TL96556, Panasonic HHR-P505 Rechargeable Batteries." Amazon, Amazon, first reviewed on Feb. 8, 2017, www.amazon.com/Uniden-BT-990ordless-Phone-Battery/dp/B01HDV75YW.

513official4. "Glade Plug-Ins Scented Oils 2001." YouTube, YouTube, Jun. 29, 2011, www.youtube.com/watch?v=zW9acp4NOK8.

CannabisReviewTV™. "Official: Cloud Vape Pen Review #CRTV420." YouTube, YouTube, Apr. 17, 2013, www.youtube.com/watch?v=oujMMZ6l_tA&has_verified=1.

Cedar Board by the home depot. earliest review dated Sep. 7, 2016. found online [Mar. 19, 2019] https://www.homedepot.com/p/1-in-x-4-in-x-8-ft-S1S2Eedar-Board-6-Pack-WRC148T6PK/300194383.

Chinabuye. "Innokin ITaste VV Tank Starter Kit Electronic Cigarette with Clearomizer." YouTube, YouTube, Jul. 23, 2013, www.youtube.com/watch?v=mz414d8MU20.

Cloud pen vaporizer unboxing review by vaporizer blog // VaporizerBlog.com, https://www.youtube.com/watch?v=ixHMkXoWKNg, published on Dec. 12, 2013.

Cutlerylover. "Eletronic Cigarette (Vaping) Review : HALO G6 Basic Starter Kit." YouTube, YouTube, Oct. 10, 2012, www.youtube.com/watch?v=kUprxsQUPCU.

Darth Vapor Reviews. "Halo Cigs: Triton Starter Kit Review." YouTube, YouTube, Aug. 11, 2013, www.youtube.com/watch?v=KkVzsGsDDMY.

Discount Office Supplies, Office Paper Products Legal Supplies, www.bulkofficesupply.com/Products/Baumgartens-Single-Hole-Trap-Door-Pencil-Sharpener-with-Eraser_BAU19550.aspx, retrieved Mar. 17, 2019.

El Mono Vapeador. "EVic Joyetech—Revision." YouTube, YouTube, Dec. 12, 2012, www.youtube.com/watch?v=WNLVfgwb4Gs.

Electronic Vaporization Device I JUUL I JUUL Vapor, posted at juulvapor.com <http://juulvapor.com>, posting date not given, © 2015 Juulvapor.com <http://Juulvapor.com> [online] [site visited Nov. 24, 2015]. Available from Internet, <https://www.juulvapor.com/shop-juul/>.

Engadget. Juul is the eig that will finally stop me from smoking (I hope). [online], published on Jun. 3, 2015. Available at: https://www.engadget.com/2015/06/03/pax-labs-juul-ecigarette/#/.

EnsembleIQ, "Vuse Product Reel," Youtube, Jun. 6, 2013, https://www.youtube.com/watch?v=Igo_b8Y8tNM.

Following the Vapor Trail, https://www.nytimes.com/2013/12/19/fashion/for-vaporizers-new-technologynd-product-design.html.

Fragrance, Purity. "Purity Home Fragrance—How to Refill Your Plug in Air Freshener.wmv." YouTube, YouTube, Jun. 4, 2012, www.youtube.com/watch?v=OreNgPBUwaY&t=66s.

Frakes, Dan. "Lightning: the IPhone's New Connector." Macworld, Macworld, Sep. 13, 2012, www.macworld.com/article/1168555/whatpples-new-lightningonnector-means-forou.html.

German Straight Razor box by rainbowebayauctions on ebay. dated May 11, 2012. found online [Mar. 22, 2019] https://www.bing.com/videos/search?q=straight+razor+cardboard+box&&view=detail&mid=4EFBC9664DDFEA73A2974EFBC9664DDFEA73A297&&FORM=VRDGAR.

Glory Vapes. "Glory Vapes TV: Kanger S1 Cubica Series Starter Kit Unboxing." YouTube, YouTube, Aug. 8, 2013, www.youtube.com/watch?v=NQjvJ6YhdbA.

Infocentre101. "Jiffy Steamer . . . No. 1 Seller." YouTube, YouTube, Dec. 31, 2011, www.youtube.com/watch?v=9ge8phdU6WY.

iWand Rectangular Pen Shape Design Flat Short Mouth Holder 1.0ML Tank Atomizer LED Display 800mAh Rechargeable E—Cigarette Set—COLORFUL, https://www.gearbest.com/electronicigarettes/pp_15466.html, accessed Jan. 25, 2019.

Joye eGo-Tank System XXL 1000mAh Starter Kit, https://www.myvaporstore.com/eGo-Tank-System-XXL-1000mAh-Starter-Kit-p/ego-t-xxlkit.htm, accessed Jan. 25, 2019.

Maiocco, Roberto. "Modello IWand." YouTube, YouTube, Dec. 28, 2012, www.youtube.com/watch?v=_brOOLDqHX0.

Making a box for my Straight Razor by Mr. Mars Experience. dated Jan 22, 2014. found online [Mar. 19, 2019] https://www.youtube.com/watch?v=Z7iAx2QoKD0.

Marino, Michelle. "Review—Glade PlugIns Scented Oil Fragrancers." YouTube, YouTube, Feb. 18, 2013, www.youtube.com/watch?v=lzEpGdwKSA4.

Pentel Multi 8 Color Lead Refill by Pentel on Amazon. earliest review dated Nov. 7, 2014. found online [Mar. 22, 2019] https://www.amazon.com/Pentel-Multi-Refill-VioletH2-V/dp/BooKQTBPCW/ref=sr_1_15?keywords=Pentel+Multi+8&qid=1558643586&s=gateway&sr=8-15.

Pierce, D. This Might Just Be the First Great Eig. {online} WIRED, Published on Apr. 21, 2015. Available at: https://www.wired.com/2015/04/pax-juul-ecig/?mbid=social_twitter.

Prater, Bill. "Crown Seven Hydro Imperial Menthol Review." YouTube, YouTube, Jan. 12, 2013, www.youtube.com/watch?v=YTcf6mEa0.

Press Release by R.J. Reynolds, "https://www.reynoldsamerican.com/abouts/press-releases/Press-Release-Details-/2013/RJ-Reynolds-Vaporompany-bringing-VUSE-Digital-Vaporigarette-toolorado-/default.aspx".

Purity Home Fragrance—How to refill your plug in air freshener.wmv, https://www.youtube.com/watch?v=OreNgPBUwaY&t=66s , Jun. 4, 2012.

Rose Plastic. Rose Plastic: Innovations in Plastic Packaging, www.rose-plastic./2030.0.html?&L=4p?id=2337id=2345iel25% worldwide unique plastic packaging with remarkable diversity, retrieved Mar. 17, 2019.

Ruyanchina. "RUYAN-The New Way to Smoke(English) Eigarette-Blog.com." YouTube, YouTube, Jun. 9, 2007, www.youtube.com/watch?v=ia2997x_kog.

Smith, Chris. "Next USB Connector Will Finally Be Reversible, like Apple's Lightning Plug." BGR, Dec. 5, 2013, BGR.com/2013/12/05/reversiblesbonnectorpple-lightning/.

SourDieselManCO. "0.pen Vape Pen Vaporizer Hybrid and Indica 250mg Cartridges." YouTube, YouTube, Apr. 8, 2013, www.youtube.com/watch?v=5_jWTQVQbEw.

(56) References Cited

OTHER PUBLICATIONS

TechVitaminsTV. "Eigarettes: How It Works (Blu Premium Eig Social Kit Review) Must See!!" YouTube, YouTube, Mar. 14, 2012, www.youtube.com/watch?v=mFAYxw6csjg.
The Verge. Startup behind the Lambo of vaporizers just launched an intelligent eigarette. [online], published on Apr. 21, 2015. Available at: https://www.theverge.com/2015/4/21/8458629/pax-labs-eigarette-juul.
Uptoyou Fromeme. "Elips Ego Sole Electronic Cigarette Kit Patent Elipse Flat Upgrade F6 Section with Atomizer CE4." YouTube, YouTube, Sep. 12, 2013, www.youtube.com/watch?v=cnPcgDzFm0Q.
VapeandBake. "NJOY Electronic Cigarette Review." YouTube, YouTube, Apr. 9, 2013, www.youtube.com/watch?v=qUynQFK_Xpo.
Vaporizers Reviewed. "AtmosRX Optimus 510 Vaporizer Review." YouTube, YouTube, Oct. 10, 2013, www.youtube.com/watch?v=wsyQncG8FB8.
Vaporizers Reviewed. "MicroG Pen Vaporizer Review." YouTube, YouTube, Nov. 6, 2013, www.youtube.com/watch?v=pLhtL8vosrs.
VapXtream. "The Elips by LSK." YouTube, YouTube, Jan. 13, 2013, www.youtube.com/watch?v=PTfJ1srfqWI.
Walnut and cocobolo razor coffin pics by scrapcan. dated Aug. 9, 2010. found online [Mar. 20, 2019] https://sharprazorpalace.com/show-te11/57238-walnutocobolo-razoroffin-pics.html.
Wholesale Consumer electronics. "Elips Ego SOLE Electronic Cigarette Kit Patent Eigarette Eig Elipse Flat Upgrade F6 Section." YouTube, YouTube, Sep. 13, 2013, www.youtube.com/watch?v=iCeE-O1scDg.
WSP Traditional Straight Razor Coffin by WSP. earliest review dated Jul. 7, 2015. found online [Mar. 18, 2019] https://www.amazon.com/WSP-Traditional-Straight-Razoroffin/dp/B00FL2R4BA/ref=sr_1_fkmrnull_3?keywords=WSP+Traditional+Straight+razor+coffin&qid=1558643115&s=gateway&sr=8-3-fkmrnull.
U.S. Appl. No. 15/430,357, filed Feb. 10, 2017, US20170231282.
U.S. Appl. No. 35/001,170, filed Jul. 28, 2016, D. 842536
U.S. Appl. No. 16/077,731, filed Feb. 10, 2017, US20190104767.
U.S. Appl. No. 35/001,169, filed Jul. 28, 2016. D. 825102
U.S. Appl. No. 29/650,601, filed Jun. 7, 2018, D. 861975.
U.S. Appl. No. 29/707,225, filed Sep. 26, 2019.
U.S. Appl. No. 29/499,016, filed Oct. 13, 2015.
U.S. Appl. No. 29/542,362, filed Aug. 11, 2014.
U.S. Appl. No. 29/499,018, filed Aug. 11, 2014.
U.S. Appl. No. 29/499,021, filed Dec. 27, 2018.
U.S. Appl. No. 29/674,910, filed Aug. 11, 2014.
U.S. Appl. No. 29/499,025, filed Dec. 1, 2017, D. 744419.
U.S. Appl. No. 29/628,194, filed Aug. 31, 2018.
U.S. Appl. No. 29/661,968, filed Aug. 31, 2018, D. 858868.
U.S. Appl. No. 29/661,973, filed Aug. 31, 2018, D. 858869.
U.S. Appl. No. 29/662,037, filed Aug. 31, 2018, D. 858,870.
U.S. Appl. No. 29/662,038, filed Aug. 29, 2019.
U.S. Appl. No. 29/703,845, filed Oct. 13, 2015.
U.S. Appl. No. 14/581,666, filed Dec. 23, 2015, U.S. Pat. No. 10,058,124.
U.S. Appl. No. 15/379,898, filed Dec. 15, 2016, U.S. 10,058,129.
U.S. Appl. No. 15/813,084, filed Nov. 14, 2017, US20180064174.
U.S. Appl. No. 15/813,096, filed Nov. 14, 2017, U.S. Pat. No. 10,117,465.
U.S. Appl. No. 15/832,743, filed Dec. 5, 2017, US20180098578.
U.S. Appl. No. 15/833,873, filed Dec. 6, 2017, U.S. Pat. No. 10,111,470.
U.S. Appl. No. 16/032,009, filed Jul. 10, 2018, US20180317557.
Uptoyou Fromeme. "F8 iWand Penstyle Adjustable Voltage Itaste VV Power Display Electronic Cigarette." YouTube Sep. 25, 2013. www.youtube.com/watch?v=5nqtHWJvWWo.
U.S. Appl. No. 14/581,66, filed Dec. 23, 2014, U.S. Pat. No. 10,058,124.
U.S. Appl. No. 15/257,748, filed Sep. 6, 2016, U.S. Pat. No. 10,159,282.
U.S. Appl. No. 15/257,760, filed Sep. 6, 2016, U.S. Pat. No. 10,076,139.
U.S. Appl. No. 15/257,768, filed Sep. 6, 2016, US 2016-0366947.
U.S. Appl. No. 15/379,898, filed Dec. 15, 2016, U.S. Pat. No. 10,058,129.
U.S. Appl. No. 15/813,084, filed Nov. 14, 2017, U.S. Pat. No. 10,701,975.
U.S. Appl. No. 15/813,089, filed Nov. 14, 2017, U.S. Pat. No. 10,058,130.
U.S. Appl. No. 15/815,641, filed Nov. 16, 2017, U.S. Pat. No. 10,045,567.
U.S. Appl. No. 15/813,096, Nov. 14, 2017, U.S. Pat. No. 10,117,465.
U.S. Appl. No. 15/820,361, filed Nov. 21, 2017, US 2018-0070648.
U.S. Appl. No. 15/815,645, filed Nov. 16, 2017, U.S. Pat. No. 10,117,466.
U.S. Appl. No. 15/815,643, filed Nov. 16, 2017, U.S. Pat. No. 10,201,190.
U.S. Appl. No. 15/832,719, filed Dec. 5, 2017, US 2018-0092405.
U.S. Appl. No. 15/820,354, filed Nov. 21, 2017, U.S. Pat. No. 10/264,823.
U.S. Appl. No. 15/815,666, filed Nov. 16, 2017, U.S. Pat. No. 10,104,915.
U.S. Appl. No. 15/820,370, filed Nov. 21, 2017, U.S. Pat. No. 10,070,669.
U.S. Appl. No. 15/832,743, filed Dec. 5, 2017, U.S. Pat. No. 10,667,560.
U.S. Appl. No. 15/832,749, filed Dec. 5, 2017, U.S. Pat. No. 10,045,568.
U.S. Appl. No. 15/832,731, filed Dec. 5, 2017, US 2018-0092406.
U.S. Appl. No. 15/833,873, filed Dec. 6, 2017, U.S. Appl. No. 10,111,470.
U.S. Appl. No. 16/032,009, filed Jul. 10, 2018, U.S. Pat. No. 10,709,173.
U.S. Appl. No. 16/114,201, filed Aug. 27, 2018, US 2019-0000148.
U.S. Appl. No. 16/114,204, filed Aug. 27, 2018, US 2019-0008212.
U.S. Appl. No. 16/114,206, filed Aug. 27, 2018, US 2018-0360129.
U.S. Appl. No. 15/430,284, filed Feb. 10, 2017, U.S. Pat. No. 10,279,934.
U.S. Appl. No. 16/404,693, filed May 6, 2019, US 2019-0256231.
U.S. Appl. No. 15/430,317, filed Feb. 10, 2017, U.S. Pat. No. 10,130,123.
U.S. Pat. No. 16/077,731, filed Feb. 10, 2017, US 2019-004767.
U.S. Appl. No. 15/430,357, filed Feb. 10, 2017, U.S. Pat. No. 10,638,792.
U.S. Appl. No. 16/864,007, filed Apr. 30, 2020, US 2020-0260785.
U.S. Appl. No. 15/053,927, filed Feb. 25, 2016, U.S. Pat. No, 9,549,573.
U.S. Appl. No. 16/080,296, filed Feb. 27, 2017, US 2019-0069599.

* cited by examiner

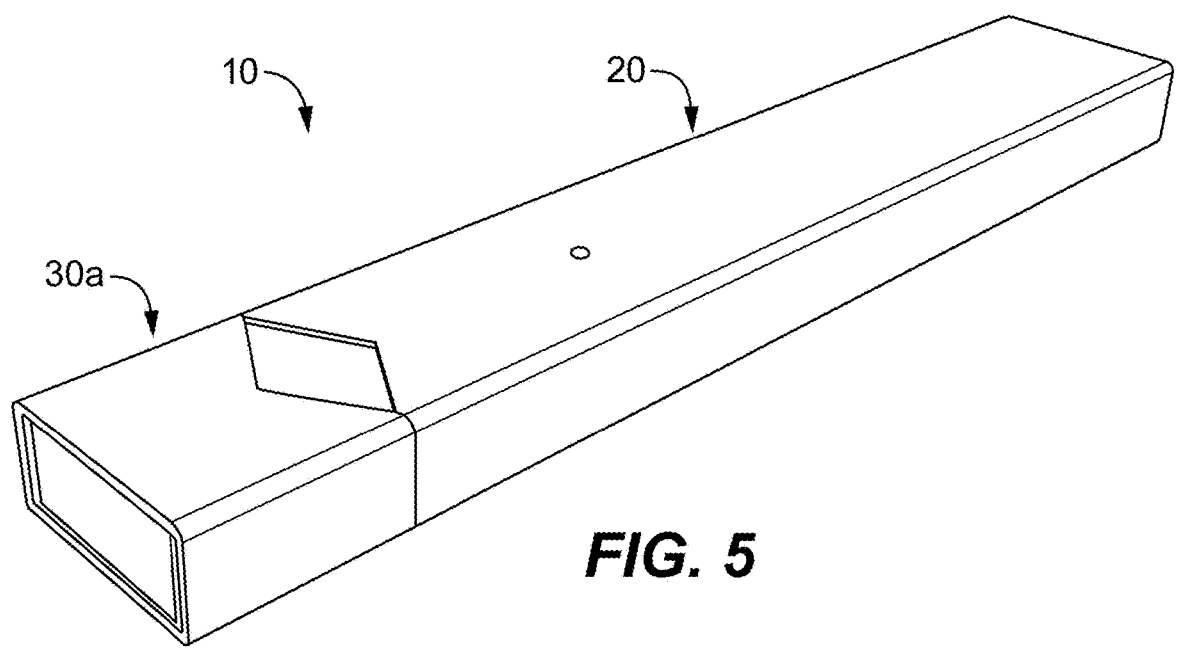
FIG. 5
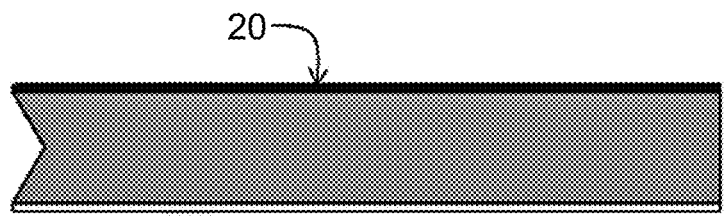
FIG. 6A
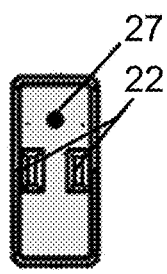
FIG. 6C
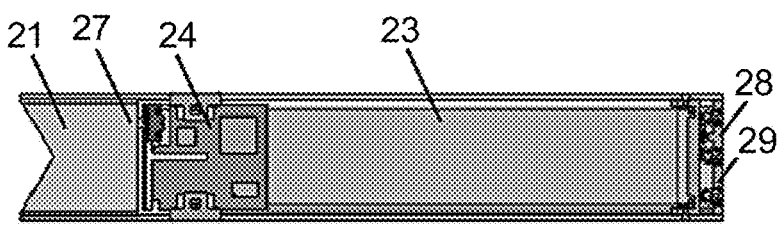
FIG. 6B
FIG. 6D
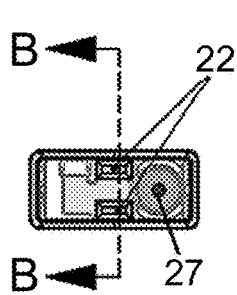
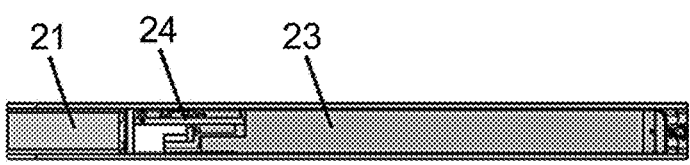
Section B-B

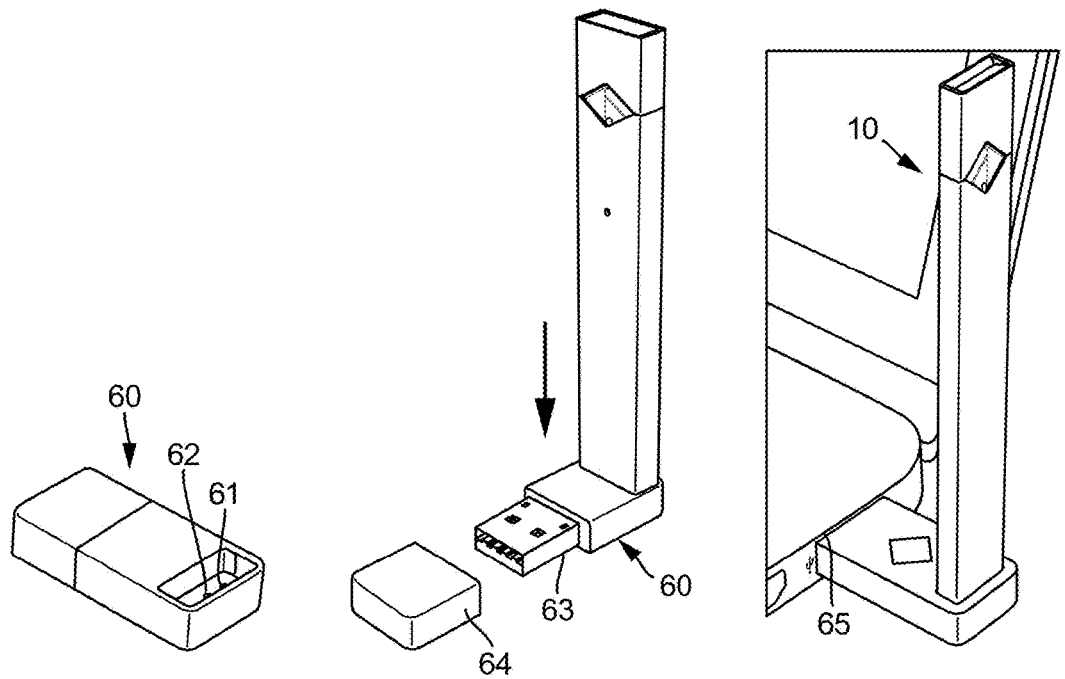
FIG. 16A  FIG. 16B  FIG. 16C
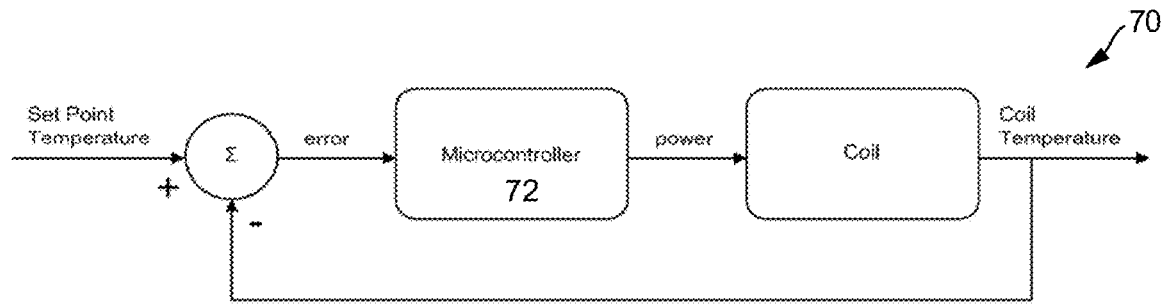
FIG. 17A
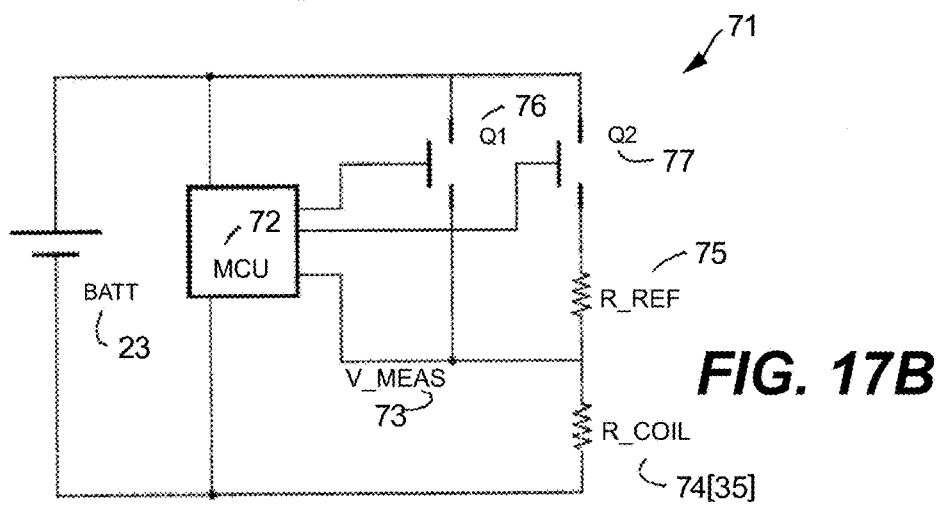
FIG. 17B

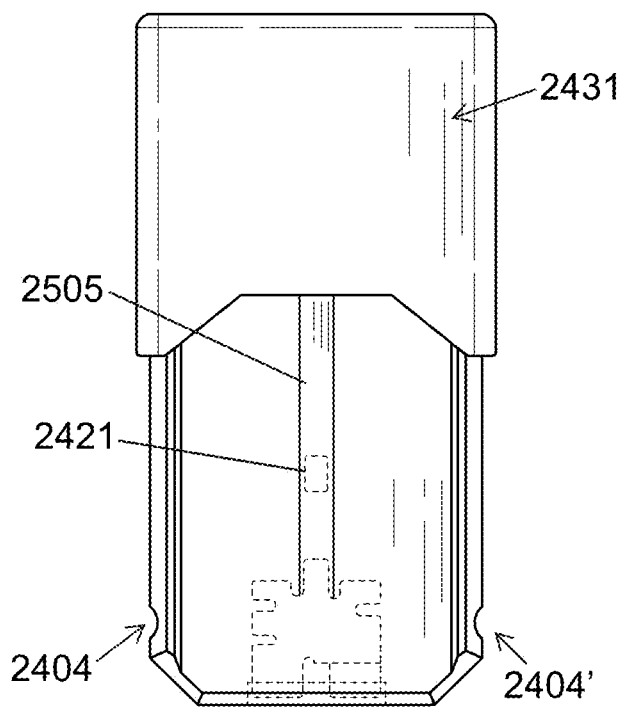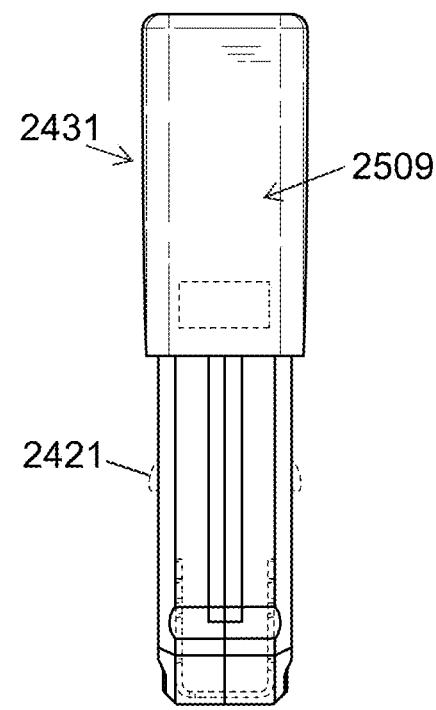
FIG. 25A   FIG. 25B
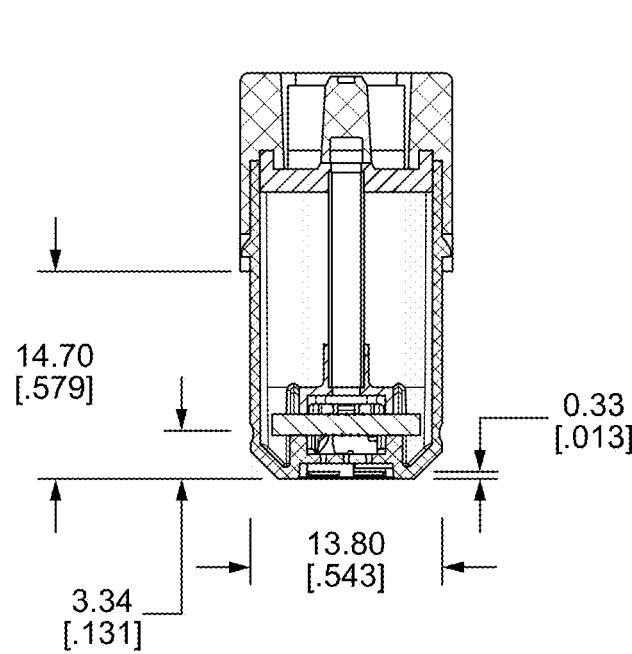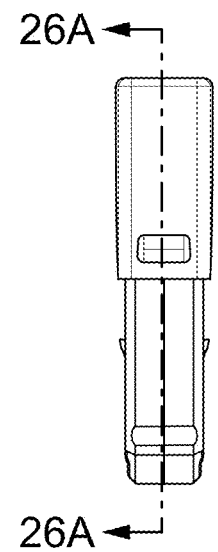
FIG. 26A   FIG. 26B

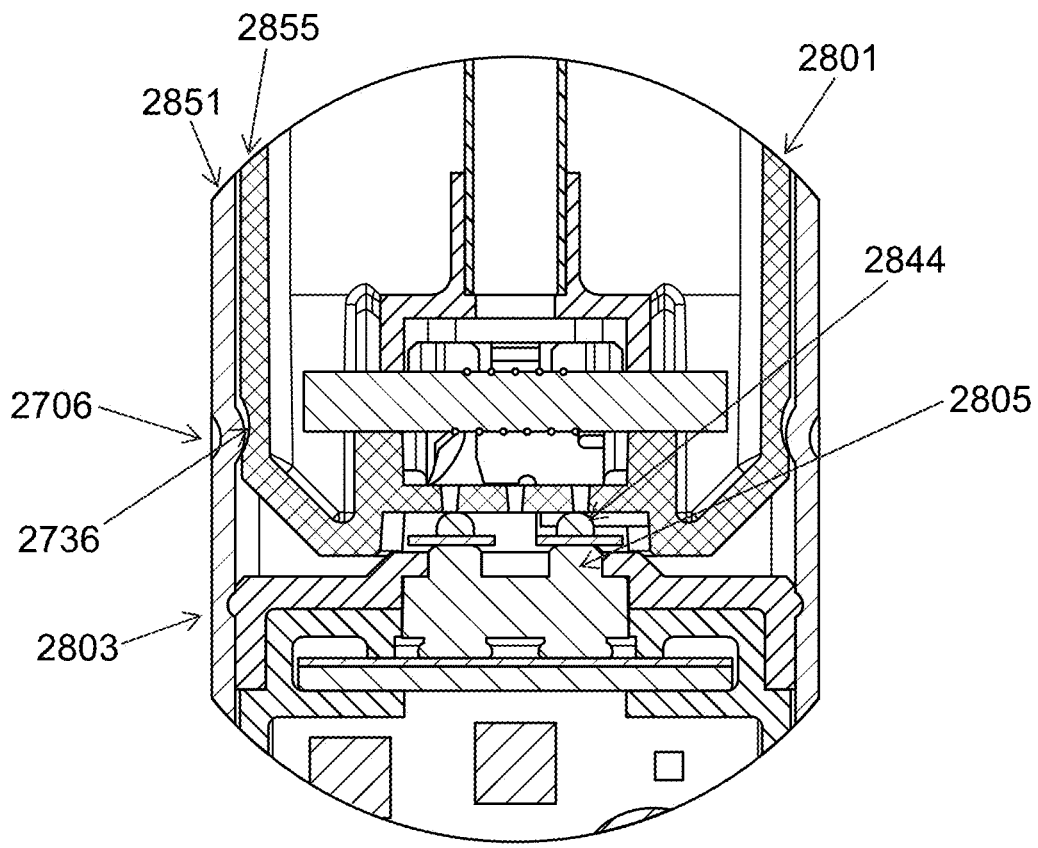
FIG. 28D
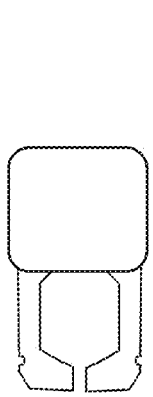 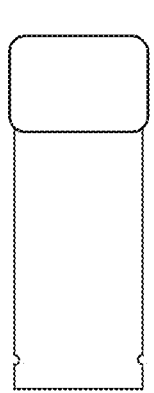 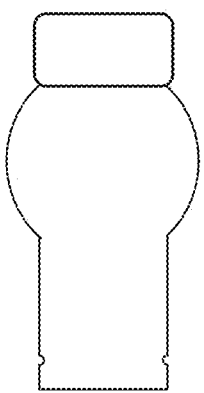 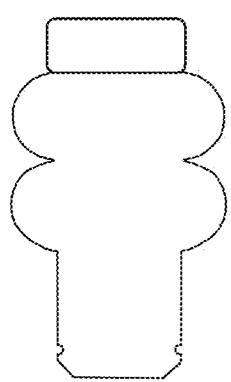
FIG. 29A     FIG. 29B     FIG. 29C     FIG. 29D

VAPORIZATION DEVICE SYSTEMS AND METHODS

CROSS REFERENCE TO RELATED APPLICATIONS

This patent application is a continuation of U.S. patent application Ser. No. 15/379,898, filed Dec. 15, 2016 and entitled "VAPORIZATION DEVICE SYSTEMS AND METHODS," which claims priority to U.S. Provisional Patent Application No. 62/294,281, filed Feb. 11, 2016 and entitled "SECURELY ATTACHING CARTRIDGES FOR VAPORIZER DEVICES," and is a continuation-in-part of U.S. patent application Ser. No. 15/053,927, filed on Feb. 25, 2016 and entitled "VAPORIZATION DEVICE SYSTEMS AND METHODS," which is a continuation-in-part of U.S. patent application Ser. No. 14/581,666, filed on Dec. 23, 2014 and entitled "VAPORIZATION DEVICE SYSTEMS AND METHODS," which claims priority to U.S. Provisional Patent Application No. 61/936,593, filed on Feb. 6, 2014, and U.S. Provisional Patent Application No. 61/937,755, filed on Feb. 10, 2014.

The disclosures of each of the patent applications noted above are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Electronic inhalable aerosol devices (e.g., vaporization devices, electronic vaping devices, etc.) and particularly electronic aerosol devices, typically utilize a vaporizable material that is vaporized to create an aerosol vapor capable of delivering an active ingredient to a user. Control of the temperature of the resistive heater must be maintained (e.g., as part of a control loop), and this control may be based on the resistance of the resistive heating element.

Many of the battery-powered vaporizers described to date include a reusable batter-containing device portion that connects to one or more cartridges containing the consumable vaporizable material. As the cartridges are used up, they are removed and replaced with fresh ones. It may be particularly useful to have the cartridge be integrated with a mouthpiece that the user can draw on to receive vapor. However, a number of surprising disadvantages may result in this configuration, particular to non-cylindrical shapes. For example, the use of a cartridge at the proximal end of the device, which is also held by the user's mouth, particularly where the cartridge is held in the vaporizer device by a friction- or a snap-fit, may result in instability in the electrical contacts, particularly with cartridges of greater than 1 cm length.

Described herein are apparatuses and methods that may address the issues discussed above.

SUMMARY OF THE DISCLOSURE

The present invention relates generally to apparatuses, including systems and devices, for vaporizing material to form an inhalable aerosol. Specifically, these apparatuses may include vaporizers.

In particular, described herein are cartridges that are configured for use with a vaporizer (e.g., vaporizer device) having a rechargeable power supply that includes a proximal cartridge-receiving opening. These cartridges are specifically adapted to be releasably but securely held within the cartridge-receiving opening of the vaporizer and resist disruption of the electrical contact with the controller and power supply in the vaporizer even when held by the user's mouth.

For example, described herein are cartridge devices holding a vaporizable material for securely coupling with an electronic inhalable aerosol device. A device may include: a mouthpiece; a fluid storage compartment holding a vaporizable material; a base configured to fit into a rectangular opening that is between 13-14 mm deep, 4.5-5.5 mm wide, and 13-14 mm long, the base having a bottom surface comprising a first electrical contact and a second electrical contact, a first locking gap on a first lateral surface of the base, and a second locking gap on a second lateral surface of the base that is opposite first lateral surface.

A cartridge device holding a vaporizable material for securely coupling with an electronic inhalable aerosol device may include: a mouthpiece; a fluid storage compartment holding a vaporizable material; a base configured to fit into a rectangular opening that is between 13-14 mm deep, 4.5-5.5 mm wide, and 13-14 mm long, the base having a length of at least 10 mm, and a bottom surface comprising a first electrical contact and a second electrical contact, a first locking gap on a first lateral surface of the base positioned between 3-4 mm above the bottom surface, and a second locking gap on a second lateral surface of the base that is opposite first lateral surface.

A cartridge device holding a vaporizable material for securely coupling with an electronic inhalable aerosol device, the device comprising: a mouthpiece; a fluid storage compartment holding a vaporizable material; a rectangular base having a pair of minor sides that are between greater than 10 mm deep and between 4.5-5.5 mm wide, and a pair of major sides that are greater than 10 mm deep and between 13-14 mm wide, a bottom surface comprising a first electrical contact and a second electrical contact, and a first locking gap on a first lateral surface of the base positioned between 3-4 mm above the bottom surface, and a second locking gap on a second lateral surface of the base that is opposite first lateral surface. Any of these devices may also typically include a wick in fluid communication with the vaporizable material; and a resistive heating element in fluid contact with the wick and in electrical contact with the first and second electrical contacts.

In general, applicants have found that, for cartridges having a base that fits into the rectangular opening of a vaporizer (particularly one that is between 13-14 mm deep, 4.5-5.5 mm wide, and 13-14 mm long), the it is beneficial to have a length of the base (which is generally the connection region of the base for interfacing into the rectangular opening) that is greater than 10 mm, however when the base is greater than 10 mm (e.g., greater than 11 mm, greater than 12 mm, greater than 13 mm), the stability of the cartridge and in particular the electrical contacts, may be greatly enhanced if the cartridge includes one or more (e.g., two) locking gaps near the bottom surface of the cartridge into which a complimentary detent on the vaporizer can couple to. In particular, it may be beneficial to have the first and second locking gaps within 6 mm of the bottom surface, and more specifically within 3-4 mm of the bottom surface. The first and second lateral surfaces may be separated from each other by between 13-14 mm, e.g., they may be on the short sides of a cartridge base having a rectangular cross-section (a rectangular base).

As mentioned, any of these cartridges may include a wick extending through the fluid storage compartment and into the vaporizable material, a resistive heating element in contact with the first and second electrical contacts, and a heating chamber in electrical contact with the first and second electrical contacts.

It may also be beneficial to include one or more (e.g., two) detents extending from a major surface (e.g., two major surfaces) of the base, such as from a third and/or fourth lateral wall of the base.

The cartridge may include any appropriate vaporizable material, such as a nicotine salt solution.

In general, the mouthpiece may be attached opposite from the base. The fluid storage compartment may also comprises an air path extending there through (e.g., a cannula or tube). In some variations at least part of the fluid storage compartment may be within the base. The compartment may be transparent (e.g., made from a plastic or polymeric material that is clear) or opaque, allowing the user to see how much fluid is left.

In general, the locking gap(s) may be a channel in the first lateral surface (e.g., a channel transversely across the first lateral surface parallel to the bottom surface), an opening or hole in the first lateral surface, and/or a hole in the first lateral surface. The locking gap is generally a gap that is surrounded at least on the upper and lower (proximal and distal) sides by the lateral wall to allow the detent on the vaporizer to engage therewith.

The locking gap may be generally between 0.1 mm and 2 mm wide (e.g., between a lower value of about 0.1, 0.2, 0.3, 0.4, 0.5, 0.6, 0.7, 0.8, 0.9, 1.0, 1.1, 1.2, 1.3, 1.4, etc. and an upper value of about 0.4, 0.5, 0.6, 0.7, 0.8, 0.9, 1.0, 1.1, 1.2, 1.3, 1.4, 1.5, 1.6, 1.7, 1.8, 1.9, 2.0, etc., where the upper value is always greater than the lower value).

Also described are vaporizers and method of using them with cartridges, including those described herein.

In some variations, the apparatuses described herein may include an inhalable aerosol comprising: an oven comprising an oven chamber and a heater for heating a vapor forming medium in the oven chamber to generate a vapor; a condenser comprising a condensation chamber in which at least a fraction of the vapor condenses to form the inhalable aerosol; an air inlet that originates a first airflow path that includes the oven chamber; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber to a user.

The oven may be within a body of the device. The device may further comprise a mouthpiece, wherein the mouthpiece comprises at least one of the air inlet, the aeration vent, and the condenser. The mouthpiece may be separable from the oven. The mouthpiece may be integral to a body of the device, wherein the body comprises the oven. The device may further comprise a body that comprises the oven, the condenser, the air inlet, and the aeration vent. The mouthpiece may be separable from the body.

In some variations, the oven chamber may comprise an oven chamber inlet and an oven chamber outlet, and the oven further comprises a first valve at the oven chamber inlet, and a second valve at the oven chamber outlet. The aeration vent may comprise a third valve. The first valve, or said second valve may be chosen from the group of a check valve, a clack valve, a non-return valve, and a one-way valve. The third valve may be chosen from the group of a check valve, a clack valve, a non-return valve, and a one-way valve. The first or second valve may be mechanically actuated. The first or second valve may be electronically actuated. The first valve or second valve may be manually actuated. The third valve may be mechanically actuated. The third valve may be mechanically actuated. The third valve may be electronically actuated. The third valve may be manually actuated.

In some variations, the device may further comprise a body that comprises at least one of: a power source, a printed circuit board, a switch, and a temperature regulator. The device may further comprise a temperature regulator in communication with a temperature sensor. The temperature sensor may be the heater. The power source may be rechargeable. The power source may be removable. The oven may further comprise an access lid. The vapor forming medium may comprise tobacco. The vapor forming medium may comprise a botanical. The vapor forming medium may be heated in the oven chamber wherein the vapor forming medium may comprise a humectant to produce the vapor, wherein the vapor comprises a gas phase humectant. The vapor may be mixed in the condensation chamber with air from the aeration vent to produce the inhalable aerosol comprising particle diameters of average size of about 1 micron. The vapor forming medium may be heated in the oven chamber, wherein the vapor is mixed in the condensation chamber with air from the aeration vent to produce the inhalable aerosol comprising particle diameters of average size of less than or equal to 0.9 micron. The vapor forming medium may be heated in the oven chamber, wherein the vapor is mixed in the condensation chamber with air from the aeration vent to produce the inhalable aerosol comprising particle diameters of average size of less than or equal to 0.8 micron. The vapor forming medium may be heated in the oven chamber, wherein the vapor is mixed in the condensation chamber with air from the aeration vent to produce the inhalable aerosol comprising particle diameters of average size of less than or equal to 0.7 micron. The vapor forming medium may be heated in the oven chamber, wherein the vapor is mixed in the condensation chamber with air from the aeration vent to produce the inhalable aerosol comprising particle diameters of average size of less than or equal to 0.6 micron. The vapor forming medium may be heated in the oven chamber, wherein the vapor is mixed in the condensation chamber with air from the aeration vent to produce the inhalable aerosol comprising particle diameters of average size of less than or equal to 0.5 micron.

In some variations, the humectant may comprise glycerol as a vapor-forming medium. The humectant may comprise vegetable glycerol. The humectant may comprise propylene glycol. The humectant may comprise a ratio of vegetable glycerol to propylene glycol. The ratio may be about 100:0 vegetable glycerol to propylene glycol. The ratio may be about 90:10 vegetable glycerol to propylene glycol. The ratio may be about 80:20 vegetable glycerol to propylene glycol. The ratio may be about 70:30 vegetable glycerol to propylene glycol. The ratio may be about 60:40 vegetable glycerol to propylene glycol. The ratio may be about 50:50 vegetable glycerol to propylene glycol. The humectant may comprise a flavorant. The vapor forming medium may be heated to its pyrolytic temperature. The vapor forming medium may heated to 200° C. at most. The vapor forming medium may be heated to 160° C. at most. The inhalable aerosol may be cooled to a temperature of about 50°-70° C. at most, before exiting the aerosol outlet of the mouthpiece.

Also described herein are methods for generating an inhalable aerosol. Such a method may comprise: providing an inhalable aerosol generating device wherein the device comprises: an oven comprising an oven chamber and a heater for heating a vapor forming medium in the oven chamber and for forming a vapor therein; a condenser comprising a condensation chamber in which the vapor forms the inhalable aerosol; an air inlet that originates a first airflow path that includes the oven chamber; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber to a user.

The oven may be within a body of the device. The device may further comprise a mouthpiece, wherein the mouthpiece comprises at least one of the air inlet, the aeration vent, and the condenser. The mouthpiece may be separable from the oven. The mouthpiece may be integral to a body of the device, wherein the body comprises the oven. The method may further comprise a body that comprises the oven, the condenser, the air inlet, and the aeration vent. The mouthpiece may be separable from the body.

The oven chamber may comprise an oven chamber inlet and an oven chamber outlet, and the oven further comprises a first valve at the oven chamber inlet, and a second valve at the oven chamber outlet.

The vapor forming medium may comprise tobacco. The vapor forming medium may comprise a botanical. The vapor forming medium may be heated in the oven chamber wherein the vapor forming medium may comprise a humectant to produce the vapor, wherein the vapor comprises a gas phase humectant. The vapor may comprise particle diameters of average mass of about 1 micron. The vapor may comprise particle diameters of average mass of about 0.9 micron. The vapor may comprise particle diameters of average mass of about 0.8 micron. The vapor may comprise particle diameters of average mass of about 0.7 micron. The vapor may comprise particle diameters of average mass of about 0.6 micron. The vapor may comprise particle diameters of average mass of about 0.5 micron.

In some variations, the humectant may comprise glycerol as a vapor-forming medium. The humectant may comprise vegetable glycerol. The humectant may comprise propylene glycol. The humectant may comprise a ratio of vegetable glycerol to propylene glycol. The ratio may be about 100:0 vegetable glycerol to propylene glycol. The ratio may be about 90:10 vegetable glycerol to propylene glycol. The ratio may be about 80:20 vegetable glycerol to propylene glycol. The ratio may be about 70:30 vegetable glycerol to propylene glycol. The ratio may be about 60:40 vegetable glycerol to propylene glycol. The ratio may be about 50:50 vegetable glycerol to propylene glycol. The humectant may comprise a flavorant. The vapor forming medium may be heated to its pyrolytic temperature. The vapor forming medium may heated to 200° C. at most. The vapor forming medium may be heated to 160° C. at most. The inhalable aerosol may be cooled to a temperature of about 50°-70° C. at most, before exiting the aerosol outlet of the mouthpiece.

The device may be user serviceable. The device may not be user serviceable.

A method for generating an inhalable aerosol may include: providing a vaporization device, wherein said device produces a vapor comprising particle diameters of average mass of about 1 micron or less, wherein said vapor is formed by heating a vapor forming medium in an oven chamber to a first temperature below the pyrolytic temperature of said vapor forming medium, and cooling said vapor in a condensation chamber to a second temperature below the first temperature, before exiting an aerosol outlet of said device.

A method of manufacturing a device for generating an inhalable aerosol may include: providing said device comprising a mouthpiece comprising an aerosol outlet at a first end of the device; an oven comprising an oven chamber and a heater for heating a vapor forming medium in the oven chamber and for forming a vapor therein, a condenser comprising a condensation chamber in which the vapor forms the inhalable aerosol, an air inlet that originates a first airflow path that includes the oven chamber and then the condensation chamber, an aeration vent that originates a second airflow path that joins the first airflow path prior to or within the condensation chamber after the vapor is formed in the oven chamber, wherein the joined first airflow path and second airflow path are configured to deliver the inhalable aerosol formed in the condensation chamber through the aerosol outlet of the mouthpiece to a user.

The method may further comprise providing the device comprising a power source or battery, a printed circuit board, a temperature regulator or operational switches.

A device for generating an inhalable aerosol may comprise a mouthpiece comprising an aerosol outlet at a first end of the device and an air inlet that originates a first airflow path; an oven comprising an oven chamber that is in the first airflow path and includes the oven chamber and a heater for heating a vapor forming medium in the oven chamber and for forming a vapor therein; a condenser comprising a condensation chamber in which the vapor forms the inhalable aerosol; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber through the aerosol outlet of the mouthpiece to a user.

Also described herein are vaporization devices and methods of operating them. In particular, described herein are methods for controlling the temperature of a resistive heater (e.g., resistive heating element) by controlling the power applied to a resistive heater of a vaporization device by measuring the resistance of the resistive heater at discrete intervals before (e.g., baseline or ambient temperature) and during vaporization (e.g., during heating to vaporize a material within the device). Changes in the resistance during heating may be linearly related to the temperature of the resistive heater over the operational range, and therefore may be used to control the power applied to heat the resistive heater during operation. Also described herein are vaporization devices that are configured to measure the resistance of the resistive heater during heating (e.g., during a pause in the application of power to heat the resistive heater) and to control the application of power to the resistive heater based on the resistance values.

In general, in any of the methods and apparatuses described herein, the control circuitry (which may include one or more circuits, a microcontroller, and/or control logic) may compare a resistance of the resistive heater during heating, e.g., following a sensor input indicating that a user wishes to withdraw vapor, to a target resistance of the heating element. The target resistance is typically the resistance of the resistive heater at a desired (and in some cases estimated) target vaporization temperature. The apparatus and methods may be configured to offer multiple and/or adjustable vaporization temperatures.

In some variations, the target resistance is an approximation or estimate of the resistance of the resistive heater when the resistive heater is heated to the target temperature (or temperature ranges). In some variations, the target reference is based on a baseline resistance for the resistive heater and/or the percent change in resistance from baseline resistance for the resistive heater at a target temperature. In general, the baseline resistance may be referred to as the resistance of the resistive heater at an ambient temperature.

For example, a method of controlling a vaporization device may include: placing a vaporizable material in thermal contact with a resistive heater; applying power to the resistive heater to heat the vaporizable material; measuring the resistance of the resistive heater; and adjusting the applied power to the resistive heater based on the difference between the resistance of the resistive heater and a target resistance of the heating element.

In some variations, the target resistance is based on a reference resistance. For example, the reference resistance may be approximately the resistance of the coil at target temperature. This reference resistance may be calculated, estimated or approximated (as described herein) or it may be determined empirically based on the resistance values of the resistive heater at one or more target temperatures.

In some variations, the target resistance is based on the resistance of the resistive heater at an ambient temperature. For example, the target resistance may be estimated based on the electrical properties of the resistive heater, e.g., the temperature coefficient of resistance or TCR, of the resistive heater (e.g., "resistive heating element" or "vaporizing element").

For example, a vaporization device (e.g., an electronic vaporizer device) may include a puff sensor, a power source (e.g., battery, capacitor, etc.), a heating element controller (e.g., microcontroller), and a resistive heater. A separate temperature sensor may also be included to determine an actual temperature of ambient temperature and/or the resistive heater, or a temperature sensor may be part of the heating element controller. However, in general, the microcontroller may control the temperature of the resistive heater (e.g., resistive coil, etc.) based on a change in resistance due to temperature (e.g., TCR).

In general, the heater may be any appropriate resistive heater, such as a resistive coil. The heater is typically coupled to the heater controller so that the heater controller applies power (e.g., from the power source) to the heater. The heater controller may include regulatory control logic to regulate the temperature of the heater by adjusting the applied power. The heater controller may include a dedicated or general-purpose processor, circuitry, or the like and is generally connected to the power source and may receive input from the power source to regulate the applied power to the heater.

For example, any of these apparatuses may include logic for determining the temperature of the heater based on the TCR. The resistance of the heater (e.g., a resistive heater) may be measured ($R_{heater}$) during operation of the apparatus and compared to a target resistance, which is typically the resistance of the resistive heater at the target temperature. In some cases this resistance may be estimated from the the resistance of the resistive hearing element at ambient temperature (baseline).

In some variations, a reference resistor ($R_{reference}$) may be used to set the target resistance. The ratio of the heater resistance to the reference resistance ($R_{heater}/R_{reference}$) is linearly related to the temperature (above room temp) of the heater, and may be directly converted to a calibrated temperature. For example, a change in temperature of the heater relative to room temperature may be calculated using an expression such as $(R_{heater}/R_{reference}-1)*(1/TCR)$, where TCR is the temperature coefficient of resistivity for the heater. In one example, TCR for a particular device heater is $0.00014/°$ C. In determining the partial doses and doses described herein, the temperature value used (e.g., the temperature of the vaporizable material during a dose interval, $T_i$, described in more detail below) may refer to the unitless resistive ratio (e.g., $R_{heater}/R_{reference}$) or it may refer to the normalized/corrected temperature (e.g., in ° C.).

When controlling a vaporization device by comparing a measure resistance of a resistive heater to a target resistance, the target resistance may be initially calculated and may be factory preset and/or calibrated by a user-initiated event. For example, the target resistance of the resistive heater during operation of the apparatus may be set by the percent change in baseline resistance plus the baseline resistance of the resistive heater, as will be described in more detail below. As mentioned, the resistance of the heating element at ambient is the baseline resistance. For example, the target resistance may be based on the resistance of the resistive heater at an ambient temperature and a target change in temperature of the resistive heater.

As mentioned above, the target resistance of the resistive heater may be based on a target heating element temperature. Any of the apparatuses and methods for using them herein may include determining the target resistance of the resistive heater based on a resistance of the resistive heater at ambient temperature and a percent change in a resistance of the resistive heater at an ambient temperature.

In any of the methods and apparatuses described herein, the resistance of the resistive heater may be measured (using a resistive measurement circuit) and compared to a target resistance by using a voltage divider. Alternatively or additionally any of the methods and apparatuses described herein may compare a measured resistance of the resistive heater to a target resistance using a Wheatstone bridge and thereby adjust the power to increase/decrease the applied power based on this comparison.

In any of the variations described herein, adjusting the applied power to the resistive heater may comprise comparing the resistance (actual resistance) of the resistive heater to a target resistance using a voltage divider, Wheatstone bridge, amplified Wheatstone bridge, or RC charge time circuit.

As mentioned above, a target resistance of the resistive heater and therefore target temperature may be determined using a baseline resistance measurement taken from the resistive heater. The apparatus and/or method may approximate a baseline resistance for the resistive heater by waiting an appropriate length of time (e.g., 1 second, 10 seconds, 30 seconds, 1 minute, 1.5 minutes, 2 minutes, 3 minutes, 4 minutes, 5 minutes, 6 minutes, 7 minutes, 8 minutes, 9 minutes, 10 minutes, 11 minutes, 12 minutes, 15 minutes, 20 minutes, etc.) from the last application of energy to the resistive heater to measure a resistance (or series of resistance that may be averaged, etc.) representing the baseline resistance for the resistive heater. In some variations a plurality of measurements made when heating/applying power to the resistive heater is prevented may be analyzed by the apparatus to determine when the resistance values do not vary outside of a predetermined range (e.g., when the resistive heater has 'cooled' down, and therefore the resistance is no longer changing due to temperature decreasing/increasing), for example, when the rate of change of the resistance of the heating element over time is below some stability threshold.

For example, any of the methods and apparatuses described herein may measure the resistance of the resistive heater an ambient temperature by measuring the resistance of the resistive heater after a predetermined time since power was last applied to the resistive heater. As mentioned above, the predetermined time period may be seconds, minutes, etc.

In any of these variations the baseline resistance may be stored in a long-term memory (including volatile, non-volatile or semi-volatile memory). Storing a baseline resistance ("the resistance of the resistive heater an ambient temperature") may be done periodically (e.g., once per 2 minute, 5 minutes, 10 minutes, 1 hour, etc., or every time a particular event occurs, such as loading vaporizable material), or once for a single time.

Any of these methods may also include calculating an absolute target coil temperature from an actual device temperature. As mentioned, above, based on the material properties of the resistive heater (e.g., coil) the resistance and/or change in resistance over time may be used calculate an actual temperature, which may be presented to a user, e.g., on the face of the device, or communicated to an "app" or other output type.

In any of the methods and apparatuses described herein, the apparatus may detect the resistance of the resistive heater only when power is not being applied to the resistive heater while detecting the resistance; once the resistance detection is complete, power may again be applied (and this application may be modified by the control logic described herein). For example, in any of these devices and methods the resistance of the resistive heater may be measured only when suspending the application of power to the resistive heater.

For example, a method of controlling a vaporization device may include: placing a vaporizable material in thermal contact with a resistive heater; applying power to the resistive heater to heat the vaporizable material; suspending the application of power to the resistive heater while measuring the resistance of the resistive heater; and adjusting the applied power to the resistive heater based on the difference between the resistance of the heating element and a target resistance of the resistive heater, wherein measuring the resistance of the resistive heater comprises measuring the resistance using a voltage divider, Wheatstone bridge, amplified Wheatstone bridge, or RC charge time circuit.

For example, a vaporization device may include: a microcontroller; a reservoir configured to hold a vaporizable material; a resistive heater configured to thermally contact the vaporizable material from the reservoir; a resistance measurement circuit connected to the microcontroller configured to measure the resistance of the resistive heater; and a power source, wherein the microcontroller applies power from the power source to heat the resistive heater and adjusts the applied power based on the difference between the resistance of the resistive heater and a target resistance of the resistive heater.

A vaporization device may include: a microcontroller; a reservoir configured to hold a vaporizable material; a resistive heater configured to thermally contact the vaporizable material from the reservoir; a resistance measurement circuit connected to the microcontroller configured to measure the resistance of the resistive heater; a power source; and a sensor having an output connected to the microcontroller, wherein the microcontroller is configured to determine when the resistive heater applies power from the power source to heat the resistive heater; a target resistance circuit configured to determine a target resistance, the target resistance circuit comprising one of: a voltage divider, a Wheatstone bridge, an amplified Wheatstone bridge, or an RC charge time circuit, wherein the microcontroller applies power from the power source to heat the resistive heater and adjusts the applied power based on the difference between the resistance of the resistive heater and the target resistance of the resistive heater.

In any of the methods and apparatuses (e.g., devices and systems) described herein, the apparatus may be configured to be triggered by a user drawing on or otherwise indicating that they would like to begin vaporization of the vaporizing material. This user-initiated start may be detected by a sensor, such as a pressure sensor ("puff sensor") configured to detect draw. The sensor may generally have an output that is connected to the controller (e.g., microcontroller), and the microcontroller may be configured to determine when the resistive heater applies power from the power source to heat the resistive heater.

For example, a vaporizing device as described herein may include a pressure sensor having an output connected to the microcontroller, wherein the microcontroller is configured to determine when the resistive heater applies power from the power source to heat the resistive heater.

In general, any of the apparatuses described herein may be adapted to perform any of the methods described herein, including determining if an instantaneous (ongoing) resistance measurement of the resistive heater is above/below and/or within a tolerable range of a target resistance. Any of these apparatuses may also determine the target resistance. As mentioned, this may be determined empirically and set to a resistance value, and/or it may be calculated. For example, any of these apparatuses (e.g., devices) may include a target resistance circuit configured to determine the target resistance, the target resistance circuit comprising one of: a voltage divider, a Wheatstone bridge, an amplified Wheatstone bridge, or an RC charge time circuit. Alternatively or additionally, a voltage divider, a Wheatstone bridge, an amplified Wheatstone bridge, or an RC charge time circuit may be included as part of the microcontroller or other circuitry that compares the measured resistance of the resistive heater to a target resistance.

For example, a target resistance circuit may be configured to determine the target resistance and/or compare the measured resistance of the resistive heater to the target resistance. The target resistance circuit comprising a voltage divider having a reference resistance equivalent to the target resistance. A target resistance circuit may be configured to determine the target resistance, the target resistance circuit comprising a Wheatstone bridge, wherein the target resistance is calculated by adding a resistance of the resistive heater at an ambient temperature and a target change in temperature of the resistive heater.

As mentioned, any of these apparatuses may include a memory configured to store a resistance of the resistive heater at an ambient temperature. Further, any of these apparatuses may include a temperature input coupled to the microcontroller and configured to provide an actual device temperature. The device temperature may be sensed and/or provided by any appropriate sensor, including thermistor, thermocouple, resistive temperature sensor, silicone band-gap temperature sensor, etc. The measured device temperature may be used to calculate a target resistance that corresponds to a certain resistive heater (e.g., coil) temperature.

In some variations the apparatus may display and/or output an an estimate of the temperature of the resistive heater. The apparatus may include a display or may communicate (e.g., wirelessly) with another apparatus that receives the temperature or resistance values.

The devices described herein may include an inhalable aerosol comprising: an oven comprising an oven chamber and a heater for heating a vapor forming medium in the oven chamber to generate a vapor; a condenser comprising a condensation chamber in which at least a fraction of the vapor condenses to form the inhalable aerosol; an air inlet that originates a first airflow path that includes the oven chamber; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber to a user.

In any of these variations the oven is within a body of the device. The device may further comprise a mouthpiece, wherein the mouthpiece comprises at least one of the air inlet, the aeration vent, and the condenser. The mouthpiece may be separable from the oven. The mouthpiece may be integral to a body of the device, wherein the body comprises the oven. The device may further comprise a body that comprises the oven, the condenser, the air inlet, and the aeration vent. The mouthpiece may be separable from the body.

In some variations, the oven chamber may comprise an oven chamber inlet and an oven chamber outlet, and the oven further comprises a first valve at the oven chamber inlet, and a second valve at the oven chamber outlet. The aeration vent may comprise a third valve. The first valve, or said second valve may be chosen from the group of a check valve, a clack valve, a non-return valve, and a one-way valve. The third valve may be chosen from the group of a check valve, a clack valve, a non-return valve, and a one-way valve. The first or second valve may be mechanically actuated. The first or second valve may be electronically actuated. The first valve or second valve may be manually actuated. The third valve may be mechanically actuated. The third valve may be mechanically actuated. The third valve may be electronically actuated. The third valve may be manually actuated.

In any of these variations, the device may further comprise a body that comprises at least one of: a power source, a printed circuit board, a switch, and a temperature regulator. The device may further comprise a temperature regulator in communication with a temperature sensor. The temperature sensor may be the heater. The power source may be rechargeable. The power source may be removable. The oven may further comprise an access lid. The vapor forming medium may comprise tobacco. The vapor forming medium may comprise a botanical. The vapor forming medium may be heated in the oven chamber wherein the vapor forming medium may comprise a humectant to produce the vapor, wherein the vapor comprises a gas phase humectant. The vapor may be mixed in the condensation chamber with air from the aeration vent to produce the inhalable aerosol comprising particle diameters of average size of about 1 micron. The vapor forming medium may be heated in the oven chamber, wherein the vapor is mixed in the condensation chamber with air from the aeration vent to produce the inhalable aerosol comprising particle diameters of average size of less than or equal to 0.9 micron. The vapor forming medium may be heated in the oven chamber, wherein the vapor is mixed in the condensation chamber with air from the aeration vent to produce the inhalable aerosol comprising particle diameters of average size of less than or equal to 0.8 micron. The vapor forming medium may be heated in the oven chamber, wherein the vapor is mixed in the condensation chamber with air from the aeration vent to produce the inhalable aerosol comprising particle diameters of average size of less than or equal to 0.7 micron. The vapor forming medium may be heated in the oven chamber, wherein the vapor is mixed in the condensation chamber with air from the aeration vent to produce the inhalable aerosol comprising particle diameters of average size of less than or equal to 0.6 micron. The vapor forming medium may be heated in the oven chamber, wherein the vapor is mixed in the condensation chamber with air from the aeration vent to produce the inhalable aerosol comprising particle diameters of average size of less than or equal to 0.5 micron.

In any of these variations, the humectant may comprise glycerol as a vapor-forming medium. The humectant may comprise vegetable glycerol. The humectant may comprise propylene glycol. The humectant may comprise a ratio of vegetable glycerol to propylene glycol. The ratio may be about 100:0 vegetable glycerol to propylene glycol. The ratio may be about 90:10 vegetable glycerol to propylene glycol. The ratio may be about 80:20 vegetable glycerol to propylene glycol. The ratio may be about 70:30 vegetable glycerol to propylene glycol. The ratio may be about 60:40 vegetable glycerol to propylene glycol. The ratio may be about 50:50 vegetable glycerol to propylene glycol. The humectant may comprise a flavorant. The vapor forming medium may be heated to its pyrolytic temperature. The vapor forming medium may heated to 200° C. at most. The vapor forming medium may be heated to 160° C. at most. The inhalable aerosol may be cooled to a temperature of about 50°-70° C. at most, before exiting the aerosol outlet of the mouthpiece.

In any of these variations, the method comprises A method for generating an inhalable aerosol, the method comprising: providing an inhalable aerosol generating device wherein the device comprises: an oven comprising an oven chamber and a heater for heating a vapor forming medium in the oven chamber and for forming a vapor therein; a condenser comprising a condensation chamber in which the vapor forms the inhalable aerosol; an air inlet that originates a first airflow path that includes the oven chamber; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber to a user.

In any of these variations the oven is within a body of the device. The device may further comprise a mouthpiece, wherein the mouthpiece comprises at least one of the air inlet, the aeration vent, and the condenser. The mouthpiece may be separable from the oven. The mouthpiece may be integral to a body of the device, wherein the body comprises the oven. The method may further comprise a body that comprises the oven, the condenser, the air inlet, and the aeration vent. The mouthpiece may be separable from the body.

In any of these variations, the oven chamber may comprise an oven chamber inlet and an oven chamber outlet, and the oven further comprises a first valve at the oven chamber inlet, and a second valve at the oven chamber outlet.

The vapor forming medium may comprise tobacco. The vapor forming medium may comprise a botanical. The vapor forming medium may be heated in the oven chamber wherein the vapor forming medium may comprise a humectant to produce the vapor, wherein the vapor comprises a gas phase humectant. The vapor may comprise particle diameters of average mass of about 1 micron. The vapor may comprise particle diameters of average mass of about 0.9 micron. The vapor may comprise particle diameters of average mass of about 0.8 micron. The vapor may comprise particle diameters of average mass of about 0.7 micron. The vapor may comprise particle diameters of average mass of about 0.6 micron. The vapor may comprise particle diameters of average mass of about 0.5 micron.

In any of these variations, the humectant may comprise glycerol as a vapor-forming medium. The humectant may comprise vegetable glycerol. The humectant may comprise propylene glycol. The humectant may comprise a ratio of vegetable glycerol to propylene glycol. The ratio may be about 100:0 vegetable glycerol to propylene glycol. The ratio may be about 90:10 vegetable glycerol to propylene glycol. The ratio may be about 80:20 vegetable glycerol to propylene glycol. The ratio may be about 70:30 vegetable glycerol to propylene glycol. The ratio may be about 60:40 vegetable glycerol to propylene glycol. The ratio may be about 50:50 vegetable glycerol to propylene glycol. The humectant may comprise a flavorant. The vapor forming medium may be heated to its pyrolytic temperature. The vapor forming medium may heated to 200° C. at most. The vapor forming medium may be heated to 160° C. at most. The inhalable aerosol may be cooled to a temperature of about 50°-70° C. at most, before exiting the aerosol outlet of the mouthpiece.

In any of these variations, the device may be user serviceable. The device may not be user serviceable.

In any of these variations, a method for generating an inhalable aerosol, the method comprising: providing a vaporization device, wherein said device produces a vapor comprising particle diameters of average mass of about 1 micron or less, wherein said vapor is formed by heating a vapor forming medium in an oven chamber to a first temperature below the pyrolytic temperature of said vapor forming medium, and cooling said vapor in a condensation chamber to a second temperature below the first temperature, before exiting an aerosol outlet of said device.

In any of these variations, a method of manufacturing a device for generating an inhalable aerosol comprising: providing said device comprising a mouthpiece comprising an aerosol outlet at a first end of the device; an oven comprising an oven chamber and a heater for heating a vapor forming medium in the oven chamber and for forming a vapor therein, a condenser comprising a condensation chamber in which the vapor forms the inhalable aerosol, an air inlet that originates a first airflow path that includes the oven chamber and then the condensation chamber, an aeration vent that originates a second airflow path that joins the first airflow path prior to or within the condensation chamber after the vapor is formed in the oven chamber, wherein the joined first airflow path and second airflow path are configured to deliver the inhalable aerosol formed in the condensation chamber through the aerosol outlet of the mouthpiece to a user.

The method may further comprise providing the device comprising a power source or battery, a printed circuit board, a temperature regulator or operational switches.

In any of these variations a device for generating an inhalable aerosol may comprise a mouthpiece comprising an aerosol outlet at a first end of the device and an air inlet that originates a first airflow path; an oven comprising an oven chamber that is in the first airflow path and includes the oven chamber and a heater for heating a vapor forming medium in the oven chamber and for forming a vapor therein; a condenser comprising a condensation chamber in which the vapor forms the inhalable aerosol; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber through the aerosol outlet of the mouthpiece to a user.

In any of these variations a device for generating an inhalable aerosol may comprise: a mouthpiece comprising an aerosol outlet at a first end of the device, an air inlet that originates a first airflow path, and an aeration vent that originates a second airflow path that allows air from the aeration vent to join the first airflow path; an oven comprising an oven chamber that is in the first airflow path and includes the oven chamber and a heater for heating a vapor forming medium in the oven chamber and for forming a vapor therein; and a condenser comprising a condensation chamber in which the vapor forms the inhalable aerosol and wherein air from the aeration vent joins the first airflow path prior to or within the condensation chamber and downstream from the oven chamber thereby forming a joined path, wherein the joined path is configured to deliver the inhalable aerosol through the aerosol outlet of the mouthpiece to a user.

In any of these variations, a device for generating an inhalable aerosol may comprise: a device body comprising a cartridge receptacle; a cartridge comprising: a fluid storage compartment, and a channel integral to an exterior surface of the cartridge, and an air inlet passage formed by the channel and an internal surface of the cartridge receptacle when the cartridge is inserted into the cartridge receptacle; wherein the channel forms a first side of the air inlet passage, and an internal surface of the cartridge receptacle forms a second side of the air inlet passage.

In any of these variations, a device for generating an inhalable aerosol may comprise: a device body comprising a cartridge receptacle; a cartridge comprising: a fluid storage compartment, and a channel integral to an exterior surface of the cartridge, and an air inlet passage formed by the channel and an internal surface of the cartridge receptacle when the cartridge is inserted into the cartridge receptacle; wherein the channel forms a first side of the air inlet passage, and an internal surface of the cartridge receptacle forms a second side of the air inlet passage.

In any of these variations the channel may comprise at least one of a groove, a trough, a depression, a dent, a furrow, a trench, a crease, and a gutter. The integral channel may comprise walls that are either recessed into the surface or protrude from the surface where it is formed. The internal side walls of the channel may form additional sides of the air inlet passage. The cartridge may further comprise a second air passage in fluid communication with the air inlet passage to the fluid storage compartment, wherein the second air passage is formed through the material of the cartridge. The cartridge may further comprise a heater. The heater may be attached to a first end of the cartridge.

In any of these variations the heater may comprise a heater chamber, a first pair of heater contacts, a fluid wick, and a resistive heating element in contact with the wick, wherein the first pair of heater contacts comprise thin plates affixed about the sides of the heater chamber, and wherein the fluid wick and resistive heating element are suspended therebetween. The first pair of heater contacts may further comprise a formed shape that comprises a tab having a flexible spring value that extends out of the heater to couple to complete a circuit with the device body. The first pair of heater contacts may be a heat sink that absorbs and dissipates excessive heat produced by the resistive heating element. The first pair of heater contacts may contact a heat shield that protects the heater chamber from excessive heat produced by the resistive heating element. The first pair of heater contacts may be press-fit to an attachment feature on the exterior wall of the first end of the cartridge. The heater may enclose a first end of the cartridge and a first end of the fluid storage compartment. The heater may comprise a first condensation chamber. The heater may comprise more than one first condensation chamber. The first condensation chamber may be formed along an exterior wall of the cartridge. The cartridge may further comprise a mouthpiece. The mouthpiece may be attached to a second end of the cartridge. The mouthpiece may comprise a second condensation chamber. The mouthpiece may comprise more than one second condensation chamber. The second condensation chamber may be formed along an exterior wall of the cartridge.

In any of these variations the cartridge may comprise a first condensation chamber and a second condensation chamber. The first condensation chamber and the second condensation chamber may be in fluid communication. The mouthpiece may comprise an aerosol outlet in fluid communication with the second condensation chamber. The mouthpiece may comprise more than one aerosol outlet in fluid communication with more than one the second condensation chamber. The mouthpiece may enclose a second end of the cartridge and a second end of the fluid storage compartment.

In any of these variations, the device may comprise an airflow path comprising an air inlet passage, a second air passage, a heater chamber, a first condensation chamber, a second condensation chamber, and an aerosol outlet. The airflow path may comprise more than one air inlet passage, a heater chamber, more than one first condensation chamber, more than one second condensation chamber, more than one second condensation chamber, and more than one aerosol outlet. The heater may be in fluid communication with the fluid storage compartment. The fluid storage compartment may be capable of retaining condensed aerosol fluid. The condensed aerosol fluid may comprise a nicotine formulation. The condensed aerosol fluid may comprise a humectant. The humectant may comprise propylene glycol. The humectant may comprise vegetable glycerin.

In any of these variations the cartridge may be detachable. In any of these variations the cartridge may be receptacle and the detachable cartridge form a separable coupling. The separable coupling may comprise a friction assembly, a snap-fit assembly or a magnetic assembly. The cartridge may comprise a fluid storage compartment, a heater affixed to a first end with a snap-fit coupling, and a mouthpiece affixed to a second end with a snap-fit coupling.

In any of these variations, a device for generating an inhalable aerosol may comprise: a device body comprising a cartridge receptacle for receiving a cartridge; wherein an interior surface of the cartridge receptacle forms a first side of an air inlet passage when a cartridge comprising a channel integral to an exterior surface is inserted into the cartridge receptacle, and wherein the channel forms a second side of the air inlet passage.

In any of these variations, a device for generating an inhalable aerosol may comprise: a device body comprising a cartridge receptacle for receiving a cartridge; wherein the cartridge receptacle comprises a channel integral to an interior surface and forms a first side of an air inlet passage when a cartridge is inserted into the cartridge receptacle, and wherein an exterior surface of the cartridge forms a second side of the air inlet passage.

In any of these variations, A cartridge for a device for generating an inhalable aerosol comprising: a fluid storage compartment; a channel integral to an exterior surface, wherein the channel forms a first side of an air inlet passage; and wherein an internal surface of a cartridge receptacle in the device forms a second side of the air inlet passage when the cartridge is inserted into the cartridge receptacle.

In any of these variations, a cartridge for a device for generating an inhalable aerosol may comprise: a fluid storage compartment, wherein an exterior surface of the cartridge forms a first side of an air inlet channel when inserted into a device body comprising a cartridge receptacle, and wherein the cartridge receptacle further comprises a channel integral to an interior surface, and wherein the channel forms a second side of the air inlet passage.

The cartridge may further comprise a second air passage in fluid communication with the channel, wherein the second air passage is formed through the material of the cartridge from an exterior surface of the cartridge to the fluid storage compartment.

The cartridge may comprise at least one of: a groove, a trough, a depression, a dent, a furrow, a trench, a crease, and a gutter. The integral channel may comprise walls that are either recessed into the surface or protrude from the surface where it is formed. The internal side walls of the channel may form additional sides of the air inlet passage.

In any of these variations, a device for generating an inhalable aerosol may comprise: a cartridge comprising; a fluid storage compartment; a heater affixed to a first end comprising; a first heater contact, a resistive heating element affixed to the first heater contact; a device body comprising; a cartridge receptacle for receiving the cartridge; a second heater contact adapted to receive the first heater contact and to complete a circuit; a power source connected to the second heater contact; a printed circuit board (PCB) connected to the power source and the second heater contact; wherein the PCB is configured to detect the absence of fluid based on the measured resistance of the resistive heating element, and turn off the device.

The printed circuit board (PCB) may comprise a microcontroller; switches; circuitry comprising a reference resister; and an algorithm comprising logic for control parameters; wherein the microcontroller cycles the switches at fixed intervals to measure the resistance of the resistive heating element relative to the reference resistor, and applies the algorithm control parameters to control the temperature of the resistive heating element.

The micro-controller may instruct the device to turn itself off when the resistance exceeds the control parameter threshold indicating that the resistive heating element is dry.

In any of these variations, a cartridge for a device for generating an inhalable aerosol may comprise: a fluid storage compartment; a heater affixed to a first end comprising: a heater chamber, a first pair of heater contacts, a fluid wick, and a resistive heating element in contact with the wick; wherein the first pair of heater contacts comprise thin plates affixed about the sides of the heater chamber, and wherein the fluid wick and resistive heating element are suspended therebetween.

The first pair of heater contacts may further comprise: a formed shape that comprises a tab having a flexible spring value that extends out of the heater to complete a circuit with the device body. The heater contacts may be configured to mate with a second pair of heater contacts in a cartridge receptacle of the device body to complete a circuit. The first pair of heater contacts may also be a heat sink that absorbs and dissipates excessive heat produced by the resistive heating element. The first pair of heater contacts may be a heat shield that protects the heater chamber from excessive heat produced by the resistive heating element.

In any of these variations, a cartridge for a device for generating an inhalable aerosol may comprise: a heater comprising; a heater chamber, a pair of thin plate heater contacts therein, a fluid wick positioned between the heater contacts, and a resistive heating element in contact with the wick; wherein the heater contacts each comprise a fixation site wherein the resistive heating element is tensioned therebetween.

In any of these variations, a cartridge for a device for generating an inhalable aerosol may comprise a heater, wherein the heater is attached to a first end of the cartridge.

The heater may enclose a first end of the cartridge and a first end of the fluid storage compartment. The heater may comprise more than one first condensation chamber. The heater may comprise a first condensation chamber. The condensation chamber may be formed along an exterior wall of the cartridge.

In any of these variations, a cartridge for a device for generating an inhalable aerosol may comprise a fluid storage compartment; and a mouthpiece, wherein the mouthpiece is attached to a second end of the cartridge.

The mouthpiece may enclose a second end of the cartridge and a second end of the fluid storage compartment. The mouthpiece may comprise a second condensation chamber. The mouthpiece may comprise more than one second condensation chamber. The second condensation chamber may be formed along an exterior wall of the cartridge.

In any of these variations, a cartridge for a device for generating an inhalable aerosol may comprise: a fluid storage compartment; a heater affixed to a first end; and a mouthpiece affixed to a second end; wherein the heater comprises a first condensation chamber and the mouthpiece comprises a second condensation chamber.

The heater may comprise more than one first condensation chamber and the mouthpiece comprises more than one second condensation chamber. The first condensation chamber and the second condensation chamber may be in fluid communication. The mouthpiece may comprise an aerosol outlet in fluid communication with the second condensation chamber. The mouthpiece may comprise two to more aerosol outlets. The cartridge may meet ISO recycling standards. The cartridge may meet ISO recycling standards for plastic waste.

In any of these variations, a device for generating an inhalable aerosol may comprise: a device body comprising a cartridge receptacle; and a detachable cartridge; wherein the cartridge receptacle and the detachable cartridge form a separable coupling, wherein the separable coupling comprises a friction assembly, a snap-fit assembly or a magnetic assembly.

In any of these variations, a method of fabricating a device for generating an inhalable aerosol may comprise: providing a device body comprising a cartridge receptacle; and providing a detachable cartridge; wherein the cartridge receptacle and the detachable cartridge form a separable coupling comprising a friction assembly, a snap-fit assembly or a magnetic assembly.

In any of these variations, a method of fabricating a cartridge for a device for generating an inhalable aerosol may comprise: providing a fluid storage compartment; affixing a heater to a first end with a snap-fit coupling; and affixing a mouthpiece to a second end with a snap-fit coupling.

In any of these variations A cartridge for a device for generating an inhalable aerosol with an airflow path comprising: a channel comprising a portion of an air inlet passage; a second air passage in fluid communication with the channel; a heater chamber in fluid communication with the second air passage; a first condensation chamber in fluid communication with the heater chamber; a second condensation chamber in fluid communication with the first condensation chamber; and an aerosol outlet in fluid communication with second condensation chamber.

In any of these variations, a cartridge for a device for generating an inhalable aerosol may comprise: a fluid storage compartment; a heater affixed to a first end; and a mouthpiece affixed to a second end; wherein said mouthpiece comprises two or more aerosol outlets.

In any of these variations, a system for providing power to an electronic device for generating an inhalable vapor, the system may comprise; a rechargeable power storage device housed within the electronic device for generating an inhalable vapor; two or more pins that are accessible from an exterior surface of the electronic device for generating an inhalable vapor, wherein the charging pins are in electrical communication with the rechargeable power storage device; a charging cradle comprising two or more charging contacts configured to provided power to the rechargeable storage device, wherein the device charging pins are reversible such that the device is charged in the charging cradle for charging with a first charging pin on the device in contact a first charging contact on the charging cradle and a second charging pin on the device in contact with second charging contact on the charging cradle and with the first charging pin on the device in contact with second charging contact on the charging cradle and the second charging pin on the device in contact with the first charging contact on the charging cradle.

The charging pins may be visible on an exterior housing of the device. The user may permanently disable the device by opening the housing. The user may permanently destroy the device by opening the housing.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIG. 5 is an illustrative isometric view of an assembled inhalable aerosol device.

FIGS. 6A-6D are illustrative arrangements and section views of the device body and sub-components.

FIGS. 16A-16C are representative illustrations of a charging device for the aerosol device and the application of the charger with the device.

FIGS. 17A and 17B are representative illustrations of a proportional-integral-derivative controller (PID) block diagram and circuit diagram representing the essential components in a device to control coil temperature.

FIGS. 25A and 25B show front a side views, respectively, of the cartridge of FIGS. 24A and 24B.

FIG. 26A shows a section through a cartridge device holding a vaporizable material for securely coupling with an electronic inhalable aerosol device and indicates exemplary dimensions (in mm).

FIG. 26B shows a side view of the cartridge of FIG. 26A, indicating where the sectional view of FIG. 26A was taken.

FIG. 27A is a side view and FIG. 27B shows a sectional view with exemplary dimensions of the rectangular opening for holding and making electrical contact with a cartridge.

FIG. 28D is an enlarged view of the region showing the electrical and mechanical connection between the cartridge and the vaporizer indicted by the circular region D.

FIGS. 29A-29D illustrate side profiles of alternative variations of cartridges as described herein.

DETAILED DESCRIPTION

Figure 1:
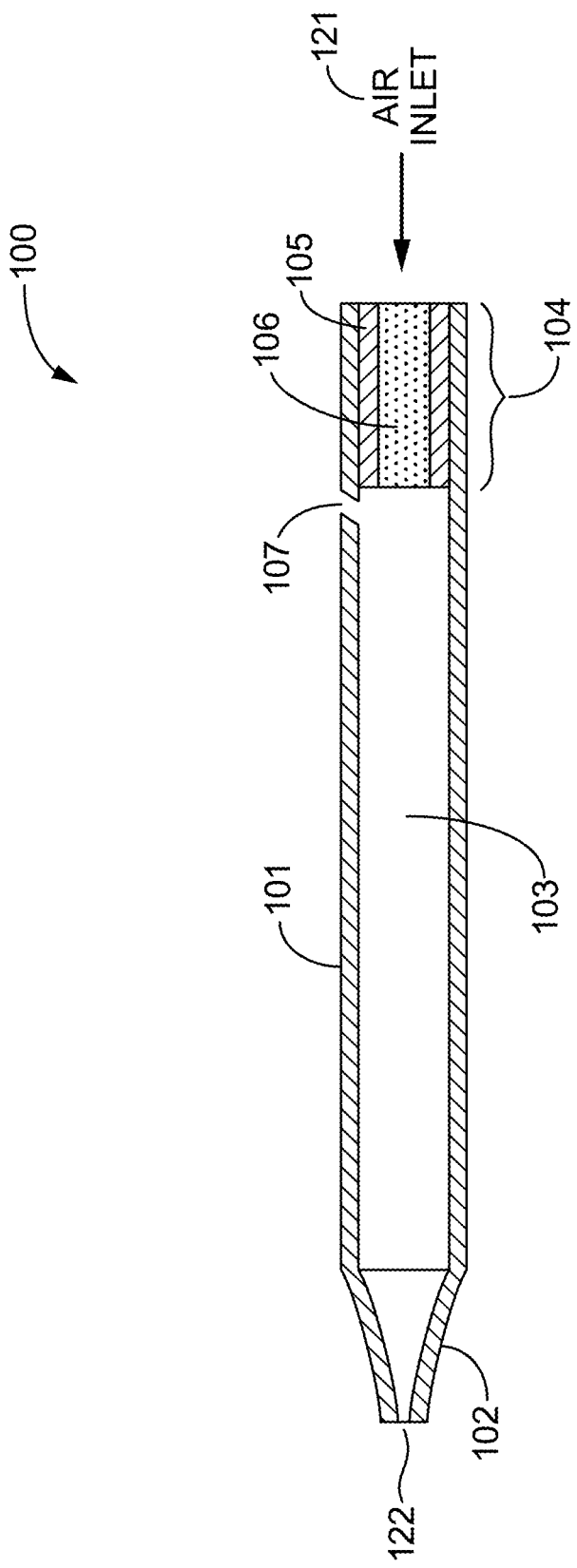
FIG. 1 is an illustrative cross-sectional view of an exemplary vaporization device.

Provided herein are systems and methods for generating a vapor from a material. The vapor may be delivered for inhalation by a user. The material may be a solid, liquid, powder, solution, paste, gel, or any a material with any other physical consistency. The vapor may be delivered to the user for inhalation by a vaporization device. The vaporization device may be a handheld vaporization device. The vaporization device may be held in one hand by the user.

The vaporization device may comprise a cartridge having one or more heating elements the heating element may be a resistive heating element. The heating element may heat the material such that the temperature of the material increases. Vapor may be generated as a result of heating the material. Energy may be required to operate the heating element, the energy may be derived from a battery in electrical communication with the heating element. Alternatively a chemical reaction (e.g., combustion or other exothermic reaction) may provide energy to the heating element.

One or more aspects of the vaporization device may be designed and/or controlled in order to deliver a vapor with one or more specified properties to the user. For example, aspects of the vaporization device that may be designed and/or controlled to deliver the vapor with specified properties may comprise the heating temperature, heating mechanism, device air inlets, internal volume of the device, and/or composition of the material.

In some cases, a vaporization device may have an "atomizer" or "cartomizer" configured to heat an aerosol forming solution (e.g., vaporizable material). The aerosol forming solution may comprise glycerin and/or propylene glycol. The vaporizable material may be heated to a sufficient temperature such that it may vaporize.

An atomizer may be a device or system configured to generate an aerosol. The atomizer may comprise a small heating element configured to heat and/or vaporize at least a portion of the vaporizable material and a wicking material that may draw a liquid vaporizable material in to the atomizer. The wicking material may comprise silica fibers, cotton, ceramic, hemp, stainless steel mesh, and/or rope cables. The wicking material may be configured to draw the liquid vaporizable material in to the atomizer without a pump or other mechanical moving part. A resistance wire may be wrapped around the wicking material and then connected to a positive and negative pole of a current source (e.g., energy source). The resistance wire may be a coil. When the resistance wire is activated the resistance wire (or coil) may have a temperature increase as a result of the current flowing through the resistive wire to generate heat. The heat may be transferred to at least a portion of the vaporizable material through conductive, convective, and/or radiative heat transfer such that at least a portion of the vaporizable material vaporizes.

Alternatively or in addition to the atomizer, the vaporization device may comprise a "cartomizer" to generate an aerosol from the vaporizable material for inhalation by the user. The cartomizer may comprise a cartridge and an atomizer. The cartomizer may comprise a heating element surrounded by a liquid-soaked poly-foam that acts as holder for the vaporizable material (e.g., the liquid). The cartomizer may be reusable, rebuildable, refillable, and/or disposable. The cartomizer may be used with a tank for extra storage of a vaporizable material.

Air may be drawn into the vaporization device to carry the vaporized aerosol away from the heating element, where it then cools and condenses to form liquid particles suspended in air, which may then be drawn out of the mouthpiece by the user.

The vaporization of at least a portion of the vaporizable material may occur at lower temperatures in the vaporization device compared to temperatures required to generate an inhalable vapor in a cigarette. A cigarette may be a device in which a smokable material is burned to generate an inhalable vapor. The lower temperature of the vaporization device may result in less decomposition and/or reaction of the vaporized material, and therefore produce an aerosol with many fewer chemical components compared to a cigarette. In some cases, the vaporization device may generate an aerosol with fewer chemical components that may be harmful to human health compared to a cigarette. Additionally, the vaporization device aerosol particles may undergo nearly complete evaporation in the heating process, the nearly complete evaporation may yield an average particle size (e.g., diameter) value that may be smaller than the average particle size in tobacco or botanical based effluent.

A vaporization device may be a device configured to extract for inhalation one or more active ingredients of plant material, tobacco, and/or a botanical, or other herbs or blends. A vaporization device may be used with pure chemicals and/or humectants that may or may not be mixed with plant material. Vaporization may be alternative to burning (smoking) that may avoid the inhalation of many irritating and/or toxic carcinogenic by-products which may result from the pyrolytic process of burning tobacco or botanical products above 300° C. The vaporization device may operate at a temperature at or below 300° C.

A vaporizer (e.g., vaporization device) may not have an atomizer or cartomizer. Instead the device may comprise an oven. The oven may be at least partially closed. The oven may have a closable opening. The oven may be wrapped with a heating element, alternatively the heating element may be in thermal communication with the oven through another mechanism. A vaporizable material may be placed directly in the oven or in a cartridge fitted in the oven. The heating element in thermal communication with the oven may heat a vaporizable material mass in order to create a gas phase vapor. The heating element may heat the vaporizable material through conductive, convective, and/or radiative heat transfer. The vapor may be released to a vaporization chamber where the gas phase vapor may condense, forming an aerosol cloud having typical liquid vapor particles with particles having a diameter of average mass of approximately 1 micron or greater. In some cases the diameter of average mass may be approximately 0.1-1 micron.

A used herein, the term "vapor" may generally refer to a substance in the gas phase at a temperature lower than its critical point. The vapor may be condensed to a liquid or to a solid by increasing its pressure without reducing the temperature.

As used herein, the term "aerosol" may generally refer to a colloid of fine solid particles or liquid droplets in air or another gas. Examples of aerosols may include clouds, haze, and smoke, including the smoke from tobacco or botanical products. The liquid or solid particles in an aerosol may have varying diameters of average mass that may range from monodisperse aerosols, producible in the laboratory, and containing particles of uniform size; to polydisperse colloidal systems, exhibiting a range of particle sizes. As the sizes of these particles become larger, they have a greater settling speed which causes them to settle out of the aerosol faster, making the appearance of the aerosol less dense and to shorten the time in which the aerosol will linger in air. Interestingly, an aerosol with smaller particles will appear thicker or denser because it has more particles. Particle number has a much bigger impact on light scattering than particle size (at least for the considered ranges of particle size), thus allowing for a vapor cloud with many more smaller particles to appear denser than a cloud having fewer, but larger particle sizes.

As used herein the term "humectant" may generally refer to as a substance that is used to keep things moist. A humectant may attract and retain moisture in the air by absorption, allowing the water to be used by other substances. Humectants are also commonly used in many tobaccos or botanicals and electronic vaporization products to keep products moist and as vapor-forming medium. Examples include propylene glycol, sugar polyols such as glycerol, glycerin, and honey.

Rapid Aeration

In some cases, the vaporization device may be configured to deliver an aerosol with a high particle density. The particle density of the aerosol may refer to the number of the aerosol droplets relative to the volume of air (or other dry gas) between the aerosol droplets. A dense aerosol may easily be visible to a user. In some cases the user may inhale the aerosol and at least a fraction of the aerosol particles may impinge on the lungs and/or mouth of the user. The user may exhale residual aerosol after inhaling the aerosol. When the aerosol is dense the residual aerosol may have sufficient particle density such that the exhaled aerosol is visible to the user. In some cases, a user may prefer the visual effect and/or mouth feel of a dense aerosol.

A vaporization device may comprise a vaporizable material. The vaporizable material may be contained in a cartridge or the vaporizable material may be loosely placed in one or more cavities the vaporization device. A heating element may be provided in the device to elevate the temperature of the vaporizable material such that at least a portion of the vaporizable material forms a vapor. The heating element may heat the vaporizable material by convective heat transfer, conductive heat transfer, and/or radiative heat transfer. The heating element may heat the cartridge and/or the cavity in which the vaporizable material is stored.

Vapor formed upon heating the vaporizable material may be delivered to the user. The vapor may be transported through the device from a first position in the device to a second position in the device. In some cases, the first position may be a location where at least a portion of the vapor was generated, for example, the cartridge or cavity or an area adjacent to the cartridge or cavity. The second position may be a mouthpiece. The user may suck on the mouthpiece to inhale the vapor.

At least a fraction of the vapor may condense after the vapor is generated and before the vapor is inhaled by the user. The vapor may condense in a condensation chamber. The condensation chamber may be a portion of the device that the vapor passes through before delivery to the user. In some cases, the device may include at least one aeration vent, placed in the condensation chamber of the vaporization device. The aeration vent may be configured to introduce ambient air (or other gas) into the vaporization chamber. The air introduced into the vaporization chamber may have a temperature lower than the temperature of a gas and/or gas/vapor mixture in the condensation chamber. Introduction of the relatively lower temperature gas into the vaporization chamber may provide rapid cooling of the heated gas vapor mixture that was generated by heating the vaporizable material. Rapid cooling of the gas vapor mixture may generate a dense aerosol comprising a high concentration of liquid droplets having a smaller diameter and/or smaller average mass compared to an aerosol that is not rapidly cooled prior to inhalation by the user.

An aerosol with a high concentration of liquid droplets having a smaller diameter and/or smaller average mass compared to an aerosol that is not rapidly cooled prior to inhalation by the user may be formed in a two-step process. The first step may occur in the oven chamber where the vaporizable material (e.g., tobacco and/or botanical and humectant blend) may be heated to an elevated temperature. At the elevated temperature, evaporation may happen faster than at room temperature and the oven chamber may fill with the vapor phase of the humectants. The humectant may continue to evaporate until the partial pressure of the humectant is equal to the saturation pressure. At this point, the gas is said to have a saturation ratio of 1 ($S=P_{partial}/P_{sat}$).

In the second step, the gas (e.g., vapor and air) may exit the oven and enter a condenser or condensation chamber and begin to cool. As the gas phase vapor cools, the saturation pressure may decrease. As the saturation pressure decreases, the saturation ratio may increase and the vapor may begin to condense, forming droplets. In some devices, with the absence of added cooling aeration, the cooling may be relatively slower such that high saturation pressures may not be reached, and the droplets that form in the devices without added cooling aeration may be relatively larger and fewer in numbers. When cooler air is introduced, a temperature gradient may be formed between the cooler air and the relatively warmer gas in the device. Mixing between the cooler air and the relatively warmer gas in a confined space inside of the vaporization device may lead to rapid cooling. The rapid cooling may generate high saturation ratios, small particles, and high concentrations of smaller particles, forming a thicker, denser vapor cloud compared to particles generated in a device without the aeration vents.

For the purpose of this disclosure, when referring to ratios of humectants such as vegetable glycerol or propylene glycol, "about" means a variation of 5%, 10%, 20% or 25% depending on the embodiment.

For the purpose of this disclosure, when referring to a diameter of average mass in particle sizes, "about" means a variation of 5%, 10%, 20% or 25% depending on the embodiment.

A vaporization device configured to rapidly cool a vapor may comprise: a mouthpiece comprising an aerosol outlet at a first end of the device; an oven comprising an oven chamber and a heater for heating a vapor forming medium in the oven chamber and for forming a vapor therein; a condenser comprising a condensation chamber in which the vapor forms the inhalable aerosol; an air inlet that originates a first airflow path that includes the oven chamber and then the condensation chamber, an aeration vent that originates a second airflow path that joins the first airflow path prior to or within the condensation chamber after the vapor is formed in the oven chamber, wherein the joined first airflow path and second airflow path are configured to deliver the inhalable aerosol formed in the condensation chamber through the aerosol outlet of the mouthpiece to a user.

In some embodiments, the oven is within a body of the device. The oven chamber may comprise an oven chamber inlet and an oven chamber outlet. The oven may further comprise a first valve at the oven chamber inlet, and a second valve at the oven chamber outlet.

The oven may be contained within a device housing. In some cases the body of the device may comprise the aeration vent and/or the condenser. The body of the device may comprise one or more air inlets. The body of the device may comprise a housing that holds and/or at least partially contains one or more elements of the device.

The mouthpiece may be connected to the body. The mouthpiece may be connected to the oven. The mouthpiece may be connected to a housing that at least partially encloses the oven. In some cases, the mouthpiece may be separable from the oven, the body, and/or the housing that at least partially encloses the oven. The mouthpiece may comprise at least one of the air inlet, the aeration vent, and the condenser. The mouthpiece may be integral to the body of the device. The body of the device may comprise the oven.

In some cases, the one or more aeration vents may comprise a valve. The valve may regulate a flow rate of air entering the device through the aeration vent. The valve may be controlled through a mechanical and/or electrical control system.

A vaporization device configured to rapidly cool a vapor may comprise: a body, a mouthpiece, an aerosol outlet, a condenser with a condensation chamber, a heater, an oven with an oven chamber, a primary airflow inlet, and at least one aeration vent provided in the body, downstream of the oven, and upstream of the mouthpiece.

FIG. 1 shows an example of a vaporization device configured to rapidly cool a vapor. The device 100, may comprise a body 101. The body may house and/or integrate with one or more components of the device. The body may house and/or integrate with a mouthpiece 102. The mouthpiece 102 may have an aerosol outlet 122. A user may inhale the generated aerosol through the aerosol outlet 122 on the mouthpiece 102. The body may house and/or integrate with an oven region 104. The oven region 104 may comprise an oven chamber where vapor forming medium 106 may be placed. The vapor forming medium may include tobacco and/or botanicals, with or without a secondary humectant. In some cases the vapor forming medium may be contained in a removable and/or refillable cartridge.

Air may be drawn into the device through a primary air inlet 121. The primary air inlet 121 may be on an end of the device 100 opposite the mouthpiece 102. Alternatively, the primary air inlet 121 may be adjacent to the mouthpiece 102. In some cases, a pressure drop sufficient to pull air into the device through the primary air inlet 121 may be due to a user puffing on the mouthpiece 102.

The vapor forming medium (e.g., vaporizable material) may be heated in the oven chamber by a heater 105, to generate elevated temperature gas phases (vapor) of the tobacco or botanical and humectant/vapor forming components. The heater 105 may transfer heat to the vapor forming medium through conductive, convective, and/or radiative heat transfer. The generated vapor may be drawn out of the oven region and into the condensation chamber 103a, of the condenser 103 where the vapors may begin to cool and condense into micro-particles or droplets suspended in air, thus creating the initial formation of an aerosol, before being drawn out of the mouthpiece through the aerosol outlet 122.

In some cases, relatively cooler air may be introduced into the condensation chamber 103a, through an aeration vent 107 such that the vapor condenses more rapidly compared to a vapor in a device without the aeration vent 107. Rapidly cooling the vapor may create a denser aerosol cloud having particles with a diameter of average mass of less than or equal to about 1 micron, and depending on the mixture ratio of the vapor-forming humectant, particles with a diameter of average mass of less than or equal to about 0.5 micron Also described herein are devices for generating an inhalable aerosol said device comprising a body with a mouthpiece at one end, an attached body at the other end comprising a condensation chamber, a heater, an oven, wherein the oven comprises a first valve in the airflow path at the primary airflow inlet of the oven chamber, and a second valve at the outlet end of the oven chamber, and at least one aeration vent provided in the body, downstream of the oven, and upstream of the mouthpiece.

Figure 2:
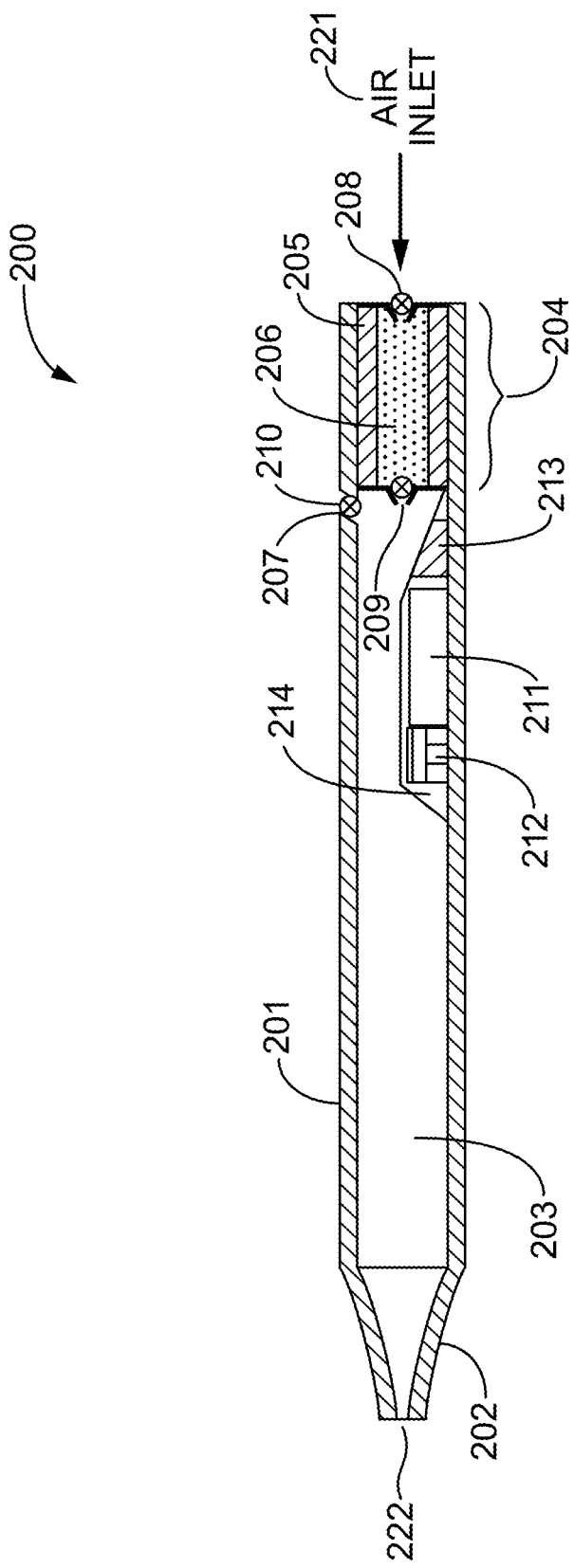
FIG. 2 is an illustrative cross-sectional view of an exemplary vaporization device with various electronic features and valves.

FIG. 2 shows a diagram of an alternative embodiment of the vaporization device 200. The vaporization device may have a body 201. The body 201 may integrate with and/or contain one or more components of the device. The body may integrate with or be connected to a mouthpiece 202

The body may comprise an oven region 204, with an oven chamber 204a having a first constricting valve 208 in the primary air inlet of the oven chamber and a second constricting valve 209 at the oven chamber outlet. The oven chamber 204a may be sealed with a tobacco or botanical and/or humectant/vapor forming medium 206 therein. The seal may be an air tight and/or liquid tight seal. The heater may be provided to the oven chamber with a heater 205. The heater 205 may be in thermal communication with the oven, for example the heater may be surrounding the oven chamber during the vaporization process. Heater may contact the oven. The heater may be wrapped around the oven. Before inhalation and before air is drawn in through a primary air inlet 221, pressure may build in the sealed oven chamber as heat is continually added. The pressure may build due to a phase change of the vaporizable material. Elevated temperature gas phases (vapor) of the tobacco or botanical and humectant/vapor forming components may be achieved by continually adding heat to the oven. This heated pressurization process may generate even higher saturation ratios when the valves 208, 209 are opened during inhalation. The higher saturation ratios may cause relatively higher particle concentrations of gas phase humectant in the resultant aerosol. When the vapor is drawn out of the oven region and into the condensation chamber 203a of the condenser 203, for example by inhalation by the user, the gas phase humectant vapors may be exposed to additional air through an aeration vent 207, and the vapors may begin to cool and condense into droplets suspended in air. As described previously the aerosol may be drawn through the mouthpiece 222 by the user. This condensation process may be further refined by adding an additional valve 210, to the aeration vent 207 to further control the air-vapor mixture process.

FIG. 2 also illustrates an exemplary embodiment of the additional components which would be found in a vaporizing device, including a power source or battery 211, a printed circuit board 212, a temperature regulator 213, and operational switches (not shown), housed within an internal electronics housing 214, to isolate them from the damaging effects of the moisture in the vapor and/or aerosol. The additional components may be found in a vaporizing device that may or may not comprise an aeration vent as described above.

In some embodiments of the vaporization device, components of the device are user serviceable, such as the power source or battery. These components may be replaceable or rechargeable.

Also described herein are devices for generating an inhalable aerosol said device comprising a first body, a mouthpiece having an aerosol outlet, a condensation chamber within a condenser and an airflow inlet and channel, an attached second body, comprising a heater and oven with an oven chamber, wherein said airflow channel is upstream of the oven and the mouthpiece outlet to provide airflow through the device, across the oven, and into the condensation chamber where an auxiliary aeration vent is provided.

Figure 3:
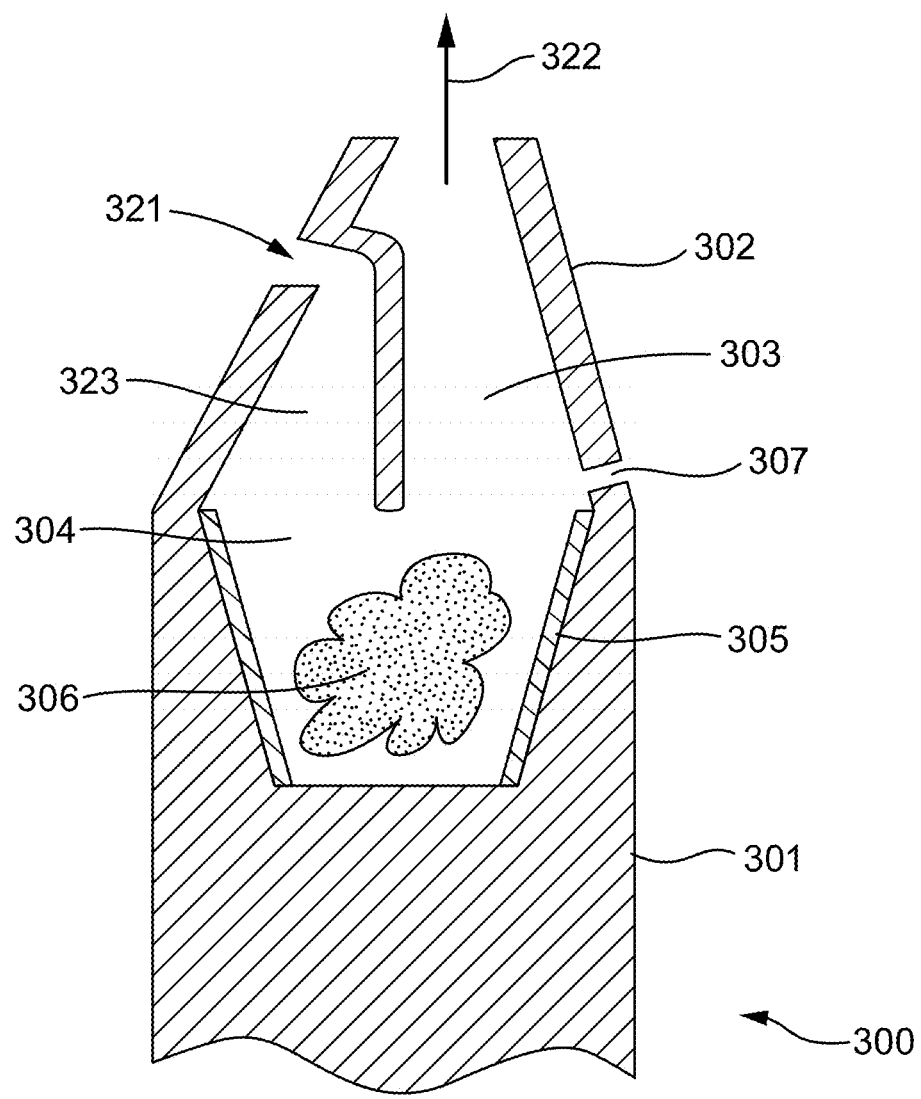
FIG. 3 is an illustrative sectional view of another exemplary vaporization device comprising a condensation chamber, air inlet and aeration vent in the mouthpiece.

FIG. 3 shows a section view of a vaporization device 300. The device 300 may comprise a body 301. The body may be connected to or integral with a mouthpiece 302 at one end. The mouthpiece may comprise a condensation chamber 303a within a condenser section 303 and an airflow inlet 321 and air channel 323. The device body may comprise a proximally located oven 304 comprising an oven chamber 304a. The oven chamber may be in the body of the device. A vapor forming medium 306 (e.g., vaporizable material) comprising tobacco or botanical and humectant vapor forming medium may be placed in the oven. The vapor forming medium may be in direct contact with an air channel 323 from the mouthpiece. The tobacco or botanical may be heated by heater 305 surrounding the oven chamber, to generate elevated temperature gas phases (vapor) of the tobacco or botanical and humectant/vapor forming components and air drawn in through a primary air inlet 321, across the oven, and into the condensation chamber 303a of the condenser region 303 due to a user puffing on the mouthpiece. Once in the condensation chamber where the gas phase humectant vapors begin to cool and condense into droplets suspended in air, additional air is allowed to enter through aeration vent 307, thus, once again creating a denser aerosol cloud having particles with a diameter of average mass of less than a typical vaporization device without an added aeration vent, before being drawn out of the mouthpiece through the aerosol outlet 322.

The device may comprises a mouthpiece comprising an aerosol outlet at a first end of the device and an air inlet that originates a first airflow path; an oven comprising an oven chamber that is in the first airflow path and includes the oven chamber and a heater for heating a vapor forming medium in the oven chamber and for forming a vapor therein, a condenser comprising a condensation chamber in which the vapor forms the inhalable aerosol, an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber through the aerosol outlet of the mouthpiece to a user.

The device may comprise a mouthpiece comprising an aerosol outlet at a first end of the device, an air inlet that originates a first airflow path, and an aeration vent that originates a second airflow path that allows air from the aeration vent to join the first airflow path; an oven comprising an oven chamber that is in the first airflow path and includes the oven chamber and a heater for heating a vapor forming medium in the oven chamber and for forming a vapor therein, a condenser comprising a condensation chamber in which the vapor forms the inhalable aerosol and wherein air from the aeration vent joins the first airflow path prior to or within the condensation chamber and downstream from the oven chamber thereby forming a joined path, wherein the joined path is configured to deliver the inhalable aerosol through the aerosol outlet of the mouthpiece to a user, as illustrated in exemplary FIG. 3.

The device may comprise a body with one or more separable components. For example, the mouthpiece may be separably attached to the body comprising the condensation chamber, a heater, and an oven, as illustrated in exemplary FIG. 1 or 2.

The device may comprise a body with one or more separable components. For example, the mouthpiece may be separably attached to the body. The mouthpiece may comprise the condensation chamber, and may be attached to or immediately adjacent to the oven and which is separable from the body comprising a heater, and the oven, as illustrated in exemplary FIG. 3.

The at least one aeration vent may be located in the condensation chamber of the condenser, as illustrated in exemplary FIG. 1, 2, or 3. The at least one aeration vent may comprise a third valve in the airflow path of the at least one aeration vent, as illustrated in exemplary FIG. 2. The first, second and third valve is a check valve, a clack valve, a non-return valve, or a one-way valve. In any of the preceding variations, the first, second or third valve may be mechanically actuated, electronically actuated or manually actuated. One skilled in the art will recognize after reading this disclosure that this device may be modified in a way such that any one, or each of these openings or vents could be configured to have a different combination or variation of mechanisms as described to control airflow, pressure and temperature of the vapor created and aerosol being generated by these device configurations, including a manually operated opening or vent with or without a valve.

The device may further comprise at least one of: a power source, a printed circuit board, a switch, and a temperature regulator. Alternately, one skilled in the art would recognize that each configuration previously described will also accommodate said power source (battery), switch, printed circuit board, or temperature regulator as appropriate, in the body.

The device may be disposable when the supply of prepackaged aerosol-forming media is exhausted. Alternatively, the device may be rechargeable such that the battery may be rechargeable or replaceable, and/or the aerosol-forming media may be refilled, by the user/operator of the device. Still further, the device may be rechargeable such that the battery may be rechargeable or replaceable, and/or the operator may also add or refill a tobacco or botanical component, in addition to a refillable or replaceable aerosol-forming media to the device.

As illustrated in FIG. 1, 2 or 3, the vaporization device may comprise tobacco or a botanical heated in said oven chamber, wherein said tobacco or botanical further comprises humectants to produce an aerosol comprising gas phase components of the humectant and tobacco or botanical. The gas phase humectant and tobacco or botanical vapor produced by said heated aerosol forming media 106, 206, 306 may further be mixed with air from a special aeration vent 107, 207, 307 after exiting the oven area 104, 204, 304 and entering a condensation chamber 103a, 203a, 303a to cool and condense said gas phase vapors to produce a far denser, thicker aerosol comprising more particles than would have otherwise been produced without the extra cooling air, with a diameter of average mass of less than or equal to about 1 micron.

Each aerosol configuration produced by mixing the gas phase vapors with the cool air may comprise a different range of particles, for example; with a diameter of average mass of less than or equal to about 0.9 micron; less than or equal to about 0.8 micron; less than or equal to about 0.7 micron; less than or equal to about 0.6 micron; and even an aerosol comprising particle diameters of average mass of less than or equal to about 0.5 micron.

The possible variations and ranges of aerosol density are great in that the possible number of combinations of temperature, pressure, tobacco or botanical choices and humectant selections are numerous. However, by excluding the tobacco or botanical choices and limiting the temperatures ranges and the humectant ratios to those described herein, the inventor has demonstrated that this device will produce a far denser, thicker aerosol comprising more particles than would have otherwise been produced without the extra cooling air, with a diameter of average mass of less than or equal to about 1 micron.

The humectant may comprise glycerol or vegetable glycerol as a vapor-forming medium.

The humectant may comprise propylene glycol as a vapor-forming medium.

In preferred embodiments, the humectant may comprise a ratio of vegetable glycerol to propylene glycol as a vapor-forming medium. The ranges of said ratio may vary between a ratio of about 100:0 vegetable glycerol to propylene glycol and a ratio of about 50:50 vegetable glycerol to propylene glycol. The difference in preferred ratios within the above stated range may vary by as little as 1, for example, said ratio may be about 99:1 vegetable glycerol to propylene glycol. However, more commonly said ratios would vary in increments of about 5, for example, about 95:5 vegetable glycerol to propylene glycol; or about 85:15 vegetable glycerol to propylene glycol; or about 55:45 vegetable glycerol to propylene glycol.

In a preferred embodiment the ratio for the vapor forming medium will be between the ratios of about 80:20 vegetable glycerol to propylene glycol, and about 60:40 vegetable glycerol to propylene glycol.

In a most preferred embodiment, the ratio for the vapor forming medium will be about 70:30 vegetable glycerol to propylene glycol.

In any of the preferred embodiments, the humectant may further comprise flavoring products. These flavorings may include enhancers comprising cocoa solids, licorice, tobacco or botanical extracts, and various sugars, to name but a few.

The tobacco or botanical may be heated in the oven up to its pyrolytic temperature, which as noted previously is most commonly measured in the range of 300-1000° C.

In preferred embodiments, the tobacco or botanical is heated to about 300° C. at most. In other preferred embodiments, the tobacco or botanical is heated to about 200° C. at most. In still other preferred embodiments, the tobacco or botanical is heated to about 160° C. at most. It should be noted that in these lower temperature ranges (<300° C.), pyrolysis of tobacco or botanical does not typically occur, yet vapor formation of the tobacco or botanical components and flavoring products does occur. In addition, vapor formation of the components of the humectant, mixed at various ratios will also occur, resulting in nearly complete vaporization, depending on the temperature, since propylene glycol has a boiling point of about 180°-190° C. and vegetable glycerin will boil at approximately 280°-290° C.

In still other preferred embodiments, the aerosol produced by said heated tobacco or botanical and humectant is mixed with air provided through an aeration vent.

In still other preferred embodiments, the aerosol produced by said heated tobacco or botanical and humectant mixed with air, is cooled to a temperature of about 50°-70° C. at most, and even as low as 35° C. before exiting the mouthpiece, depending on the air temperature being mixed into the condensation chamber. In some embodiments, the temperature is cooled to about 35°-55° C. at most, and may have a fluctuating range of ±about 10° C. or more within the overall range of about 35°-70° C.

Also described herein are vaporization devices for generating an inhalable aerosol comprising a unique oven configuration, wherein said oven comprises an access lid and an auxiliary aeration vent located within the airflow channel immediately downstream of the oven and before the aeration chamber. In this configuration, the user may directly access the oven by removing the access lid, providing the user with the ability to recharge the device with vaporization material.

In addition, having the added aeration vent in the airflow channel immediately after the oven and ahead of the vaporization chamber provides the user with added control over the amount of air entering the aeration chamber downstream and the cooling rate of the aerosol before it enters the aeration chamber.

Figure 4A:
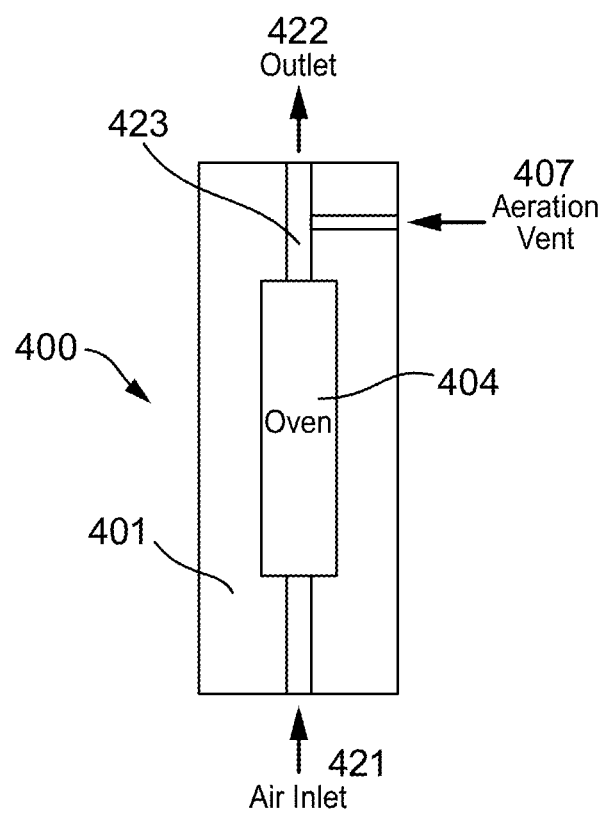
FIGS. 4A-4C is an illustrative example of an oven section of another exemplary vaporization device configuration with a access lid, comprising an oven having an air inlet, air outlet, and an additional aeration vent in the airflow pathway, after the oven.
Figure 4B:
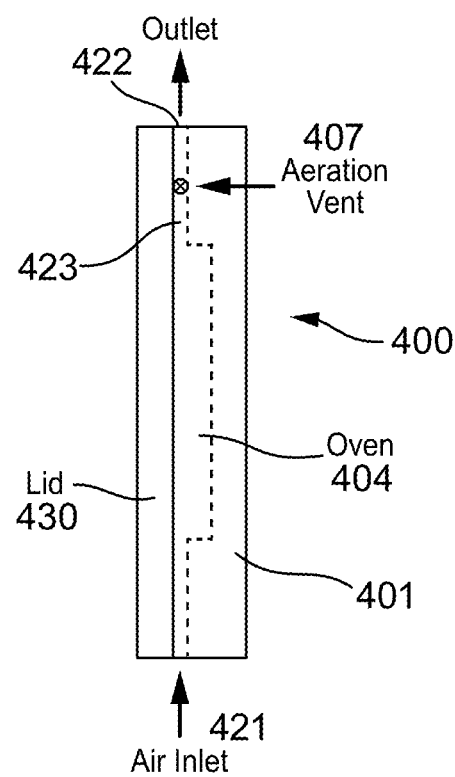
Figure 4C:
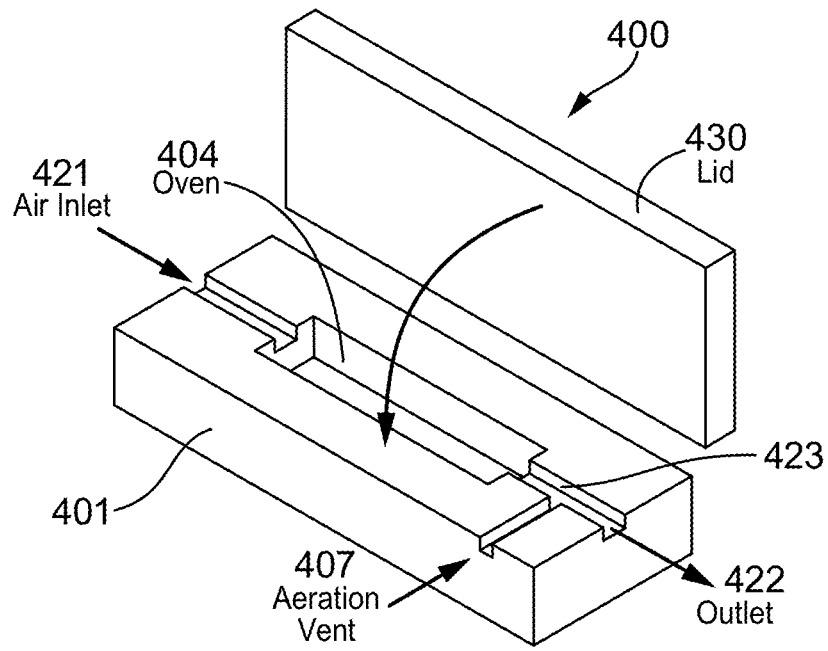

As noted in FIGS. 4A-4C, the device 400 may comprise a body 401, having an air inlet 421 allowing initial air for the heating process into the oven region 404. After heating the tobacco or botanical, and humectant (heater not shown), the gas phase humectant vapor generated may travel down the airflow channel 423, passing the added aeration vent 407 wherein the user may selectively increase airflow into the heated vapor. The user may selectively increase and/or decrease the airflow to the heated vapor by controlling a valve in communication with the aeration vent 407. In some cases, the device may not have an aeration vent. Airflow into the heated vapor through the aeration vent may decrease the vapor temperature before exiting the airflow channel at the outlet 422, and increase the condensation rate and vapor density by decreasing the diameter of the vapor particles within the aeration chamber (not shown), thus producing a thicker, denser vapor compared to the vapor generated by a device without the aeration vent. The user may also access the oven chamber 404a to recharge or reload the device 400, through an access lid 430 provided therein, making the device user serviceable. The access lid may be provided on a device with or without an aeration vent.

Provided herein is a method for generating an inhalable aerosol, the method comprising: providing an vaporization device, wherein said device produces a vapor comprising particle diameters of average mass of about 1 micron or less, wherein the vapor is formed by heating a vapor forming medium in an oven chamber of the device to a first temperature below the pyrolytic temperature of the vapor forming medium, and cooling the vapor in a condensation chamber to a temperature below the first temperature, before exiting an aerosol outlet of said device.

In some embodiments the vapor may be cooled by mixing relatively cooler air with the vapor in the condensation chamber during the condensation phase, after leaving the oven, where condensation of the gas phase humectants occurs more rapidly due to high saturation ratios being achieved at the moment of aeration, producing a higher concentration of smaller particles, with fewer by-products, in a denser aerosol, than would normally occur in a standard vaporization or aerosol generating device.

In some embodiments, formation of an inhalable aerosol is a two-step process. The first step occurs in the oven where the tobacco or botanical and humectant blend is heated to an elevated temperature. At the elevated temperature, evaporation happens faster than at room temperature and the oven chamber fills with the vapor phase of the humectants. The humectant will continue to evaporate until the partial pressure of the humectant is equal to the saturation pressure. At this point, the gas is said to have a saturation ratio of 1 ($S=P_{partial}/P_{sat}$).

In the second step, the gas leaves the oven chamber, passes to a condensation chamber in a condenser and begins to cool. As the gas phase vapor cools, the saturation pressure also goes down, causing the saturation ratio to rise, and the vapor to condensate, forming droplets. When cooling air is introduced, the large temperature gradient between the two fluids mixing in a confined space leads to very rapid cooling, causing high saturation ratios, small particles, and higher concentrations of smaller particles, forming a thicker, denser vapor cloud.

Provided herein is a method for generating an inhalable aerosol comprising: a vaporization device having a body with a mouthpiece at one end, and an attached body at the other end comprising; a condenser with a condensation chamber, a heater, an oven with an oven chamber, and at least one aeration vent provided in the body, downstream of the oven, and upstream of the mouthpiece, wherein tobacco or botanical comprising a humectant is heated in said oven chamber to produce a vapor comprising gas phase humectants.

As previously described, a vaporization device having an auxiliary aeration vent located in the condensation chamber capable of supplying cool air (relative to the heated gas components) to the gas phase vapors and tobacco or botanical components exiting the oven region, may be utilized to provide a method for generating a far denser, thicker aerosol comprising more particles than would have otherwise been produced without the extra cooling air, with a diameter of average mass of less than or equal to about 1 micron.

In another aspect, provided herein is a method for generating an inhalable aerosol comprising: a vaporization device, having a body with a mouthpiece at one end, and an attached body at the other end comprising: a condenser with a condensation chamber, a heater, an oven with an oven chamber, wherein said oven chamber further comprises a first valve in the airflow path at the inlet end of the oven chamber, and a second valve at the outlet end of the oven chamber; and at least one aeration vent provided in said body, downstream of the oven, and upstream of the mouthpiece wherein tobacco or botanical comprising a humectant is heated in said oven chamber to produce a vapor comprising gas phase humectants.

As illustrated in exemplary FIG. 2, by sealing the oven chamber 204a with a tobacco or botanical and humectant vapor forming medium 206 therein, and applying heat with the heater 205 during the vaporization process, before inhalation and air is drawn in through a primary air inlet 221, the pressure will build in the oven chamber as heat is continually added with an electronic heating circuit generated through the combination of the battery 211, printed circuit board 212, temperature regulator 213, and operator controlled switches (not shown), to generate even greater elevated temperature gas phase humectants (vapor) of the tobacco or botanical and humectant vapor forming components. This heated pressurization process generates even higher saturation ratios when the valves 208, 209 are opened during inhalation, which cause higher particle concentrations in the resultant aerosol, when the vapor is drawn out of the oven region and into the condensation chamber 203*a*, where they are again exposed to additional air through an aeration vent 207, and the vapors begin to cool and condense into droplets suspended in air, as described previously before the aerosol is withdrawn through the mouthpiece 222. The inventor also notes that this condensation process may be further refined by adding an additional valve 210, to the aeration vent 207 to further control the air-vapor mixture process.

In some embodiments of any one of the inventive methods, the first, second and/or third valve is a one-way valve, a check valve, a clack valve, or a non-return valve. The first, second and/or third valve may be mechanically actuated. The first, second and/or third valve may be electronically actuated. The first, second and/or third valve may be automatically actuated. The first, second and/or third valve may be manually actuated either directly by a user or indirectly in response to an input command from a user to a control system that actuates the first, second and/or third valve.

In other aspects of the inventive methods, said device further comprises at least one of: a power source, a printed circuit board, or a temperature regulator.

In any of the preceding aspects of the inventive method, one skilled in the art will recognize after reading this disclosure that this method may be modified in a way such that any one, or each of these openings or vents could be configured to have a different combination or variation of mechanisms or electronics as described to control airflow, pressure and temperature of the vapor created and aerosol being generated by these device configurations, including a manually operated opening or vent with or without a valve.

The possible variations and ranges of aerosol density are great in that the possible number of temperature, pressure, tobacco or botanical choices and humectant selections and combinations are numerous. However, by excluding the tobacco or botanical choices and limiting the temperatures to within the ranges and the humectant ratios described herein, the inventor has demonstrated a method for generating a far denser, thicker aerosol comprising more particles than would have otherwise been produced without the extra cooling air, with a diameter of average mass of less than or equal to 1 micron.

In some embodiments of the inventive methods, the humectant comprises a ratio of vegetable glycerol to propylene glycol as a vapor-forming medium. The ranges of said ratio will vary between a ratio of about 100:0 vegetable glycerol to propylene glycol and a ratio of about 50:50 vegetable glycerol to propylene glycol. The difference in preferred ratios within the above stated range may vary by as little as 1, for example, said ratio may be about 99:1 vegetable glycerol to propylene glycol. However, more commonly said ratios would vary in increments of 5, for example, about 95:5 vegetable glycerol to propylene glycol; or about 85:15 vegetable glycerol to propylene glycol; or about 55:45 vegetable glycerol to propylene glycol.

Because vegetable glycerol is less volatile than propylene glycol, it will recondense in greater proportions. A humectant with higher concentrations of glycerol will generate a thicker aerosol. The addition of propylene glycol will lead to an aerosol with a reduced concentration of condensed phase particles and an increased concentration of vapor phase effluent. This vapor phase effluent is often perceived as a tickle or harshness in the throat when the aerosol is inhaled. To some consumers, varying degrees of this sensation may be desirable. The ratio of vegetable glycerol to propylene glycol may be manipulated to balance aerosol thickness with the right amount of "throat tickle."

In a preferred embodiment of the method, the ratio for the vapor forming medium will be between the ratios of about 80:20 vegetable glycerol to propylene glycol, and about 60:40 vegetable glycerol to propylene glycol.

In a most preferred embodiment of the method, the ratio for the vapor forming medium will be about 70:30 vegetable glycerol to propylene glycol. On will envision that there will be blends with varying ratios for consumers with varying preferences.

In any of the preferred embodiments of the method, the humectant further comprises flavoring products. These flavorings include enhancers such as cocoa solids, licorice, tobacco or botanical extracts, and various sugars, to name a few.

In some embodiments of the method, the tobacco or botanical is heated to its pyrolytic temperature.

In preferred embodiments of the method, the tobacco or botanical is heated to about 300° C. at most.

In other preferred embodiments of the method, the tobacco or botanical is heated to about 200° C. at most. In still other embodiments of the method, the tobacco or botanical is heated to about 160° C. at most.

As noted previously, at these lower temperatures, (<300° C.), pyrolysis of tobacco or botanical does not typically occur, yet vapor formation of the tobacco or botanical components and flavoring products does occur. As may be inferred from the data supplied by Baker et al., an aerosol produced at these temperatures is also substantially free from Hoffman analytes or at least 70% less Hoffman analytes than a common tobacco or botanical cigarette and scores significantly better on the Ames test than a substance generated by burning a common cigarette. In addition, vapor formation of the components of the humectant, mixed at various ratios will also occur, resulting in nearly complete vaporization, depending on the temperature, since propylene glycol has a boiling point of about 180°-190° C. and vegetable glycerin will boil at approximately 280°-290° C.

In any one of the preceding methods, said inhalable aerosol produced by tobacco or a botanical comprising a humectant and heated in said oven produces an aerosol comprising gas phase humectants is further mixed with air provided through an aeration vent.

In any one of the preceding methods, said aerosol produced by said heated tobacco or botanical and humectant mixed with air, is cooled to a temperature of about 50°-70° C., and even as low as 35° C., before exiting the mouthpiece. In some embodiments, the temperature is cooled to about 35°-55° C. at most, and may have a fluctuating range of ±about 10° C. or more within the overall range of about 35°-70° C.

In some embodiments of the method, the vapor comprising gas phase humectant may be mixed with air to produce an aerosol comprising particle diameters of average mass of less than or equal to about 1 micron.

In other embodiments of the method, each aerosol configuration produced by mixing the gas phase vapors with the cool air may comprise a different range of particles, for example; with a diameter of average mass of less than or equal to about 0.9 micron; less than or equal to about 0.8 micron; less than or equal to about 0.7 micron; less than or equal to about 0.6 micron; and even an aerosol comprising particle diameters of average mass of less than or equal to about 0.5 micron.

Cartridge Design and Vapor Generation from Material in Cartridge

In some cases, a vaporization device may be configured to generate an inhalable aerosol. A device may be a self-contained vaporization device. The device may comprise an elongated body which functions to complement aspects of a separable and recyclable cartridge with air inlet channels, air passages, multiple condensation chambers, flexible heater contacts, and multiple aerosol outlets. Additionally, the cartridge may be configured for ease of manufacture and assembly.

Provided herein is a vaporization device for generating an inhalable aerosol. The device may comprise a device body, a separable cartridge assembly further comprising a heater, at least one condensation chamber, and a mouthpiece. The device provides for compact assembly and disassembly of components with detachable couplings; overheat shut-off protection for the resistive heating element; an air inlet passage (an enclosed channel) formed by the assembly of the device body and a separable cartridge; at least one condensation chamber within the separable cartridge assembly; heater contacts; and one or more refillable, reusable, and/or recyclable components.

Figure 7A:
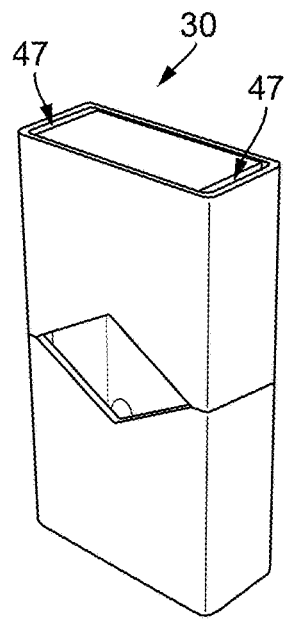
FIG. 7A is an illustrative isometric view of an assembled cartridge.

Provided herein is a device for generating an inhalable aerosol comprising: a device body comprising a cartridge receptacle; a cartridge comprising: a storage compartment, and a channel integral to an exterior surface of the cartridge, and an air inlet passage formed by the channel and an internal surface of the cartridge receptacle when the cartridge is inserted into the cartridge receptacle. The cartridge may be formed from a metal, plastic, ceramic, and/or composite material. The storage compartment may hold a vaporizable material. FIG. 7A shows an example of a cartridge 30 for use in the device. The vaporizable material may be a liquid at or near room temperature. In some cases the vaporizable material may be a liquid below room temperature. The channel may form a first side of the air inlet passage, and an internal surface of the cartridge receptacle may form a second side of the air inlet passage, as illustrated in various non-limiting aspects of FIGS. 5-6D, 7C, 8A, 8B, and 10A.

Provided herein is a device for generating an inhalable aerosol. The device may comprise a body that houses, contains, and or integrates with one or more components of the device. The device body may comprise a cartridge receptacle. The cartridge receptacle may comprise a channel integral to an interior surface of the cartridge receptacle; and an air inlet passage formed by the channel and an external surface of the cartridge when the cartridge is inserted into the cartridge receptacle. A cartridge may be fitted and/or inserted into the cartridge receptacle. The cartridge may have a fluid storage compartment. The channel may form a first side of the air inlet passage, and an external surface of the cartridge forms a second side of the air inlet passage. The channel may comprise at least one of: a groove; a trough; a track; a depression; a dent; a furrow; a trench; a crease; and a gutter. The integral channel may comprise walls that are either recessed into the surface or protrude from the surface where it is formed. The internal side walls of the channel may form additional sides of the air inlet passage. The channel may have a round, oval, square, rectangular, or other shaped cross section. The channel may have a closed cross section. The channel may be about 0.1 cm, 0.5 cm, 1 cm, 2 cm, or 5 cm wide. The channel may be about 0.1 mm, 0.5 mm, 1 mm, 2 mm, or 5 mm deep. The channel may be about 0.1 cm, 0.5 cm, 1 cm, 2 cm, or 5 cm long. There may be at least 1 channel.

In some embodiments, the cartridge may further comprise a second air passage in fluid communication with the air inlet passage to the fluid storage compartment, wherein the second air passage is formed through the material of the cartridge.

FIGS. 5-7C show various views of a compact electronic device 10 for generating an inhalable aerosol. The compact electronic device 10 may comprise a device body 20 with a cartridge receptacle 21 for receiving a cartridge 30. The device body may have a square or rectangular cross section. Alternatively, the cross section of the body may be any other regular or irregular shape. The cartridge receptacle may be shaped to receive an opened cartridge 30a or "pod". The cartridge may be opened when a protective cap is removed from a surface of the cartridge. In some cases, the cartridge may be opened when a hole or opening is formed on a surface of the cartridge. The opened cartridge 30a may be inserted into an open end of the cartridge receptacle 21 so that exposed heater contact tabs 33a on the first heater contacts 33 of the pod make contact with the second heater contacts 22 of the device body, thus forming the device 10.

Figure 14:
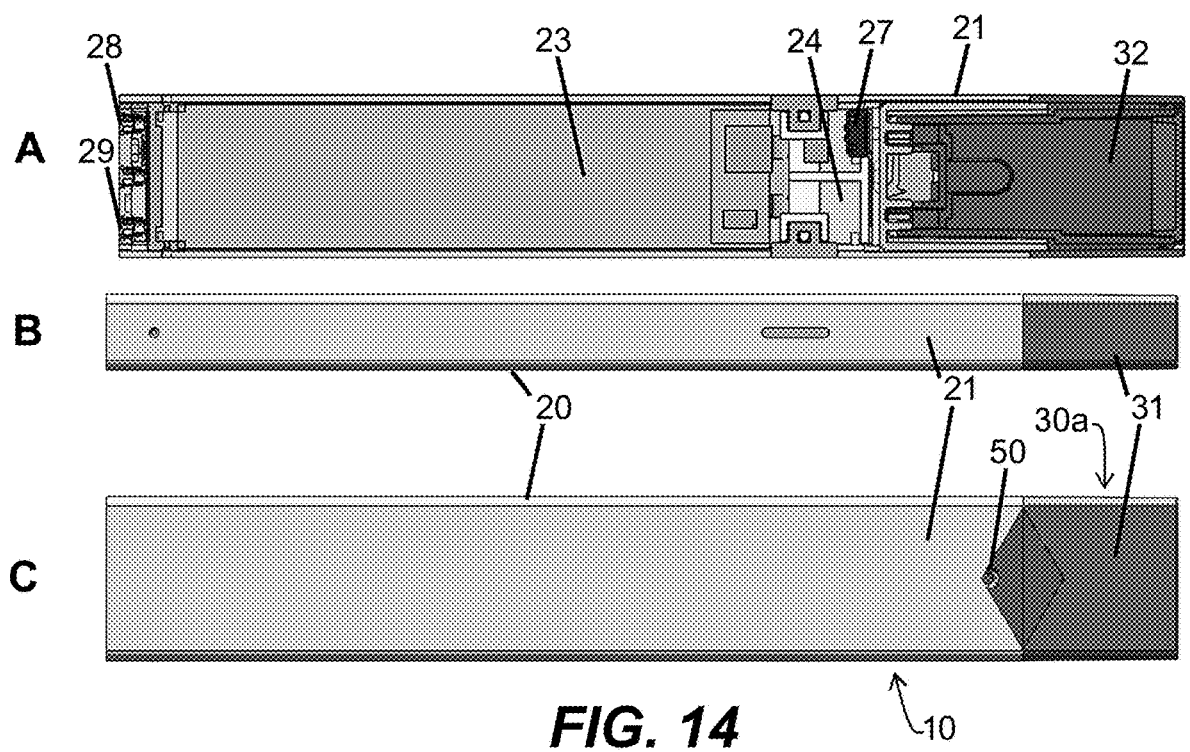
FIG. 14 illustrates front, side and section views of the assembled inhalable aerosol device.

Referring to FIG. 14, it is apparent in the plan view that when the pod 30a is inserted into the notched body of the cartridge receptacle 21, the channel air inlet 50 is left exposed. The size of the channel air inlet 50 may be varied by altering the configuration of the notch in the cartridge receptacle 21.

The device body may further comprise a rechargeable battery, a printed circuit board (PCB) 24 containing a microcontroller with the operating logic and software instructions for the device, a pressure sensor 27 for sensing the user's puffing action to activate the heater circuit, an indicator light 26, charging contacts (not shown), and an optional charging magnet or magnetic contact (not shown). The cartridge may further comprise a heater. The heater may be powered by the rechargeable battery. The temperature of the heater may be controlled by the microcontroller. The heater may be attached to a first end of the cartridge.

In some embodiments, the heater may comprise a heater chamber 37, a first pair of heater contacts 33, 33', a fluid wick 34, and a resistive heating element 35 in contact with the wick. The first pair of heater contacts may comprise thin plates affixed about the sides of the heater chamber. The fluid wick and resistive heating element may be suspended between the heater contacts.

In some embodiments, there may be two or more resistive heating elements 35, 35' and two or more wicks 34, 34'. In some of the embodiments, the heater contact 33 may comprise: a flat plate; a male contact; a female receptacle, or both; a flexible contact and/or copper alloy or another electrically conductive material. The first pair of heater contacts may further comprise a formed shape that may comprise a tab (e.g., flange) having a flexible spring value that extends out of the heater to complete a circuit with the device body. The first pair of heater contact may be a heat sink that absorb and dissipate excessive heat produced by the resistive heating element. Alternatively, the first pair of heater contacts may be a heat shield that protects the heater chamber from excessive heat produced by the resistive heating element. The first pair of heater contacts may be press-fit to an attachment feature on the exterior wall of the first end of the cartridge. The heater may enclose a first end of the cartridge and a first end of the fluid storage compartment.

Figure 7B:
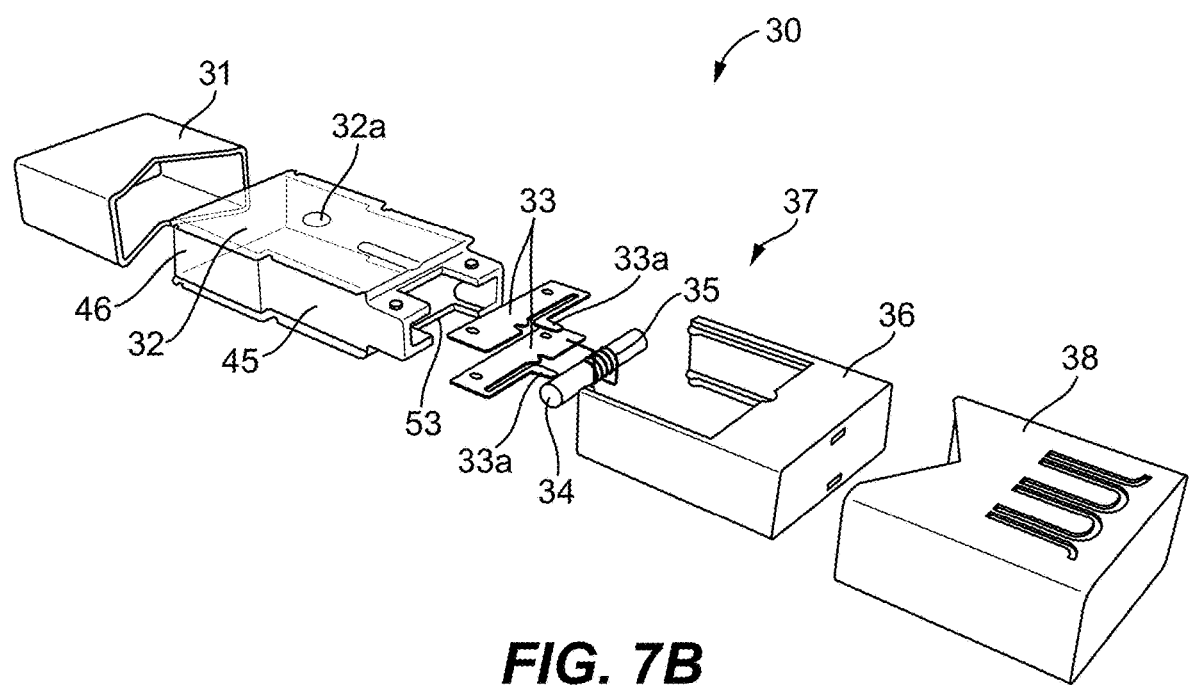
FIG. 7B is an illustrative exploded isometric view of a cartridge assembly.
Figure 7C:
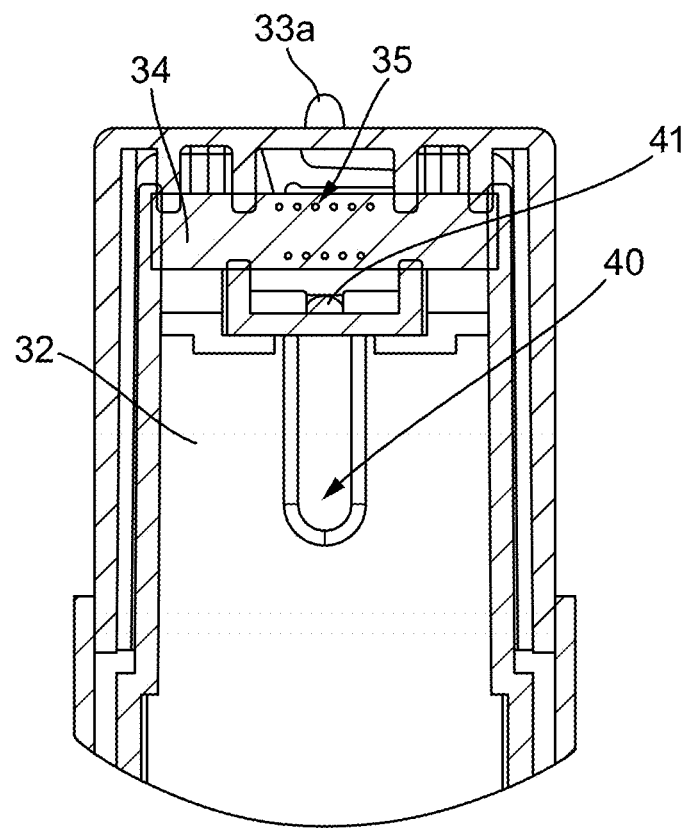
FIG. 7C is a side section view of FIG. 7A illustrating the inlet channel, inlet hole and relative placement of the wick, resistive heating element, and heater contacts, and the heater chamber inside of the heater.

As illustrated in the exploded assembly of FIG. 7B, a heater enclosure may comprises two or more heater contacts 33, each comprising a flat plate which may be machined or stamped from a copper alloy or similar electrically conductive material. The flexibility of the tip is provided by the cut-away clearance feature 33b created below the heater contact tabs 33a which capitalizes on the inherent spring capacity of the metal sheet or plate material. Another advantage and improvement of this type of contact is the reduced space requirement, simplified construction of a spring contact point (versus a pogo pin) and the easy of assembly. The heater may comprise a first condensation chamber. The heater may comprise more one or more additional condensation chambers in addition to the first condensation chamber. The first condensation chamber may be formed along an exterior wall of the cartridge.

In some cases, the cartridge (e.g., pod) is configured for ease of manufacturing and assembly. The cartridge may comprise an enclosure. The enclosure may be a tank. The tank may comprise an interior fluid storage compartment 32. The interior fluid storage compartment 32 which is open at one or both ends and comprises raised rails on the side edges 45b and 46b. The cartridge may be formed from plastic, metal, composite, and/or a ceramic material. The cartridge may be rigid or flexible.

The tank may further comprise a set of first heater contacts 33 formed from copper alloy or another electrically conductive material, having a thin cut-out 33b below the heater contact tabs 33a (to create a flexible tab) which are affixed to the sides of the first end of the tank and straddle the open-sided end 53 of the tank. The plates may affix to pins, or posts as shown in FIG. 7B or 5, or may be attached by other common means such as compression beneath the heater enclosure 36. A fluid wick 34 having a resistive heating element 35 wrapped around it, is placed between the first heater contacts 33, and attached thereto. A heater, comprising raised internal edges on the internal end (not shown), a thin mixing zone (not shown), and primary condensation channel covers 45a that slide over the rails 45b on the sides of the tank on the first half of the tank, creating a primary condensation channel/chamber 45. In addition, a small male snap feature 39b located at the end of the channel cover is configured fall into a female snap feature 39a, located mid-body on the side of the tank, creating a snap-fit assembly.

As will be further clarified below, the combination of the open-sided end 53, the heater contact tabs 33a of the heater contacts 33, the fluid wick 34 having a resistive heating element 35, enclosed in the open end of the fluid storage tank, under the heater enclosure 36, with a thin mixing zone therein, creates an efficient heater system. In addition, the primary condensation channel covers 45a which slide over the rails 45b on the sides of the tank create an integrated, easily assembled, primary condensation chamber 45, all within the heater at the first end of the cartridge 30 or opened cartridge 30a.

In some embodiments of the device, as illustrated in FIGS. 9A-9L, the heater may encloses at least a first end of the cartridge. The enclosed first end of the cartridge may include the heater and the interior fluid storage compartment. In some embodiments, the heater further comprises at least one first condensation chamber 45.

FIGS. 9A-9L show diagramed steps that mat be performed to assemble a cartomizer and/or mouthpiece. In 9A-9B the fluid storage compartment 32a may be oriented such that the heater inlet 53 faces upward. The heater contacts 33 may be inserted into the fluid storage compartment. Flexible heater contact tabs 33a may be inserted into the heater contacts 33. In a FIG. 9D the resistive heating element 35 may be wound on to the wick 34. In FIG. 9E the wick 34 and heater 35 may be placed on the fluid storage compartment. One or more free ends of the heater may sit outside the heater contacts. The one or more free ends may be soldered in place, rested in a groove, or snapped into a fitted location. At least a fraction of the one or more free ends may be in communication with the heater contacts 33. In a FIG. 9F the heater enclosure 36 may be snapped in place. The heater enclosure 36 may be fitted on the fluid storage compartment. FIG. 9G shows the heater enclosure 36 is in place on the fluid storage compartment. In FIG. 9H the fluid storage compartment can be flipped over. In FIG. 9I the mouthpiece 31 can be fitted on the fluid storage compartment. FIG. 9J shows the mouthpiece 31 in place on the fluid storage compartment. In FIG. 9K an end 49 can be fitted on the fluid storage compartment opposite the mouthpiece. FIG. 9L shows a fully assembled cartridge 30. FIG. 7B shows an exploded view of the assembled cartridge 30.

Depending on the size of the heater and/or heater chamber, the heater may have more than one wick 34 and resistive heating element 35.

In some embodiments, the first pair of heater contacts 33 further comprises a formed shape that comprises the heater contact tabs 33a having a flexible spring value that extends out of the heater. In some embodiments, the cartridge 30 comprises heater contacts 33 which are inserted into the cartridge receptacle 21 of the device body 20 wherein, the flexible heater contact tabs 33a insert into a second pair of heater contacts 22 to complete a circuit with the device body. The first pair of heater contacts 33 may be a heat sink that absorbs and dissipates excessive heat produced by the resistive heating element 35. The first pair of heater contacts 33 may be a heat shield that protects the heater chamber from excessive heat produced by the resistive heating element 35. The first pair of heater contacts may be press-fit to an attachment feature on the exterior wall of the first end of the cartridge. The heater may enclose a first end of the cartridge and a first end of the fluid storage compartment 32a. The heater may comprise a first condensation chamber 45. The heater may comprise at least one additional condensation chamber 45, 45', 45", etc. The first condensation chamber may be formed along an exterior wall of the cartridge.

In still other embodiments of the device, the cartridge may further comprise a mouthpiece 31, wherein the mouthpiece comprises at least one aerosol outlet channel/secondary condensation chamber 46; and at least one aerosol outlet 47. The mouthpiece may be attached to a second end of the cartridge. The second end of the cartridge with the mouthpiece may be exposed when the cartridge is inserted in the device. The mouthpiece may comprise more than one second condensation chamber 46, 46', 46", etc. The second condensation chamber is formed along an exterior wall of the cartridge.

The mouthpiece 31 may enclose the second end of the cartridge and interior fluid storage compartment. The partially assembled (e.g., mouthpiece removed) unit may be inverted and filled with a vaporizable fluid through the opposite, remaining (second) open end. Once filled, a snap-on mouthpiece 31 that also closes and seals the second end of the tank is inserted over the end. It also comprises raised internal edges (not shown), and aerosol outlet channel covers 46a that may slide over the rails 46b located on the sides of the second half of the tank, creating aerosol outlet channels/secondary condensation chambers 46. The aerosol outlet channels/secondary condensation chambers 46 slide over the end of primary condensation chamber 45, at a transition area 57, to create a junction for the vapor leaving the primary chamber and proceed out through the aerosol outlets 47, at the end of the aerosol outlet channels 46 and user-end of the mouthpiece 31.

The cartridge may comprise a first condensation chamber and a second condensation chamber 45, 46. The cartridge may comprise more than one first condensation chamber and more than one second condensation chamber 45, 46, 45', 46', etc.

In some embodiments of the device, a first condensation chamber 45 may be formed along the outside of the cartridge fluid storage compartment 31. In some embodiments of the device an aerosol outlet 47 exists at the end of aerosol outlet chamber 46. In some embodiments of the device, a first and second condensation chamber 45, 46 may be formed along the outside of one side of the cartridge fluid storage compartment 31. In some embodiments the second condensation chamber may be an aerosol outlet chamber. In some embodiments another pair of first and/or second condensation chambers 45', 46' is formed along the outside of the cartridge fluid storage compartment 31 on another side of the device. In some embodiments another aerosol outlet 47' will also exist at the end of the second pair of condensation chambers 45', 46'.

Figure 10A:
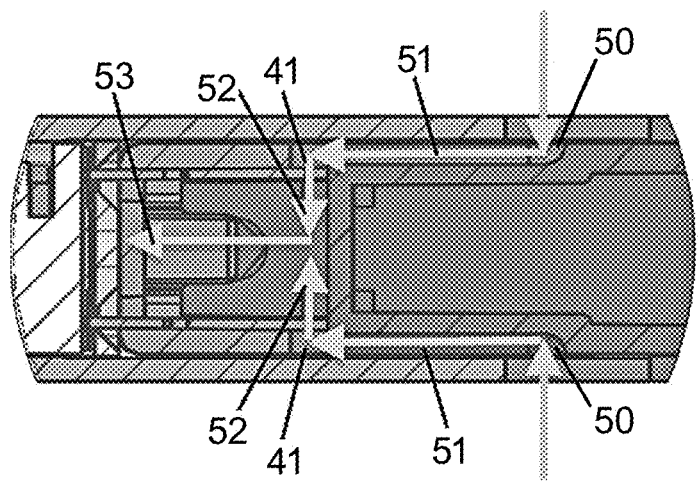
FIGS. 10A-10C are illustrative sequences showing the airflow/vapor path for the cartridge.
Figure 10B:
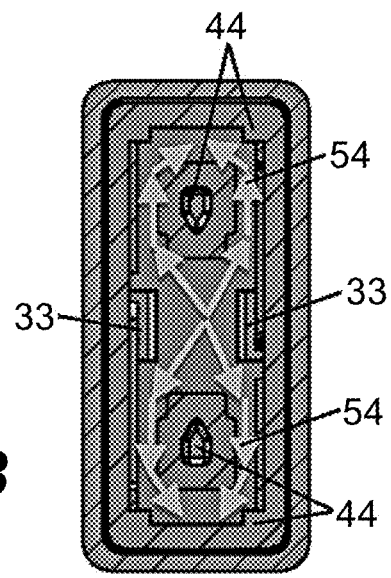
Figure 10C:
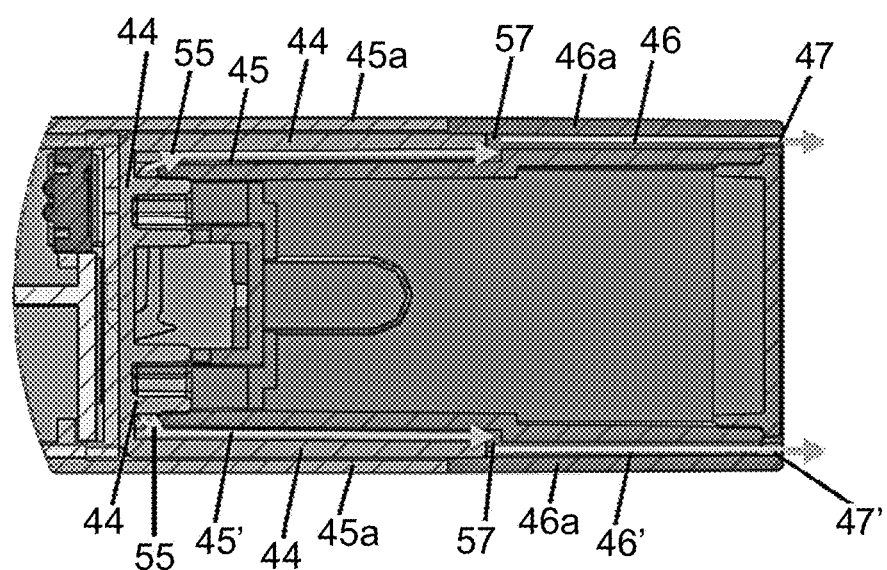
Figure 11:
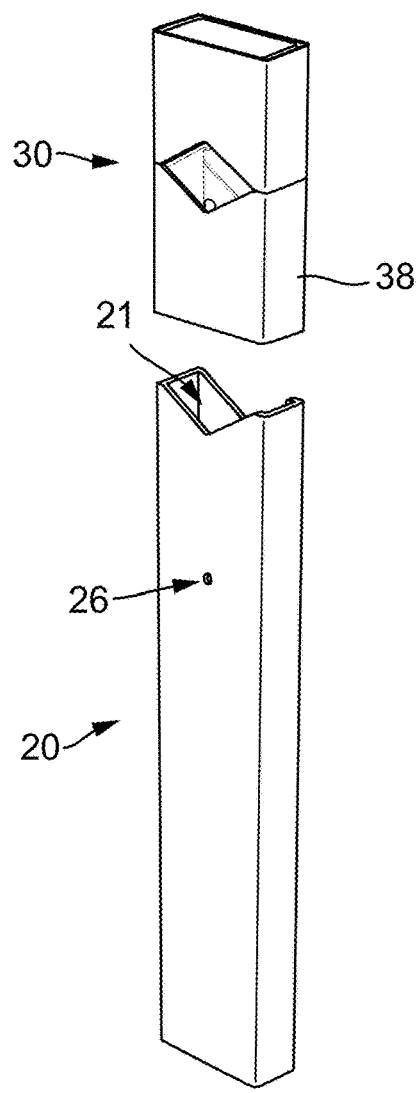
FIGS. 11, 12, and 13 represent an illustrative assembly sequence for assembling the main components of the device.
Figure 12:
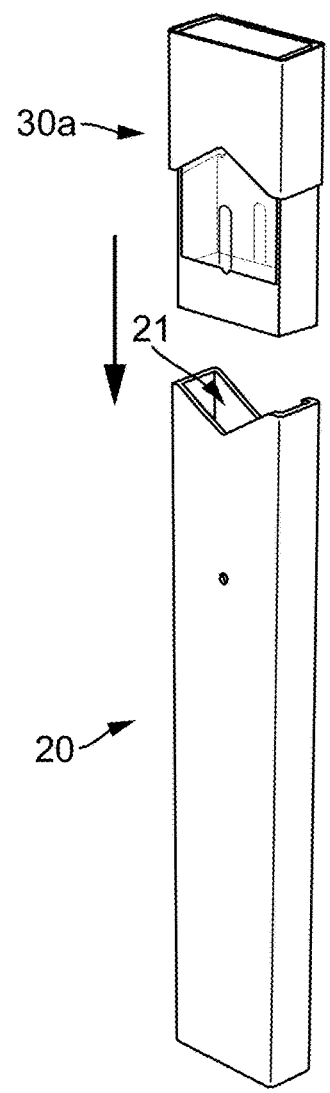

In any one of the embodiments, the first condensation chamber and the second condensation chamber may be in fluid communication as illustrated in FIG. 10C.

In some embodiments, the mouthpiece may comprise an aerosol outlet 47 in fluid communication with the second condensation chamber 46. The mouthpiece may comprise more than one aerosol outlet 47, 47' in fluid communication with more than one the second condensation chamber 46, 46'. The mouthpiece may enclose a second end of the cartridge and a second end of the fluid storage compartment.

In each of the embodiments described herein, the cartridge may comprise an airflow path comprising: an air inlet passage; a heater; at least a first condensation chamber; an aerosol outlet chamber, and an outlet port. In some of the embodiments described herein, the cartridge comprises an airflow path comprising: an air inlet passage; a heater; a first condensation chamber; a secondary condensation chamber; and an outlet port.

In still other embodiments described herein the cartridge may comprise an airflow path comprising at least one air inlet passage; a heater; at least one first condensation chamber; at least one secondary condensation chamber; and at least one outlet port.

Figure 8A:
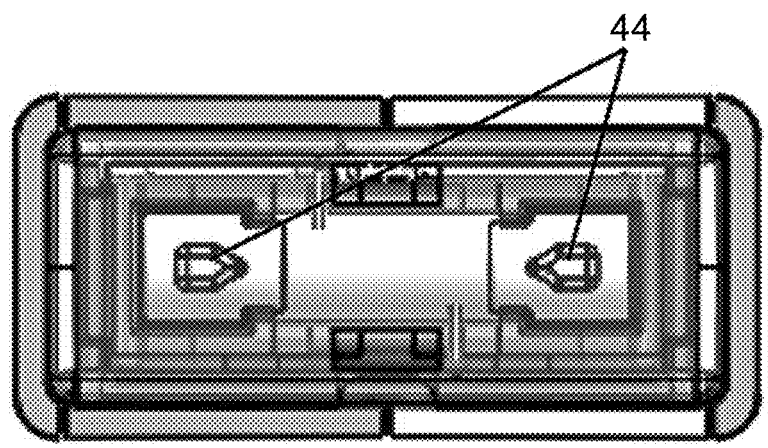
FIG. 8A is an illustrative end section view of an exemplary cartridge inside the heater.
Figure 8B:
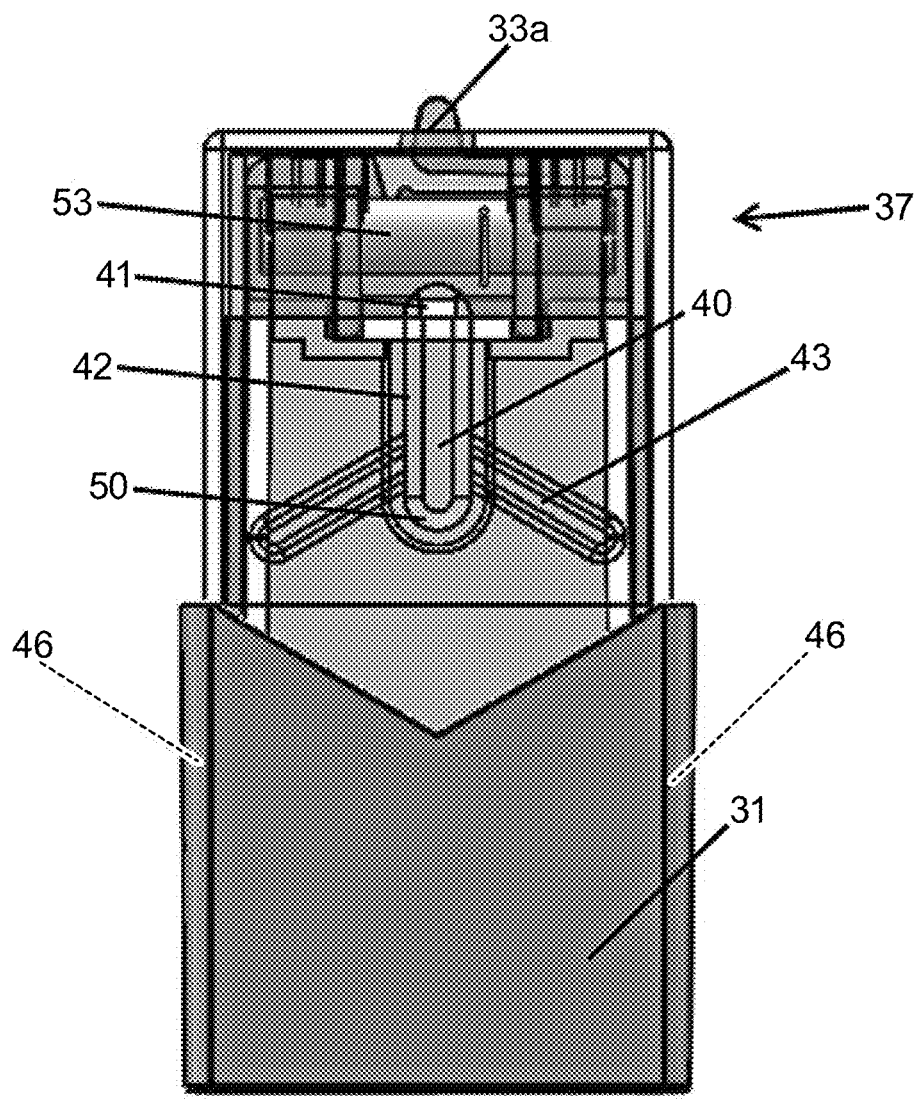
FIG. 8B is an illustrative side view of the cartridge with the cap removed and heater shown in shadow/outline.
Figure 9:
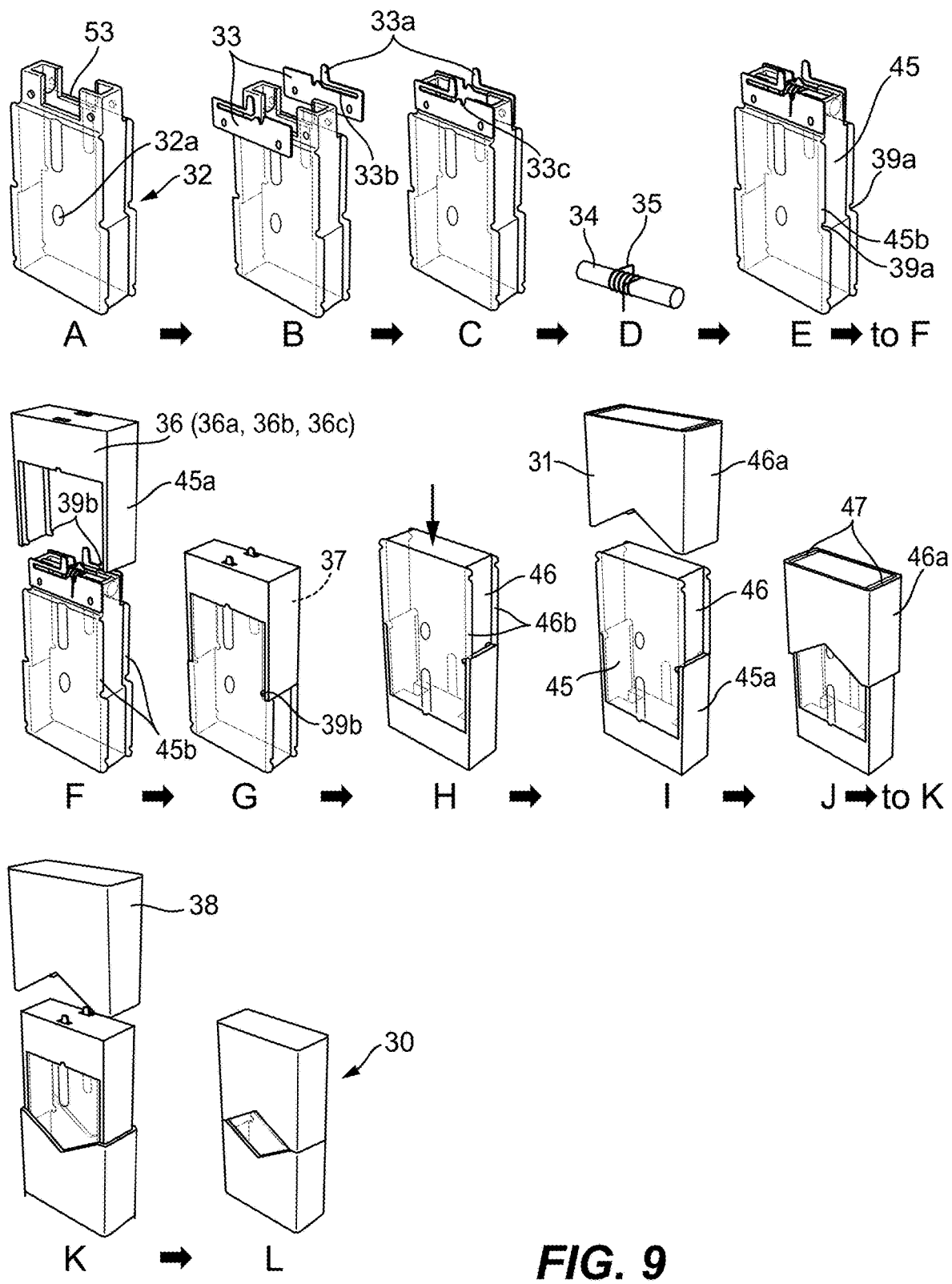
FIGS. 9A-9L illustrate an exemplary sequence of one assembly method for a cartridge.

As illustrated in FIGS. 10A-10C, an airflow path is created when the user draws on the mouthpiece 31 to create a suction (e.g., a puff), which essentially pulls air through the channel air inlet opening 50, through the air inlet passage 51, and into the heater chamber 37 through the second air passage (tank air inlet hole) 41 at the tank air inlet 52, then into the heater inlet 53. At this point, the pressure sensor has sensed the user's puff, and activated the circuit to the resistive heating element 35, which in turn, begins to generate vapor from the vapor fluid (e-juice). As air enters the heater inlet 53, it begins to mix and circulate in a narrow chamber above and around the wick 34 and between the heater contacts 33, generating heat, and dense, concentrated vapor as it mixes in the flow path 54 created by the sealing structure obstacles 44. FIG. 8A shows a detailed view of the sealing structure obstacles 44. Ultimately the vapor may be drawn, out of the heater along an air path 55 near the shoulder of the heater and into the primary condensation chamber 45 where the vapor expands and begins to cool. As the expanding vapor moves along the airflow path, it makes a transition from the primary condensation chamber 45 through a transition area 57, creating a junction for the vapor leaving the primary chamber, and entering the second vapor chamber 46, and proceeds out through the aerosol outlets 47, at the end of the mouthpiece 31 to the user.

As illustrated in FIGS. 10A-10C, the device may have a dual set of air inlet passages 50-53, dual first condensation chambers 55/45, dual second condensation chambers and aeration channels 57/46, and/or dual aerosol outlet vents 47.

Alternatively, the device may have an airflow path comprising: an air inlet passage 50, 51; a second air passage 41; a heater chamber 37; a first condensation chamber 45; a second condensation chamber 46; and/or an aerosol outlet 47.

In some cases, the devise may have an airflow path comprising: more than one air inlet passage; more than one second air passage; a heater chamber; more than one first condensation chamber; more than one second condensation chamber; and more than one aerosol outlet as clearly illustrated in FIGS. 10A-10C.

In any one of the embodiments described herein, the heater may be in fluid communication with the internal fluid storage compartment 32*a*.

In each of the embodiments described herein, the fluid storage compartment 32 is in fluid communication with the heater chamber 37, wherein the fluid storage compartment is capable of retaining condensed aerosol fluid, as illustrated in FIGS. 10A, 10C and 14.

In some embodiments of the device, the condensed aerosol fluid may comprise a nicotine formulation. In some embodiments, the condensed aerosol fluid may comprise a humectant. In some embodiments, the humectant may comprise propylene glycol. In some embodiments, the humectant may comprise vegetable glycerin.

In some cases, the cartridge may be detachable from the device body. In some embodiments, the cartridge receptacle and the detachable cartridge may form a separable coupling. In some embodiments the separable coupling may comprise a friction assembly. As illustrated in FIGS. 11-14, the device may have a press-fit (friction) assembly between the cartridge pod 30*a* and the device receptacle. Additionally, a dent/friction capture such as 43 may be utilized to capture the pod 30*a* to the device receptacle or to hold a protective cap 38 on the pod, as further illustrated in FIG. 8B.

In other embodiments, the separable coupling may comprise a snap-fit or snap-lock assembly. In still other embodiments the separable coupling may comprise a magnetic assembly.

In any one of the embodiments described herein, the cartridge components may comprise a snap-fit or snap-lock assembly, as illustrated in FIG. 5. In any one of the embodiments, the cartridge components may be reusable, refillable, and/or recyclable. The design of these cartridge components lend themselves to the use of such recyclable plastic materials as polypropylene, for the majority of components.

In some embodiments of the device 10, the cartridge 30 may comprise: a fluid storage compartment 32; a heater affixed to a first end with a snap-fit coupling 39*a*, 39*b*; and a mouthpiece 31 affixed to a second end with a snap-fit coupling 39*c*, 39*d* (not shown—but similar to 39*a* and 39*b*). The heater may be in fluid communication with the fluid storage compartment 32. The fluid storage compartment may be capable of retaining condensed aerosol fluid. The condensed aerosol fluid may comprise a nicotine formulation. The condensed aerosol fluid may comprise a humectant. The humectant may comprise propylene glycol and/or vegetable glycerin.

Provided herein is a device for generating an inhalable aerosol comprising: a device body 20 comprising a cartridge receptacle 21 for receiving a cartridge 30; wherein an interior surface of the cartridge receptacle forms a first side of an air inlet passage 51 when a cartridge comprising a channel integral 40 to an exterior surface is inserted into the cartridge receptacle 21, and wherein the channel forms a second side of the air inlet passage 51.

Provided herein is a device for generating an inhalable aerosol comprising: a device body 20 comprising a cartridge receptacle 21 for receiving a cartridge 30; wherein the cartridge receptacle comprises a channel integral to an interior surface and forms a first side of an air inlet passage when a cartridge is inserted into the cartridge receptacle, and wherein an exterior surface of the cartridge forms a second side of the air inlet passage 51.

Provided herein is a cartridge 30 for a device 10 for generating an inhalable aerosol comprising: a fluid storage compartment 32; a channel integral 40 to an exterior surface, wherein the channel forms a first side of an air inlet passage 51; and wherein an internal surface of a cartridge receptacle 21 in the device forms a second side of the air inlet passage 51 when the cartridge is inserted into the cartridge receptacle.

Provided herein is a cartridge 30 for a device 10 for generating an inhalable aerosol comprising a fluid storage compartment 32, wherein an exterior surface of the cartridge forms a first side of an air inlet channel 51 when inserted into a device body 20 comprising a cartridge receptacle 21, and wherein the cartridge receptacle further comprises a channel integral to an interior surface, and wherein the channel forms a second side of the air inlet passage 51.

In some embodiments, the cartridge further comprises a second air passage 41 in fluid communication with the channel 40, wherein the second air passage 41 is formed through the material of the cartridge 32 from an exterior surface of the cartridge to the internal fluid storage compartment 32a.

In some embodiments of the device body cartridge receptacle 21 or the cartridge 30, the integral channel 40 comprises at least one of: a groove; a trough; a depression; a dent; a furrow; a trench; a crease; and a gutter.

In some embodiments of the device body cartridge receptacle 21 or the cartridge 30, the integral channel 40 comprises walls that are either recessed into the surface or protrude from the surface where it is formed.

In some embodiments of the device body cartridge receptacle 21 or the cartridge 30, the internal side walls of the channel 40 form additional sides of the air inlet passage 51.

Provided herein is a device for generating an inhalable aerosol comprising: a cartridge comprising; a fluid storage compartment; a heater affixed to a first end comprising; a first heater contact, a resistive heating element affixed to the first heater contact; a device body comprising; a cartridge receptacle for receiving the cartridge; a second heater contact adapted to receive the first heater contact and to complete a circuit; a power source connected to the second heater contact; a printed circuit board (PCB) connected to the power source and the second heater contact; wherein the PCB is configured to detect the absence of fluid based on the measured resistance of the resistive heating element, and turn off the device.

Figure 13:
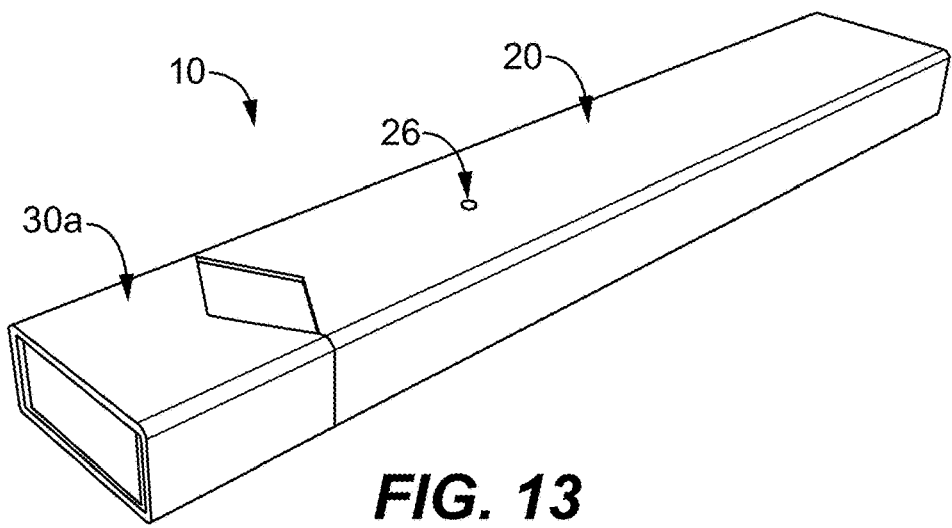
Figure 15:
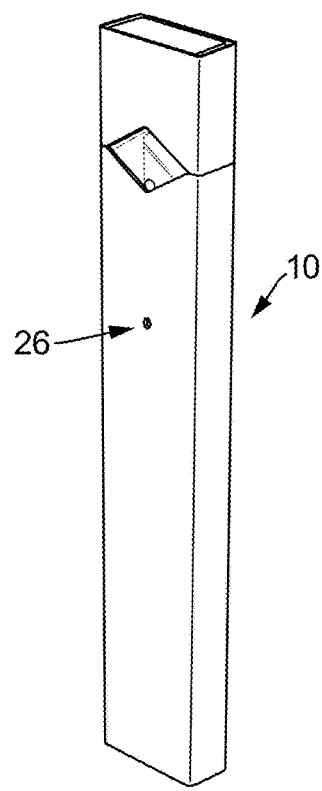
FIG. 15 is an illustrative view of an activated, assembled inhalable aerosol device.

Referring now to FIGS. 13, 14, and 15, in some embodiments, the device body further comprises at least one: second heater contact 22 (best shown in FIG. 6C detail); a battery 23; a printed circuit board 24; a pressure sensor 27; and an indicator light 26.

In some embodiments, the printed circuit board (PCB) further comprises: a microcontroller; switches; circuitry comprising a reference resistor; and an algorithm comprising logic for control parameters; wherein the microcontroller cycles the switches at fixed intervals to measure the resistance of the resistive heating element relative to the reference resistor, and applies the algorithm control parameters to control the temperature of the resistive heating element.

As illustrated in the basic block diagram of FIG. 17A, the device utilizes a proportional-integral-derivative controller or PID control law. A PID controller calculates an "error" value as the difference between a measured process variable and a desired SetPoint. When PID control is enabled, power to the coil is monitored to determine whether or not acceptable vaporization is occurring. With a given airflow over the coil, more power will be required to hold the coil at a given temperature if the device is producing vapor (heat is removed from the coil to form vapor). If power required to keep the coil at the set temperature drops below a threshold, the device indicates that it cannot currently produce vapor. Under normal operating conditions, this indicates that there is not enough liquid in the wick for normal vaporization to occur.

In some embodiments, the micro-controller instructs the device to turn itself off when the resistance exceeds the control parameter threshold indicating that the resistive heating element is dry.

In still other embodiments, the printed circuit board further comprises logic capable of detecting the presence of condensed aerosol fluid in the fluid storage compartment and is capable of turning off power to the heating contact(s) when the condensed aerosol fluid is not detected. When the microcontroller is running the PID temperature control algorithm 70, the difference between a set point and the coil temperature (error) is used to control power to the coil so that the coil quickly reaches the set point temperature, (e.g., between 200° C. and 400° C.). When the over-temperature algorithm is used, power is constant until the coil reaches an over-temperature threshold, (e.g., between 200° C. and 400° C.); (FIG. 17A applies: set point temperature is over-temperature threshold; constant power until error reaches 0).

The essential components of the device used to control the resistive heating element coil temperature are further illustrated in the circuit diagram of FIG. 17B. Wherein, BATT 23 is the battery; MCU 72 is the microcontroller; Q1 (76) and Q2 (77) are P-channel MOSFETs (switches); R_COIL 74 is the resistance of the coil. R_REF 75 is a fixed reference resistor used to measure R_COIL 74 through a voltage divider 73.

The battery powers the microcontroller. The microcontroller turns on Q2 for 1 ms every 100 ms so that the voltage between R_REF and R_COIL (a voltage divider) may be measured by the MCU at V_MEAS. When Q2 is off, the control law controls Q1 with PWM (pulse width modulation) to power the coil (battery discharges through Q1 and R_COIL when Q1 is on).

In some embodiments of the device, the device body further comprises at least one: second heater contact; a power switch; a pressure sensor; and an indicator light.

In some embodiments of the device body, the second heater contact 22 may comprise: a female receptacle; or a male contact, or both, a flexible contact; or copper alloy or another electrically conductive material.

In some embodiments of the device body, the battery supplies power to the second heater contact, pressure sensor, indicator light and the printed circuit board. In some embodiments, the battery is rechargeable. In some embodiments, the indicator light 26 indicates the status of the device and/or the battery or both.

In some embodiments of the device, the first heater contact and the second heater contact complete a circuit that allows current to flow through the heating contacts when the device body and detachable cartridge are assembled, which may be controlled by an on/off switch. Alternatively, the device can be turned on an off by a puff sensor. The puff sensor may comprise a capacitive membrane. The capacitive membrane may be similar to a capacitive membrane used in a microphone.

In some embodiments of the device, there is also an auxiliary charging unit for recharging the battery 23 in the device body. As illustrated in FIGS. 16A-16C, the charging unit 60, may comprise a USB device with a plug for a power source 63 and protective cap 64, with a cradle 61 for capturing the device body 20 (with or without the cartridge installed). The cradle may further comprise either a magnet or a magnetic contact 62 to securely hold the device body in place during charging. As illustrated in FIG. 6B, the device body further comprises a mating charging contact 28 and a magnet or magnetic contact 29 for the auxiliary charging unit. FIG. 16C is an illustrative example of the device body 20 being charged in a power source 65 (laptop computer or tablet).

In some cases the microcontroller on the PCB may be configured to monitor the temperature of the heater such that the vaporizable material is heated to a prescribed temperature. The prescribed temperature may be an input provided by the user. A temperature sensor may be in communication with the microcontroller to provide an input temperature to the microcontroller for temperature regulation. A temperature sensor may be a thermistor, thermocouple, thermometer, or any other temperature sensors. In some cases, the heating element may simultaneously perform as both a heater and a temperature sensor. The heating element may differ from a thermistor by having a resistance with a relatively lower dependence on temperature. The heating element may comprise a resistance temperature detector.

The resistance of the heating element may be an input to the microcontroller. In some cases, the resistance may be determined by the microcontroller based on a measurement from a circuit with a resistor with at least one known resistance, for example, a Wheatstone bridge. Alternatively, the resistance of the heating element may be measured with a resistive voltage divider in contact with the heating element and a resistor with a known and substantially constant resistance. The measurement of the resistance of the heating element may be amplified by an amplifier. The amplifier may be a standard op amp or instrumentation amplifier. The amplified signal may be substantially free of noise. In some cases, a charge time for a voltage divider between the heating element and a capacitor may be determined to calculate the resistance of the heating element. In some cases, the microcontroller must deactivate the heating element during resistance measurements. The resistance of the heating element may be a function of the temperature of the heating element such that the temperature may be directly determined from resistance measurements. Determining the temperature directly from the heating element resistance measurement rather than from an additional temperature sensor may generate a more accurate measurement because unknown contact thermal resistance between the temperature sensor and the heating element is eliminated. Additionally, the temperature measurement may be determined directly and therefore faster and without a time lag associated with attaining equilibrium between the heating element and a temperature sensor in contact with the heating element.

Figure 17C:
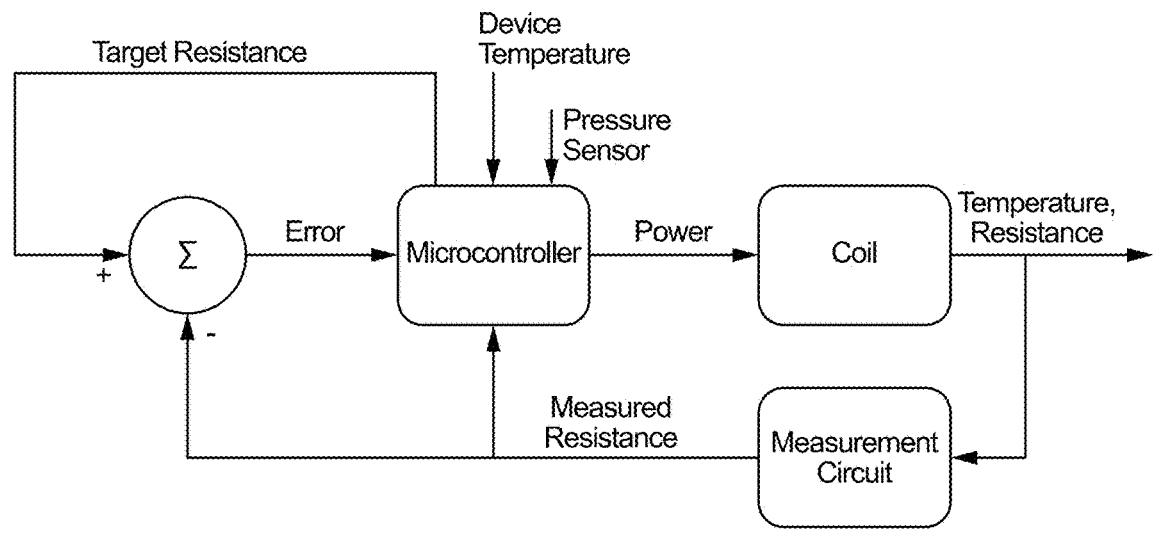
FIG. 17C is another example of a PID block diagram similar to that of FIG. 17A, in which the resistance of the resistive heater may be used to control the temperature of the apparatuses described herein.
Figure 17D:
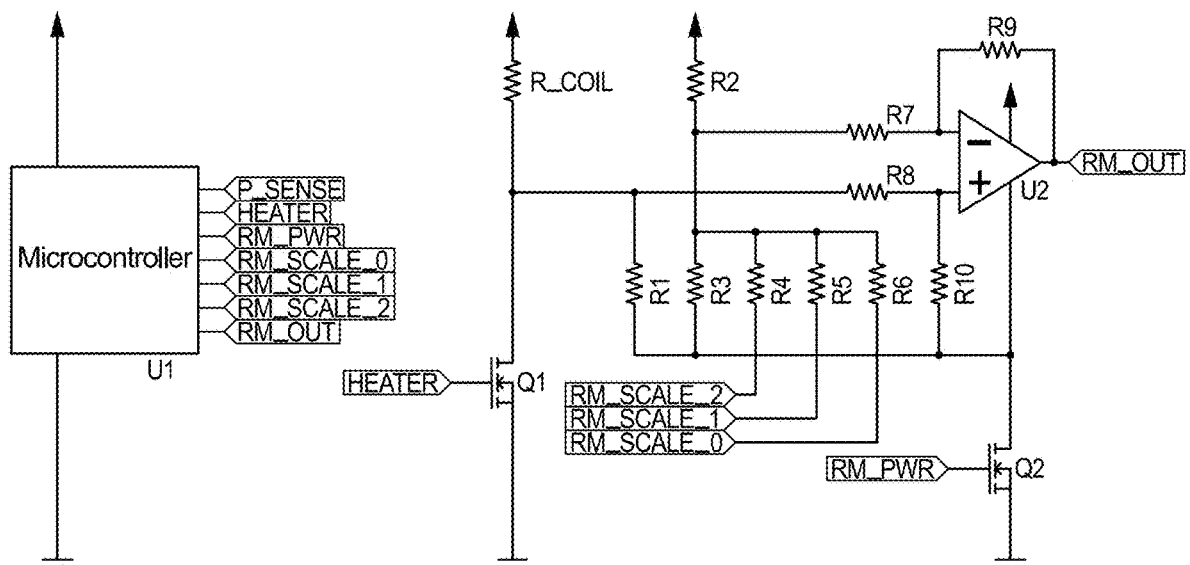
FIG. 17D is an example of a circuit showing one variation of the measurement circuit used in the PID block diagram shown in FIG. 17C. Specifically, this is an amplified Wheatstone bridge resistance measurement circuit.

FIG. 17C is another example of a PID control block diagram similar to that shown in FIG. 17A, and FIG. 17D is an example of a resistance measurement circuit used in this PID control scheme. In FIG. 17C, the block diagram includes a measurement circuit that can measure the resistance of the resistive heater (e.g., coil) and provide an analog signal to the microcontroller, a device temperature, which can be measured directly by the microcontroller and/or input into the microcontroller, and an input from a sensor (e.g., a pressure sensor, a button, or any other sensor) that may be used by the microcontroller to determine when the resistive heart should be heated, e.g., when the user is drawing on the device or when the device is scheduled to be set at a warmer temperature (e.g., a standby temperature).

In FIG. 17C, a signal from the measurement circuit goes directly to the microcontroller and to a summing block. In the measurement circuit, an example of which is shown in FIG. 17D (similar to the one shown in FIG. 17B), signal from the measurement circuit are fed directly to the microcontroller. The summing block in FIG. 17C is representative of the function which may be performed by the microcontroller when the device is heating; the summing block may show that error (e.g., in this case, a target Resistance minus a measured resistance of the resistive heater) is used by a control algorithm to calculate the power to be applied to the coil until the next coil measurement is taken.

In the example shown in FIGS. 17C-17D, signal from the measurement circuit may also go directly to the microcontroller in FIG. 17C; the resistive heater may be used to determine a baseline resistance (also referred to herein as the resistance of the resistive hater at an ambient temperature), when the device has not been heating the resistive heater, e.g., when some time has passed since the device was last heating. Alternatively or additionally, the baseline resistance may be determined by determining when coil resistance is changing with time at a rate that is below some stability threshold. Thus, resistance measurements of the coil may be used to determine a baseline resistance for the coil at ambient temperature.

A known baseline resistance may be used to calculate a target resistance that correlates to a target rise in coil temperature. The baseline (which may also be referred to as the resistance of the resistive heater at ambient temperature) may also be used to calculate the target resistance. The device temperature can be used to calculate an absolute target coil temperature as opposed to a target temperature rise. For example, a device temperature may be used to calculate absolute target coil temperature for more precise temperature control.

The circuit shown in FIG. 17B is one embodiment of a resistance measurement circuit comprising a voltage divider using a preset reference resistance. For the reference resistor approach (alternatively referred to as a voltage divider approach) shown in 17B, the reference resistor may be roughly the same resistance as the coil at target resistance (operating temperature). For example, this may be 1-2 Ohms. The circuit shown in FIG. 17D is another variation of a resistance measurement (or comparison) circuit. As before, in this example, the resistance of the heating element may be a function of the temperature of the heating element such that the temperature may be directly determined from resistance measurements. The resistance of the heating element is roughly linear with the temperature of the heating element.

In FIG. 17D, the circuit includes a Wheatstone bridge connected to a differential op amp circuit. The measurement circuit is powered when Q2 is held on via the RM_PWR signal from the microcontroller (RM=Resistance Measurement). Q2 is normally off to save battery life. In general, the apparatuses described herein stop applying power to the resistive heater to measure the resistance of the resistive heater. In FIG. 17D, when heating, the device must stop heating periodically (turn Q1 off) to measure coil resistance. One voltage divider in the bridge is between the Coil and R1, the other voltage divider is between R2 and R3 and optionally R4, R5, and R6. R4, R5, and R6 are each connected to open drain outputs from the microcontroller so that the R3 can be in parallel with any combination of R4, R5, and R6 to tune the R2/R3 voltage divider. An algorithm tunes the R2/R3 voltage divider via open drain control of RM_SCALE_0, RM_SCALE_1, and RM_SCALE_2 so that the voltage at the R2/R3 divider is just below the voltage of the R_COIL/R1 divider, so that the output of the op amp is between positive battery voltage and ground, which allows small changes in coil resistance to result in measureable changes in the op amp's output voltage. U2, R7, R8, R9, and R10 comprise the differential op amp circuit. As is standard in differential op amp circuits, R9/R7=R10/R8, R9>>R7, and the circuit has a voltage gain, A=R9/R7, such that the op amp outputs HM_OUT=A($V^+$-$V^-$) when 0≤A($V^+$-$V^-$) ≤V_BAT, where $V^+$ is the R_COIL/R1 divider voltage, $V^-$ is the tuned R2/R3 divider voltage, and V_BAT is the positive battery voltage.

In this example, the microcontroller performs an analog to digital conversion to measure HM_OUT, and then based on the values of R1 through R10 and the selected measurement scale, calculates resistance of the coil. When the coil has not been heated for some amount of time (e.g., greater than 10 sec, 20 sec, 30 sec, 1 min, 2 min, 3 min, 4 min, 5 min, 6 min, 7 min, 8 min, 9 min, 10 min, 15 min, 20 min, 30 min, etc.) and/or the resistance of the coil is steady, the microcontroller may save calculated resistance as the baseline resistance for the coil. A target resistance for the coil is calculated by adding a percentage change of baseline resistance to the baseline resistance. When the microcontroller detects via the pressure sensor that the user is drawing from the device, it outputs a PWM signal on HEATER to power the coil through Q1. PWM duty cycle is always limited to a max duty cycle that corresponds to a set maximum average power in the coil calculated using battery voltage measurements and coil resistance measurements. This allows for consistent heat-up performance throughout a battery discharge cycle. A PID control algorithm uses the difference between target coil resistance and measured coil resistance to set PWM duty cycle (limited by max duty cycle) to hold measured resistance at target resistance. The PID control algorithm holds the coil at a controlled temperature regardless of air flow rate and wicking performance to ensure a consistent experience (e.g., vaporization experience, including "flavor") across the full range of use cases and allow for higher power at faster draw rates. In general, the control law may update at any appropriate rate. For example, in some variations, the control law updates at 20 Hz. In this example, when heating, PWM control of Q1 is disabled and Q1 is held off for 2 ms every 50 ms to allow for stable coil resistance measurements. In another variation, the control law may update at 250-1000 Hz.

In the example shown in FIG. 17D, the number of steps between max and min measureable analog voltage may be controlled by the configuration. For example, precise temperature control (+/−1° C. or better) maybe achieved with a few hundred steps between measured baseline resistance and target resistance. In some variations, the number of steps may be approximately 4096. With variations in resistance between cartridges (e.g., +/−10% nominal coil resistance) and potential running changes to nominal cartridge resistance, it may be advantages to have several narrower measurement scales so that resistance can be measured at higher resolution than could be achieved if one fixed measurement scale had to be wide enough to measure all cartridges that a device might see. For example, R4, R5, and R6 may have values that allow for eight overlapping resistance measurement scales that allow for roughly five times the sensitivity of a single fixed scale covering the same range of resistances that are measurable by eight scales combined. More or less than eight measurement ranges may be used.

For example, in the variation shown in FIG. 17D, in some instances the measurement circuit may have a total range of 1.31-2.61 Ohm and a sensitivity of roughly 0.3 mOhm, which may allow for temperature setting increments and average coil temperature control to within +/−0.75° C. (e.g., a nominal coil resistance*TCR=1.5 Ohm*0.00014/° C.=0.21 mOhm/° C., 0.3 mOhm/(0.21 mOhm/° C.)=1.4° C. sensitivity). In some variations, R_COIL is 1.5 Ohm nominally, R1=100 Ohm, R2=162 Ohm, R3=10 kOhm, R4=28.7 kOhm, R5=57.6 kOhm, R6=115 kOhm, R7=R9=2 kOhm, R8=R10=698 kOhm.

As mentioned above, heater resistance is roughly linear with temperature. Changes in heater resistance may be roughly proportional to changes in temperature. With a coil at some resistance, $R_{baseline}$, at some initial temperature, $\Delta T=(R_{coil}/R_{baseline}-1)/TCR$ is a good approximation of coil temperature rise. Using an amplified Wheatstone bridge configuration similar to that shown in FIG. 17D, the device may calculate target resistance using baseline resistance and a fixed target percentage change in resistance, 4.0%. For coils with TCR of, as an example, 0.00014/° C., this may correspond to a 285° C. temperature rise (e.g., 0.04/(0.00014/° C.)=285° C.).

In general, the device doesn't need to calculate temperature; these calculations can be done beforehand, and the device can simply use a target percentage change in resistance to control temperature. For some baseline resistance, coil TCR, and target temperature change, target heater resistance may be: $R_{target}=R_{baseline}(1+TCR*\Delta T)$. Solved for $\Delta T$, this is $\Delta T=(R_{target}/R_{baseline}-1)/TCR$. Some device variations may calculate and provide (e.g., display, transmit, etc.) actual temperature so users can see actual temperatures during heat up or set a temperature in the device instead of setting a target percentage change in resistance.

Alternatively or additionally, the device may use measured ambient temperature and a target temperature (e.g., a temperature set point) to calculate a target resistance that corresponds to the target temperature. The target resistance may be determined from a baseline resistance at ambient temperature, coil TCR, target temperature, and ambient temperature. For example, a target heater resistance may be expressed as $R_{target}=R_{baseline}(1+TCR*(T_{set}-T_{amb}))$. Solved for $T_{set}$, this gives: $T_{set}=(R_{target}/R_{baseline}-1)/TCR+T_{amb}$. Some device variations may calculate and provide (e.g., display, transmit, etc.) actual temperature so users can see actual temperatures during heat up or set a temperature in the device instead of setting a target resistance or target percentage change in resistance.

For the voltage divider approach, if $R_{reference}$ is sufficiently close to $R_{baseline}$, temperature change is approximately $\Delta T=(R_{coil}/R_{reference}-R_{baseline}/R_{reference})/TCR$.

As mentioned above, any of the device variations described herein may be configured to control the temperature only after a sensor indicates that vaporization is required. For example, a pressure sensor (e.g., "puff sensor") may be used to determine when the coil should be heated. This sensor may function as essentially an on off switch for heating under PID control. Additionally, in some variations, the sensor may also control baseline resistance determination. For example baseline resistance may be prevented until at least some predetermined time period (e.g., 10 sec, 15 sec, 20 sec, 30 sec, 45 sec, 1 min, 2 min, etc.) after the last puff.

Provided herein is a device for generating an inhalable aerosol comprising: a cartridge comprising a first heater contact; a device body comprising; a cartridge receptacle for receiving the cartridge; a second heater contact adapted to receive the first heater contact and to complete a circuit; a power source connected to the second heater contact; a printed circuit board (PCB) connected to the power source and the second heater contact; and a single button interface; wherein the PCB is configured with circuitry and an algorithm comprising logic for a child safety feature.

In some embodiments, the algorithm requires a code provided by the user to activate the device. In some embodiments; the code is entered by the user with the single button interface. In still further embodiments the single button interface is the also the power switch.

Provided herein is a cartridge 30 for a device 10 for generating an inhalable aerosol comprising: a fluid storage compartment 32; a heater affixed to a first end comprising: a heater chamber 37, a first pair of heater contacts 33, a fluid wick 34, and a resistive heating element 35 in contact with the wick; wherein the first pair of heater contacts 33 comprise thin plates affixed about the sides of the heater chamber 37, and wherein the fluid wick 34 and resistive heating element 35 are suspended there between.

Depending on the size of the heater or heater chamber, the heater may have more than one wick 34, 34' and resistive heating element 35, 35'.

In some embodiments, the first pair of heater contacts further comprise a formed shape that comprises heater contact tabs 33a having a flexible spring value that extends out of the heater to complete a circuit with the device body 20.

In some embodiments, the heater contacts 33 are configured to mate with a second pair of heater contacts 22 in a cartridge receptacle 21 of the device body 20 to complete a circuit.

In some embodiments, the first pair of heater contacts is also a heat sink that absorbs and dissipates excessive heat produced by the resistive heating element.

In some embodiments, the first pair of heater contacts is a heat shield that protects the heater chamber from excessive heat produced by the resistive heating element.

Provided herein is a cartridge 30 for a device 10 for generating an inhalable aerosol comprising: a heater comprising; a heater chamber 37, a pair of thin plate heater contacts 33 therein, a fluid wick 34 positioned between the heater contacts 33, and a resistive heating element 35 in contact with the wick; wherein the heater contacts 33 each comprise a fixation site 33c wherein the resistive heating element 35 is tensioned there between.

As will be obvious to one skilled in the art after reviewing the assembly method illustrated in FIGS. 9A-9L, the heater contacts 33 simply snap or rest on locator pins on either side of the air inlet 53 on the first end of the cartridge interior fluid storage compartment, creating a spacious vaporization chamber containing the at least one wick 34 and at least one heating element 35.

Provided herein is a cartridge 30 for a device 10 for generating an inhalable aerosol comprising a heater attached to a first end of the cartridge.

In some embodiments, the heater encloses a first end of the cartridge and a first end of the fluid storage compartment 32, 32a.

In some embodiments, the heater comprises a first condensation chamber 45.

In some embodiments, the heater comprises more than one first condensation chamber 45, 45'.

In some embodiments, the condensation chamber is formed along an exterior wall of the cartridge 45b.

As noted previously, and described in FIGS. 10A, 10B and 10C, the airflow path through the heater and heater chamber generates vapor within the heater circulating air path 54, which then exits through the heater exits 55 into a first (primary) condensation chamber 45, which is formed by components of the tank body comprising the primary condensation channel/chamber rails 45b, the primary condensation channel cover 45a, (the outer side wall of the heater enclosure).

Provided herein is a cartridge 30 for a device 10 for generating an inhalable aerosol comprising a fluid storage compartment 32 and a mouthpiece 31, wherein the mouthpiece is attached to a second end of the cartridge and further comprises at least one aerosol outlet 47.

In some embodiments, the mouthpiece 31 encloses a second end of the cartridge 30 and a second end of the fluid storage compartment 32, 32a.

Additionally, as clearly illustrated in FIG. 10C in some embodiments the mouthpiece also contains a second condensation chamber 46 prior to the aerosol outlet 47, which is formed by components of the tank body 32 comprising the secondary condensation channel/chamber rails 46b, the second condensation channel cover 46a, (the outer side wall of the mouthpiece). Still further, the mouthpiece may contain yet another aerosol outlet 47' and another (second) condensation chamber 46' prior to the aerosol outlet, on another side of the cartridge.

In other embodiments, the mouthpiece comprises more than one second condensation chamber 46, 46'.

In some preferred embodiments, the second condensation chamber is formed along an exterior wall of the cartridge 46b.

In each of the embodiments described herein, the cartridge 30 comprises an airflow path comprising: an air inlet channel and passage 40, 41, 42; a heater chamber 37; at least a first condensation chamber 45; and an outlet port 47. In some of the embodiments described herein, the cartridge 30 comprises an airflow path comprising: an air inlet channel and passage 40, 41, 42; a heater chamber 37; a first condensation chamber 45; a second condensation chamber 46; and an outlet port 47.

In still other embodiments described herein the cartridge 30 may comprise an airflow path comprising at least one air inlet channel and passage 40, 41, 42; a heater chamber 37; at least one first condensation chamber 45; at least one second condensation chamber 46; and at least one outlet port 47.

In each of the embodiments described herein, the fluid storage compartment 32 is in fluid communication with the heater, wherein the fluid storage compartment is capable of retaining condensed aerosol fluid.

In some embodiments of the device, the condensed aerosol fluid comprises a nicotine formulation. In some embodiments, the condensed aerosol fluid comprises a humectant. In some embodiments, the humectant comprises propylene glycol. In some embodiments, the humectant comprises vegetable glycerin.

Provided herein is a cartridge 30 for a device 10 for generating an inhalable aerosol comprising: a fluid storage compartment 32; a heater affixed to a first end; and a mouthpiece 31 affixed to a second end; wherein the heater comprises a first condensation chamber 45 and the mouthpiece comprises a second condensation chamber 46.

In some embodiments, the heater comprises more than one first condensation chamber 45, 45' and the mouthpiece comprises more than one second condensation chamber 46, 46'.

In some embodiments, the first condensation chamber and the second condensation chamber are in fluid communication. As illustrated in FIG. 10C, the first and second condensation chambers have a common transition area 57, 57', for fluid communication.

In some embodiments, the mouthpiece comprises an aerosol outlet 47 in fluid communication with the second condensation chamber 46.

In some embodiments, the mouthpiece comprises two or more aerosol outlets 47, 47'.

In some embodiments, the mouthpiece comprises two or more aerosol outlets 47, 47' in fluid communication with the two or more second condensation chambers 46, 46'.

In any one of the embodiments, the cartridge meets ISO recycling standards.

In any one of the embodiments, the cartridge meets ISO recycling standards for plastic waste.

And in still other embodiments, the plastic components of the cartridge are composed of polylactic acid (PLA), wherein the PLA components are compostable and or degradable.

Provided herein is a device 10 for generating an inhalable aerosol comprising a device body 20 comprising a cartridge receptacle 21; and a detachable cartridge 30; wherein the cartridge receptacle and the detachable cartridge form a separable coupling, and wherein the separable coupling comprises a friction assembly, a snap-fit assembly or a magnetic assembly.

In other embodiments of the device, the cartridge is a detachable assembly. In any one of the embodiments described herein, the cartridge components may comprise a snap-lock assembly such as illustrated by snap features 39a and 39b. In any one of the embodiments, the cartridge components are recyclable.

Provided herein is a method of fabricating a device for generating an inhalable aerosol comprising: providing a device body comprising a cartridge receptacle; and providing a detachable cartridge; wherein the cartridge receptacle and the detachable cartridge form a separable coupling comprising a friction assembly, a snap-fit assembly or a magnetic assembly when the cartridge is inserted into the cartridge receptacle.

Provided herein is a method of making a device 10 for generating an inhalable aerosol comprising: providing a device body 20 with a cartridge receptacle 21 comprising one or more interior coupling surfaces 21a, 21b, 21c . . . ; and further providing a cartridge 30 comprising: one or more exterior coupling surfaces 36a, 36b, 36c, . . . , a second end and a first end; a tank 32 comprising an interior fluid storage compartment 32a; at least one channel 40 on at least one exterior coupling surface, wherein the at least one channel forms one side of at least one air inlet passage 51, and wherein at least one interior wall of the cartridge receptacle forms at least one side one side of at least one air inlet passage 51 when the detachable cartridge is inserted into the cartridge receptacle.

FIGS. 9A-9L provides an illustrative example of a method of assembling such a device.

In some embodiments of the method, the cartridge 30 is assembled with a protective removable end cap 38 to protect the exposed heater contact tabs 33a protruding from the heater.

Provided herein is a method of fabricating a cartridge for a device for generating an inhalable aerosol comprising: providing a fluid storage compartment; affixing a heater to a first end with a snap-fit coupling; and affixing a mouthpiece to a second end with a snap-fit coupling.

Provided herein is a cartridge 30 for a device 10 for generating an inhalable aerosol with an airflow path comprising: a channel 50 comprising a portion of an air inlet passage 51; a second air passage 41 in fluid communication with the channel; a heater chamber 37 in fluid communication with the second air passage; a first condensation chamber 45 in fluid communication with the heater chamber; a second condensation chamber 46 in fluid communication with the first condensation chamber; and an aerosol outlet 47 in fluid communication with second condensation chamber.

Provided herein is a device 10 for generating an inhalable aerosol adapted to receive a removable cartridge 30, wherein the cartridge comprises a fluid storage compartment or tank 32; an air inlet 41; a heater, a protective removable end cap 38, and a mouthpiece 31.

Charging

In some cases, the vaporization device may comprise a power source. The power source may be configured to provide power to a control system, one or more heating elements, one or more sensors, one or more lights, one or more indicators, and/or any other system on the electronic cigarette that requires a power source. The power source may be an energy storage device. The power source may be a battery or a capacitor. In some cases, the power source may be a rechargeable battery.

The battery may be contained within a housing of the device. In some cases the battery may be removed from the housing for charging. Alternatively, the battery may remain in the housing while the battery is being charged. Two or more charge contact may be provided on an exterior surface of the device housing. The two or more charge contacts may be in electrical communication with the battery such that the battery may be charged by applying a charging source to the two or more charge contacts without removing the battery from the housing.

Figure 18:
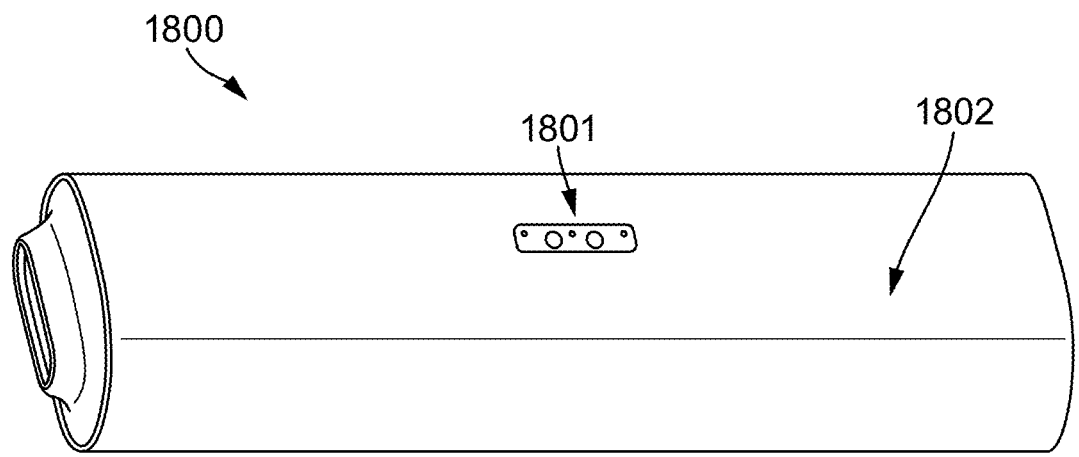
FIG. 18 is a device with charging contacts visible from an exterior housing of the device.

FIG. 18 shows a device 1800 with charge contacts 1801. The charge contacts 1801 may be accessible from an exterior surface of a device housing 1802. The charge contacts 1801 may be in electrical communication with an energy storage device (e.g., battery) inside of the device housing 1802. In some cases, the device housing may not comprise an opening through which the user may access components in the device housing. The user may not be able to remove the battery and/or other energy storage device from the housing. In order to open the device housing a user must destroy or permanently disengage the charge contacts. In some cases, the device may fail to function after a user breaks open the housing.

Figure 19:
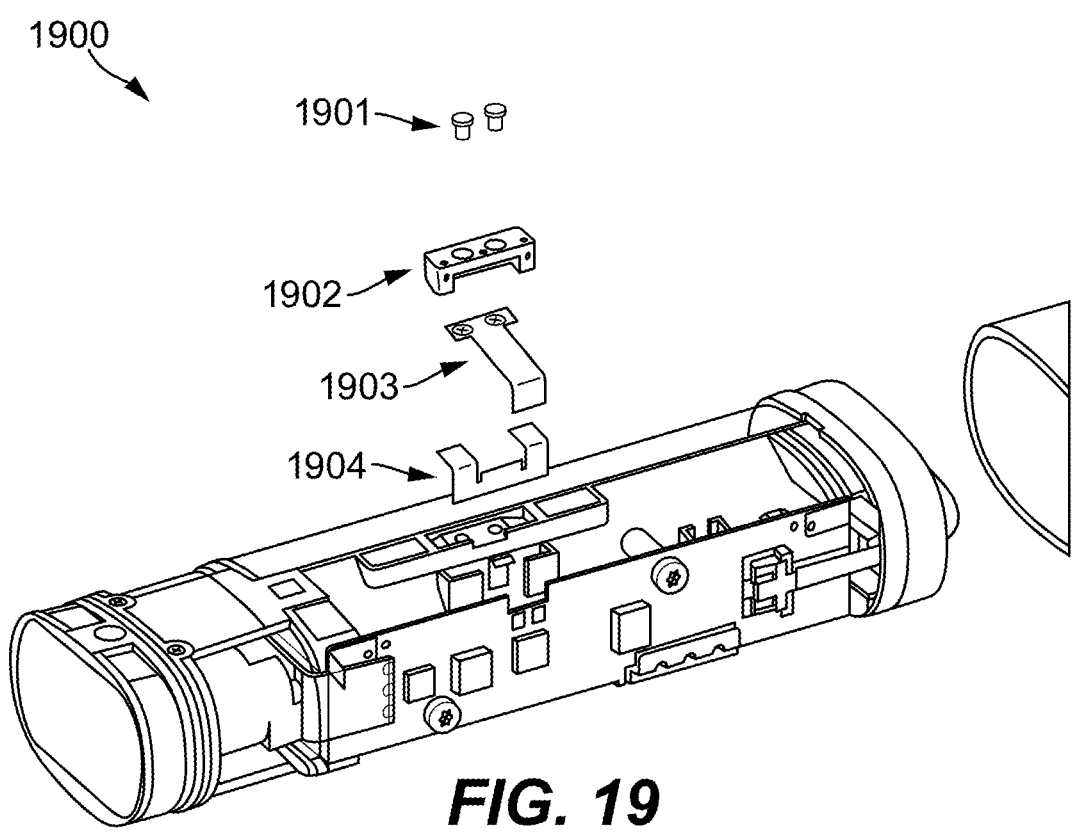
FIG. 19 is an exploded view of a charging assembly of a device.

FIG. 19 shows an exploded view of a charging assembly 1900 in an electronic vaporization device. The housing (not shown) has been removed from the exploded view in FIG.

19. The charge contact pins 1901 may be visible on the exterior of the housing. The charge contact pins 1901 may be in electrical communication with a power storage device of the electronic vaporization device. When the device is connected to a power source (e.g., during charging of the device) the charging pins may facilitate electrical communication between the power storage device inside of the electronic vaporization device and the power source outside of the housing of the vaporization device. The charge contact pins 1901 may be held in place by a retaining bezel 1902. The charge contact pins 1901 may be in electrical communication with a charger flex 1903. The charging pins may contact the charger flex such that a need for soldering of the charger pins to an electrical connection to be in electrical communication with the power source may be eliminated. The charger flex may be soldered to a printed circuit board (PCB). The charger flex may be in electrical communication with the power storage device through the PCB. The charger flex may be held in place by a bent spring retainer 1904.

Figure 20:
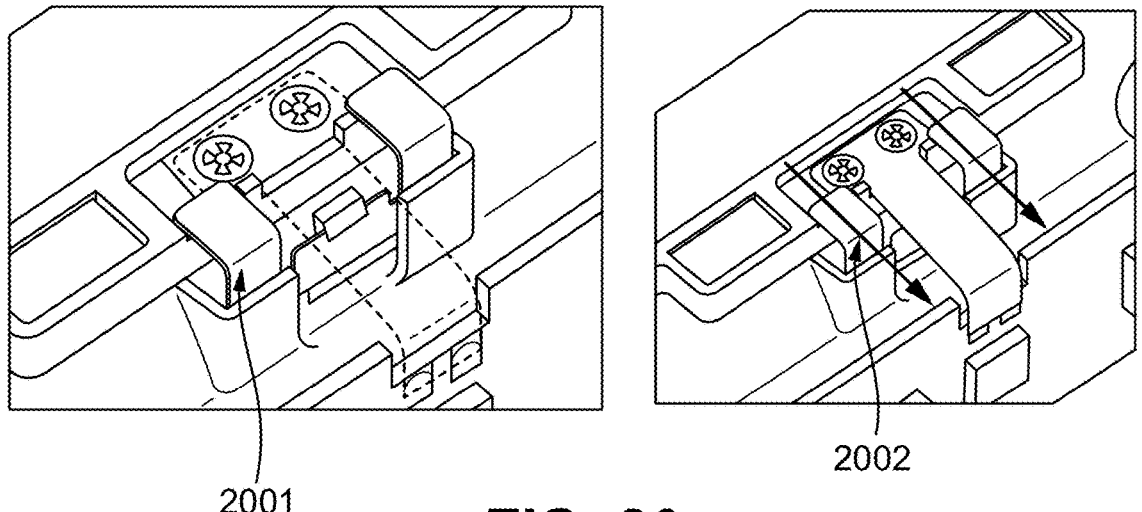
FIG. 20 is a detailed view of a charging assembly of a device.

FIG. 20 shows the bent spring retainer in an initial position 2001 and a deflected position 2002. The bent spring retainer may hold the retaining bezel in a fixed location. The bent spring retainer may deflect only in one direction when the charging assembly is enclosed in the housing of the electronic vaporization device.

Figure 21:
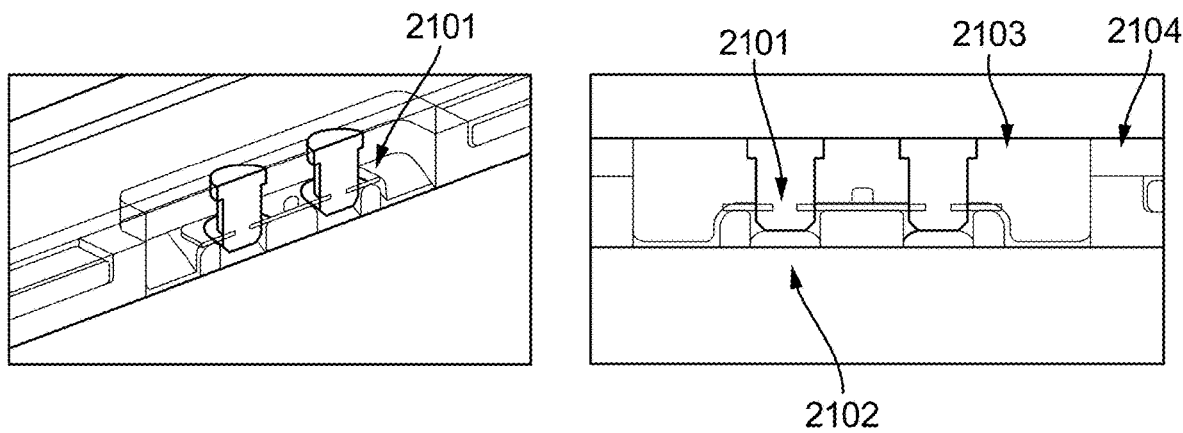
FIG. 21 is a detailed view of charging pins in a charging assembly of a device.

FIG. 21 shows a location of the charger pins 2101 when the electronic vaporization device is fully assembled with the charging pins 2101 contact the charging flex 2102. When the device is fully assembled at least a portion of the retaining bezel may be fitted in an indentation 2103 on the inside of the housing 2104. In some cases, disassembling the electronic vaporization device may destroy the bezel such that the device cannot be reassembled after disassembly.

Figure 22:
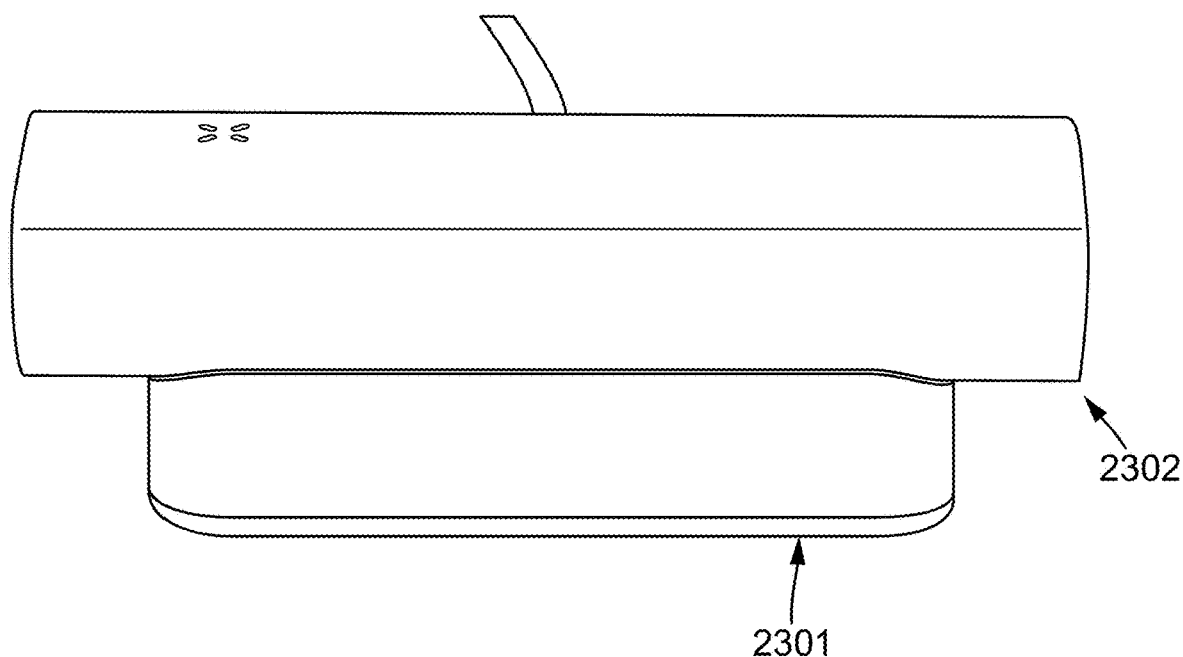
FIG. 22 is a device in a charging cradle.

A user may place the electronic smoking device in a charging cradle. The charging cradle may be a holder with charging contact configured to mate or couple with the charging pins on the electronic smoking device to provide charge to the energy storage device in the electronic vaporization device from a power source (e.g., wall outlet, generator, and/or external power storage device). FIG. 22 shows a device 2302 in a charging cradle 2301. The charging cable may be connected to a wall outlet, USB, or any other power source. The charging pins (not shown) on the device 2302 may be connected to charging contacts (not shown) on the charging cradle 2301. The device may be configured such that when the device is placed in the cradle for charging a first charging pin on the device may contact a first charging contact on the charging cradle and a second charging pin on the device may contact a second charging contact on the charging cradle or the first charging pin on the device may contact a second charging contact on the charging cradle and the second charging pin on the device may contact the first charging contact on the charging cradle. The charging pins on the device and the charging contacts on the cradle may be in contact in any orientation. The charging pins on the device and the charging contacts on the cradle may be agnostic as to whether they are current inlets or outlets. Each of the charging pins on the device and the charging contacts on the cradle may be negative or positive. The charging pins on the device may be reversible.

Figure 23:
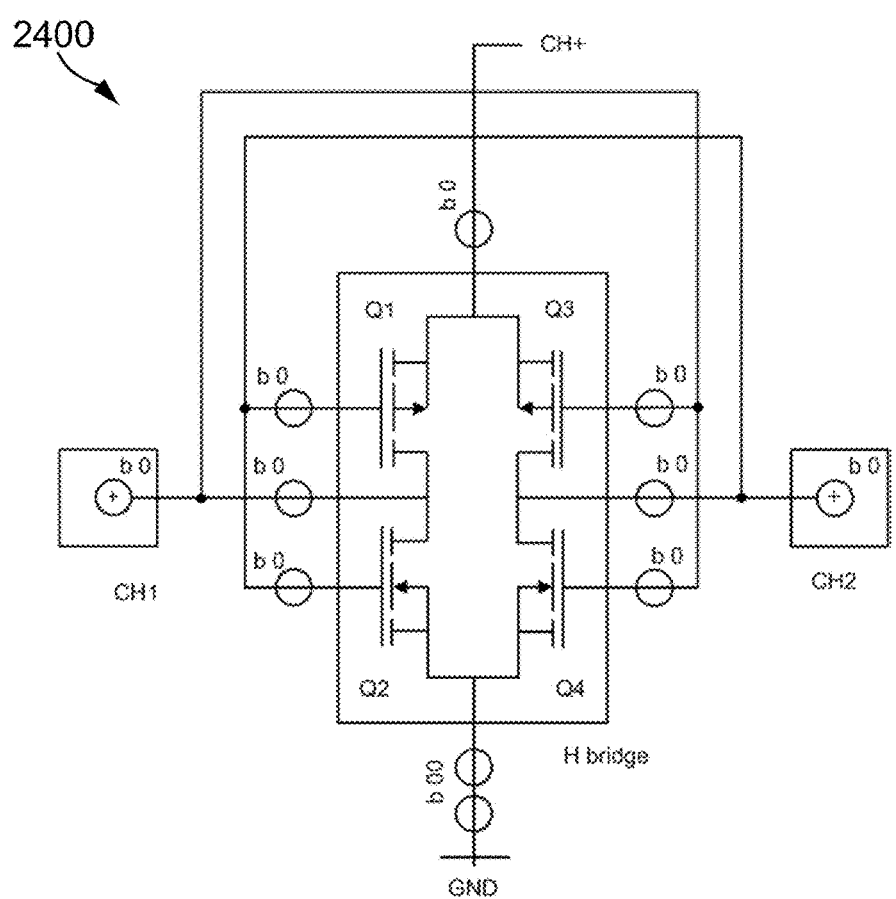
FIG. 23 is a circuit provided on a PCB configured to permit a device to comprise reversible charging contacts.

FIG. 23 shows a circuit 2400 that may permit the charging pins on the device to be reversible. The circuit 2400 may be provided on a PCB in electrical communication with the charging pins. The circuit 2400 may comprise a metal-oxide-semiconductor field-effect transistor (MOSFET) H bridge. The MOSFET H bridge may rectify a change in voltage across the charging pins when the charging pins are reversed from a first configuration where in a first configuration the device is placed in the cradle for charging with the first charging pin on the device in contact with the first charging contact on the charging cradle to a second charging pin on the device in contact with the second charging contact on the charging cradle to a second configuration where the first charging pin on the device is in contact with the second charging contact on the charging cradle and the second charging pin on the device is in contact with the first charging contact on the charging cradle. The MOSFET H bridge may rectify the change in voltage with an efficient current path.

As shown in FIG. 23 the MOSFET H bridge may comprise two or more n-channel MOSFETs and two or more p-channel MOSFETs. The n-channel and p-channel MOSFETs may be arranged in an H bridge. Sources of p-channels MOSFETs (Q1 and Q3) may be in electrical communication. Similarly, sources of n-channel FETs (Q2 and Q4) may be in electrical communication. Drains of pairs of n and p MOSFETs (Q1 with Q2 and Q3 with Q4) may be in electrical communication. TA common drain from one n and p pair may be in electrical communication with one or more gates of the other n and p pair and/or vice versa. Charge contacts (CH1 and CH2) may be in electrical communication to common drains separately. A common source of the n MOSFETs may be in electrical communication to PCB ground (GND). The common source of the p MOSFETs may be in electrical communication with the PCB's charge controller input voltage (CH+). When CH1 voltage is greater than CH2 voltage by the MOSFET gate threshold voltages, Q1 and Q4 may be "on," connecting CH1 to CH+ and CH2 to GND. When CH2 voltage is greater than CH1 voltage by the FET gate threshold voltages, Q2 and Q3 may be "on," connecting CH1 to GND and CH2 to CH+. For example, whether there is 9V or −9V across CH1 to CH2, CH+ will be 9V above GND. Alternatively, a diode bridge could be used, however the MOSFET bridge may be more efficient compared to the diode bridge.

In some cases the charging cradle may be configured to be a smart charger. The smart charger may put the battery of the device in series with a USB input to charge the device at a higher current compared to a typical charging current. In some cases, the device may charge at a rate up to about 2 amps (A), 4A, 5A, 6A, 7A, 10A, or 15A. In some cases, the smart charger may comprise a battery, power from the battery may be used to charge the device battery. When the battery in the smart charger has a charge below a predetermined threshold charge, the smart charger may simultaneously charge the battery in the smart charger and the battery in the device.

Cartridge/Vaporizer Attachment

Any of the cartridges described herein may be adapted for securely coupling with an electronic inhalable aerosol device ("vaporizer") as discussed above. In particular described herein are cartridge designs that address the unrecognized problem of maintaining adequate electrical contact between a mouthpiece-containing cartridge and a rectangular vaporizer coupling region, particularly when the mouthpiece is held in a user's mouth.

Any of the cartridges described herein may be particularly well adapted for securing to a vaporizer by including a base region that mates with the rectangular coupling region of the vaporizer, where the base unit fits into a rectangular opening that is between 13-14 mm deep, 4.5-5.5 mm wide, and 13-14 mm long. The base having generally includes a bottom surface having a first electrical contact and a second electrical contact. In particular, any of the cartridges described herein may include a first locking gap on a first lateral surface of the base, and a second locking gap on a second lateral surface of the base that is opposite first lateral surface.

Figure 24A:
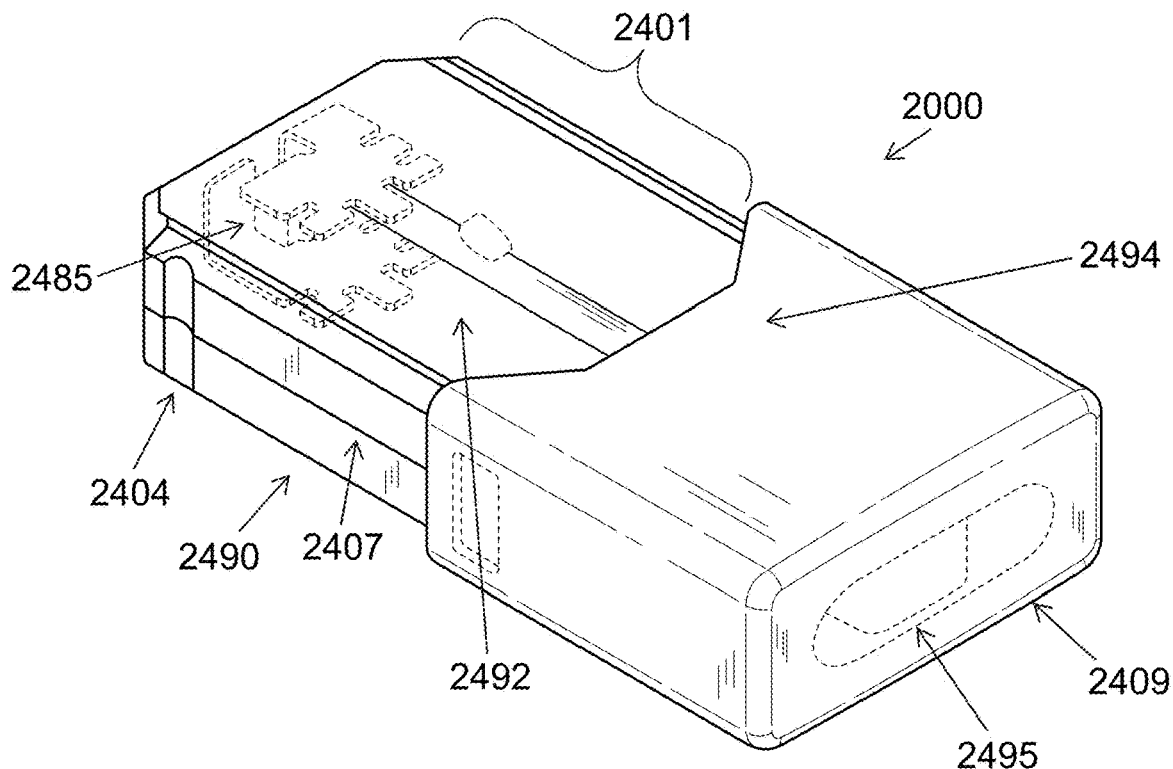
FIGS. 24A and 24B show top and bottom perspective views, respectively of a cartridge device holding a vaporizable material for securely coupling with an electronic inhalable aerosol device as described herein.
Figure 24B:
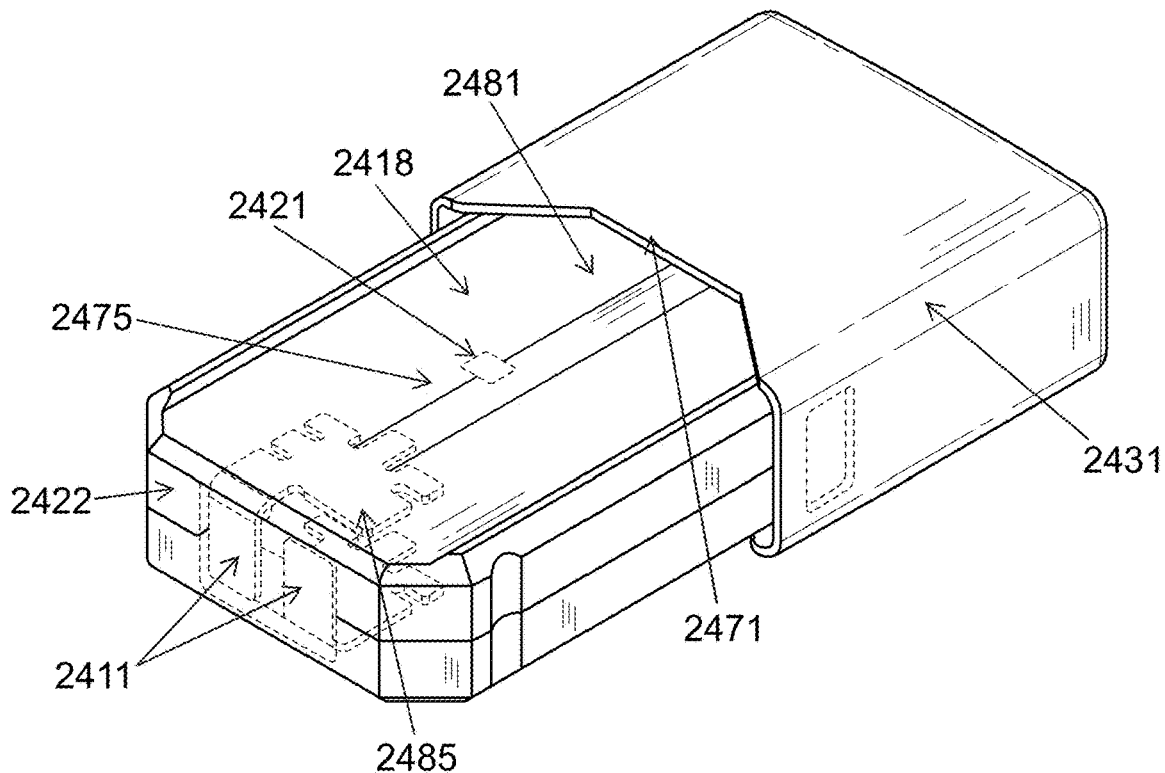

For example FIGS. 24A and 24B illustrate another variation of a cartridge similar to that shown in FIGS. 7A-15, discussed above, having a base region 2401 with at least one locking gap 2404 on the first minor lateral wall 2407. A second locking gap (not shown) may be present on the opposite minor lateral wall. One or both major lateral walls 2418 may include a detent 2421. Any of these cartridges may also include a mouthpiece 2409, which may be at an end that is opposite of the bottom 2422 of the cartridge, on which a pair of tabs (electrodes 2411) are positioned, shown in FIG. 24A (as previously described, above) bent over the distal end of the cartridge. FIGS. 25A and 25B show front and side views, respectively, of this example.

In FIGS. 24A-25B the locking gaps 2404, 2404' on either side are shown as channels in the side (lateral) walls. They may extend across the entire side wall, parallel to the bottom as shown, or they may extend only partially through and may preferably be centered relative to the width of the wall. In other variations the locking gap may be a divot, pit, opening, or hole (though not into the internal volume holding the vaporizable material). In general, the inventors have found that the vertical position of the locking gap may be important in maintaining the stability of the cartridge in the vaporizer, particularly in cartridges having a rectangular base region that is longer than 10 mm. Optimally, the locking gap may be between about 1 and 5 mm from the bottom of the base region, and more specifically, between about 3 and 4 mm (e.g., approximately 3.3 mm), as shown in FIG. 26A which indicates exemplary dimensions for the section through FIG. 26B.

The cartridges shown in FIGS. 24A and 24B also include a detent 2421 that is positioned between about 7 and 11 mm up from the bottom of the cartridge. The detent may help hold the cartridge base in the vaporizer, and may cooperate with the locking gap, but is optional and shown in dashed lines in FIGS. 24A-25B.

In FIGS. 24A-25B the cartridge base is also transparent, and shows an internal air channel (cannula 2505).

Figures 27A, 27B:
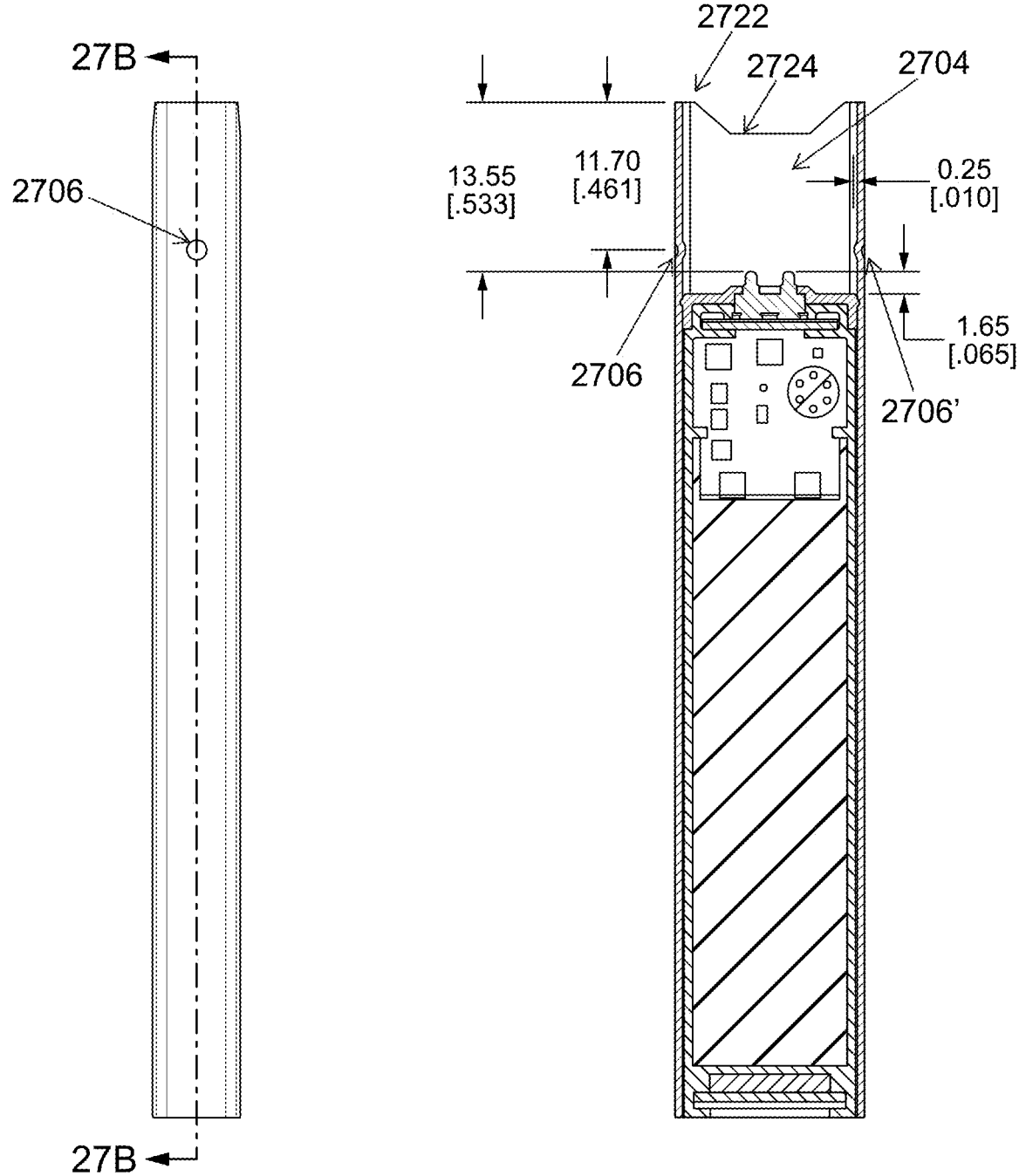
FIGS. 27A and 27B show an exemplary vaporizer device without a cartridge attached.

FIGS. 27 and 27B show another example of a vaporizer including a battery and control circuitry. FIGS. 27A and 27B also illustrate the mating region 2704. In this example, the mating region includes two detents 2706 that may mate with the locking gaps on the cartridge when it is inserted into the vaporizer. Exemplary dimensions for the mating region are shown. In this example the locking detents (which complement the locking gaps on the cartridge) are indentations that project into the mating region. These locking determent may be a ridge, pin, or other projection (including spring-loaded members).

Figure 28A:
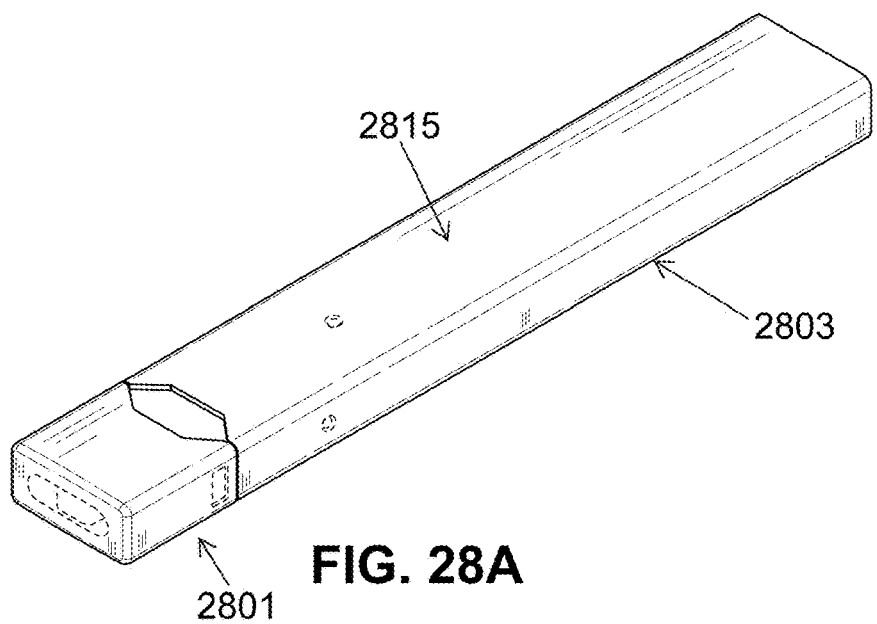
FIG. 28A shows a perspective view of a vaporizer coupled to a cartridge as described herein.
Figure 28B:
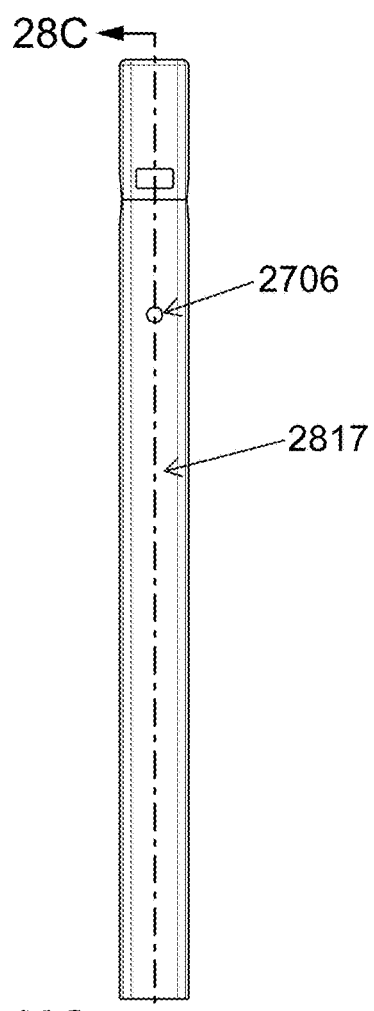
FIG. 28B shows a side view of the vaporizer of FIG. 28A.
Figure 28C:
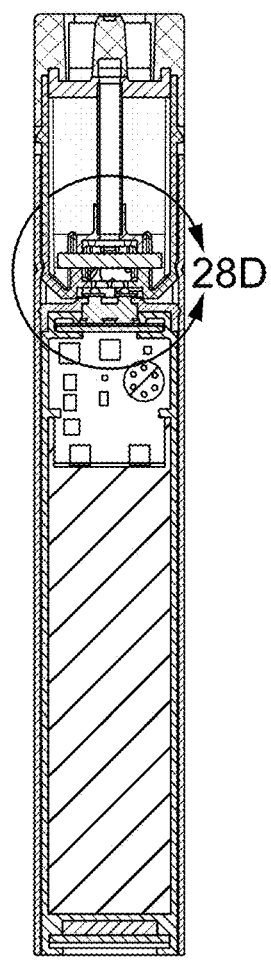
FIG. 28C shows a sectional view through the vaporizer of FIG. 28B taken through the dashed line.

FIGS. 28A-28D show an example of a vaporizer 2803 into which a cartridge 2801 has been securely loaded. In FIG. 28A the cartridge has been snapped into position so that the locking gaps of the cartridge engage with the locking detents in the vaporizer. FIG. 28B is side view and FIG. 28C show a sectional view; an enlarged portion of the sectional view is shown in FIG. 28D, showing the base of the cartridge seated in the mating region of the vaporizer. With the cartridge secured as shown, good electrical contact 2805 may be maintained.

Although the cartridges shown in FIGS. 24A-28D are similar, and include a proximal mouthpiece and distal base that are nearly equivalent in size, with the reservoir for the vaporizable material between them and the wick, resistive heater, heating chamber and electrodes at the distal most end (near the bottom of the base), many other cartridge configurations are possible while still securely seating into a vaporizer having the same vaporizer mating region shown in FIGS. 28A and 28B. For example, FIGS. 29A-29D illustrate alternative variations of cartridges having similar electrode. In FIG. 29A the base region includes two projecting feet that include locking gaps, and the electrodes on the base (not shown) connect via electrical traces (e.g. wires, etc.) to a heating element, wick and the reservoir nearer to the distal end (not visible).

In FIG. 29B the base extends further than 11 mm (e.g., 20-30 mm) and may house the reservoir (fluid storage compartment). Similarly in FIG. 29C the base region is the same as in FIG. 29B, but the more proximal portion is enlarged. In FIG. 29D the fluid non-base portion of the cartridge (more proximal than the base region) may have a different dimension. All of the variations shown in FIGS. 29A-29D, as in the variations shown in FIGS. 24A-25B, may mate with the same vaporizer, and because of the dimensions of the base region, may be securely held and maintain electrical contact, even when a user is holding the device in their mouth.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge comprising:
  a storage compartment configured to hold a vaporizable material, the storage compartment having a longitudinal dimension extending from a proximal end of the cartridge to a distal end of the cartridge, the cartridge having a first transverse dimension that is perpendicular to the longitudinal dimension, the cartridge having a second transverse dimension that is perpendicular to the longitudinal dimension and perpendicular to the first transverse dimension, the first transverse dimension being longer than the second transverse dimension;
  a mouthpiece at the proximal end of the storage compartment;
  a first contact surface extending in the first transverse dimension, the first contact surface proximate to the distal end, the first contact surface exposed outside of the storage compartment and accessible from the distal end;
  a second contact surface extending in the first transverse dimension, the second contact surface exposed proximate to the distal end, the second contact surface exposed outside of the storage compartment and accessible from the distal end, the first contact surface and the second contact surface disposed in a same plane proximate the distal end of the storage compartment;

a heater proximate to the distal end, the heater comprising:
  a first plate contact extending in the longitudinal dimension away from the distal end, the first plate contact electrically connected to the first contact surface;
  a second plate contact extending in the longitudinal dimension away from the distal end, the second plate contact electrically connected to the second contact surface;
  a wick disposed between the first plate contact and the second plate contact, two opposed ends of the wick being disposed within the storage compartment and configured to contact the vaporizable material; and
  a resistive heating element configured to heat the vaporizable material, the resistive heating element in contact with the first plate contact, the second plate contact, and the wick, wherein the first plate contact and the second plate contact are disposed to provide a heat shield configured to protect the cartridge from heat produced by the resistive heating element.

2. The cartridge of claim 1, wherein the storage compartment is transparent.

3. The cartridge of claim 1, wherein the first plate contact and the second plate contact are flat.

4. The cartridge of claim 1, wherein the resistive heating element is wound around the wick at least one time.

5. The cartridge of claim 1, wherein the heater comprises at least one condensation chamber.

6. The cartridge of claim 1, wherein the mouthpiece is fitted onto and encloses the proximal end of the storage compartment.

7. The cartridge of claim 6, wherein the mouthpiece is coupled to the storage compartment with a snap-fit coupling.

8. The cartridge of claim 1, wherein the storage compartment further comprises a channel integral to an exterior surface of the storage compartment, wherein the channel forms a first side of an air inlet passage.

9. The cartridge of claim 1, wherein the resistive heating element is attached to each of the first plate contact and the second plate contact.

10. The cartridge of claim 1, wherein the mouthpiece is positioned at least partially over the storage compartment and has a notch providing a view of the storage compartment.

11. The cartridge of claim 1, further comprising:
  a first flexible tab comprising the first contact surface; and
  a second flexible tab comprising the second contact surface.

12. The cartridge of claim 1, wherein the cartridge further comprises the vaporizable material within the storage compartment, and wherein the vaporizable material comprises a nicotine formulation.

13. The cartridge of claim 1, wherein the storage compartment has a rectangular cross section in a plane parallel to the first transverse dimension and the second transverse dimension.

14. The cartridge of claim 1, wherein the storage compartment is 13 millimeters to 14 millimeters long along the first transverse dimension, and wherein the storage compartment is 4.5 millimeters to 5.5 millimeters wide along the second transverse dimension.

15. The cartridge of claim 1, wherein the storage compartment comprises a first side and a second side opposite of the first side, and wherein the first side comprises a spacing detent.

16. A cartridge comprising:
  a storage compartment configured to hold a vaporizable material, the storage compartment having a longitudinal dimension extending from a proximal end of the cartridge to a distal end of the cartridge, the cartridge having a first transverse dimension that is perpendicular to the longitudinal dimension, the cartridge having a second transverse dimension that is perpendicular to the longitudinal dimension and perpendicular to the first transverse dimension, the first transverse dimension being longer than the second transverse dimension, the storage compartment having a rectangular cross section in a plane parallel to the first transverse dimension and the storage compartment;
  a mouthpiece at the proximal end of the storage compartment;
  a first contact surface extending in the first transverse dimension, the first contact surface proximate to the distal end, the first contact surface exposed outside of the storage compartment and accessible from the distal end;
  a second contact surface extending in the first transverse dimension, the second contact surface exposed proximate to the distal end, the second contact surface exposed outside of the storage compartment and accessible from the distal end, the first contact surface and the second contact surface disposed in a same plane proximate the distal end of the storage compartment;
  a heater proximate to the distal end of the storage compartment, the heater comprising:
    a first plate contact extending in the longitudinal dimension away from the distal end, the first plate contact electrically connected to the first contact surface;
    a second plate contact extending in the longitudinal dimension away from the distal end, the second plate contact electrically connected to the second contact surface;
    a wick disposed between the first plate contact and the second plate contact, two opposed ends of the wick being disposed within the storage compartment and configured to contact the vaporizable material; and
    a resistive heating element configured to heat the vaporizable material, the resistive heating element being attached to the first plate contact and the second plate contact and wound around the wick at least one time, wherein the first plate contact and the second plate contact are disposed to provide a heat shield configured to protect the cartridge from heat produced by the resistive heating element.

17. The cartridge of claim 16, wherein the storage compartment is configured to allow the vaporizable material to be visible through at least one surface.

18. The cartridge of claim 17, wherein the storage compartment is transparent.

19. The cartridge of claim 16, wherein the first plate contact and the second plate contact are flat.

20. The cartridge of claim 16, wherein the heater comprises a condensation chamber.

21. The cartridge of claim 16, wherein the mouthpiece is fitted onto and encloses the proximal end of the storage compartment.

22. The cartridge of claim 21, wherein the mouthpiece is coupled to the storage compartment with a snap-fit coupling.

23. The cartridge of claim 16, wherein the storage compartment further comprises a channel integral to an exterior surface of the storage compartment, wherein the channel forms a first side of an air inlet passage.

24. The cartridge of claim 16, wherein the mouthpiece is positioned at least partially over the storage compartment and has a notch that allows viewing of the storage compartment through the notch.

25. The cartridge of claim 16, wherein the cartridge further comprises the vaporizable material within the storage compartment, and wherein the vaporizable material comprises a nicotine formulation.

26. The cartridge of claim 16, wherein the storage compartment is 13 millimeters to 14 millimeters long along the first transverse dimension, and wherein the storage compartment is 4.5 millimeters to 5.5 millimeters wide long the second transverse dimension.

27. The cartridge of claim 16, wherein the storage compartment comprises a first side and a second side opposite of the first side, and wherein the first side comprises a spacing detent.

28. A cartridge comprising:
- a storage compartment configured to hold a vaporizable material, the storage compartment having a longitudinal dimension extending from a proximal end of the cartridge to a distal end of the cartridge, the cartridge having a first transverse dimension that is perpendicular to the longitudinal dimension, the cartridge having a second transverse dimension that is perpendicular to the longitudinal dimension and perpendicular to the first transverse dimension, the first transverse dimension being longer than the second transverse dimension;
- a mouthpiece fitted onto and enclosing the proximal end of the storage compartment;
- a first contact surface extending in the first transverse dimension, the first contact surface proximate to the distal end, the first contact surface exposed outside of the storage compartment and accessible from the distal end;
- a second contact surface extending in the first transverse dimension, the second contact surface exposed proximate to the distal end, the second contact surface exposed outside of the storage compartment and accessible from the distal end, the first contact surface and the second contact surface disposed in a same plane proximate the distal end of the storage compartment;
- a heater proximate to the distal end of the storage compartment, the heater comprising:
  - a first plate contact extending in the longitudinal dimension away from the distal end, the first plate contact electrically connected to the first contact surface;
  - a second plate contact extending in the longitudinal dimension away from the distal end, the second plate contact electrically connected to the second contact surface;
  - a heating element configured to heat the vaporizable material, the heating element comprising a resistive coil and opposed ends, a first end of the opposed ends attached to the first plate contact and a second end of the opposed ends attached the second plate contact, wherein the first plate contact and the second plate contact are disposed to provide a heat shield configured to protect the cartridge from heat produced by the heating element; and
  - a wick positioned at least partially within the resistive coil, the wick having opposed ends that extend into the storage compartment.

29. The cartridge of claim 28, wherein the storage compartment has a rectangular cross section in a plane parallel to the first transverse dimension and the second transverse dimension.

30. The cartridge of claim 28, wherein the storage compartment is configured to allow the vaporizable material to be visible through at least one surface.

31. The cartridge of claim 30, wherein the storage compartment is transparent.

32. The cartridge of claim 28, wherein the first contact surface and the second contact surface are disposed in a same plane proximate the distal end of the storage compartment.

33. The cartridge of claim 28, wherein the heater comprises a condensation chamber and the mouthpiece comprises a second condensation chamber.

34. The cartridge of claim 28, wherein the mouthpiece comprises a notch that allows viewing of the storage compartment through the notch.

35. The cartridge of claim 28, wherein the cartridge further comprises the vaporizable material within the storage compartment, and wherein the vaporizable material comprises a nicotine formulation.

36. The cartridge of claim 28, wherein the first plate contact and the second plate contact are flat.

37. The cartridge of claim 28, wherein the storage compartment is 13 millimeters to 14 millimeters long along the first transverse dimension, and wherein the storage compartment is 4.5 millimeters to 5.5 millimeters wide along the second transverse dimension.

38. The cartridge of claim 28, wherein the storage compartment comprises a first side and a second side opposite of the first side, and wherein the first side comprises a spacing detent.

* * * * *